United States Patent

Shiu et al.

[11] Patent Number: 5,555,283
[45] Date of Patent: Sep. 10, 1996

[54] COMPUTER-CONTROLLED MINIATURE MULTILEAF COLLIMATOR

[75] Inventors: Almon S. Shiu, Bellaire; James R. Ewton, Pearland; Henry E. Rittichier, Missouri City; Jeremy Wong, Houston; Samuel S. Tung, Missouri City, all of Tex.

[73] Assignee: Board of Regents of the University of Texas System, Austin, Tex.

[21] Appl. No.: 488,404

[22] Filed: Jun. 7, 1995

[51] Int. Cl.⁶ ............................................. G21K 1/02
[52] U.S. Cl. ...................... 378/151; 378/150; 378/147
[58] Field of Search .................................. 378/145, 147, 378/149, 150, 151, 152, 153, 64, 65, 148

[56] References Cited

U.S. PATENT DOCUMENTS 4,868,843  9/1989  Nunan ........................................ 378/152

*Primary Examiner*—Don Wong
*Attorney, Agent, or Firm*—Rosenblatt & Redano P.C.

[57] ABSTRACT

This invention relates to the field of miniature multileaf collimators for use in shaping a radiation beam used in stereotactic radiosurgery And radiotherapy. More particularly, the present invention relates to the use of a computer-controlled miniature multileaf collimator capable of shaping a radiation beam for use in optimal treatment of nonspherical lesions by radiosurgery and radiotherapy.

20 Claims, 4 Drawing Sheets

COMPUTER-CONTROLLED MINIATURE MULTILEAF COLLIMATOR

BACKGROUND OF THE INVENTION

1. Field of the Invention

This invention relates to the field of miniature multileaf collimators for use in shaping a radiation beam used in stereotactic radiosurgery and radiotherapy. More particularly, the present invention relates to the use of a computer-controlled miniature multileaf collimator capable of shaping a radiation beam for use in optimal small field treatment of nonspherical lesions by radiosurgery and radiotherapy.

2. Description of the Prior Art

In the art of stereotactic radiosurgery, patients are bombarded with radiation beams aimed to deliver a lethal radiation dose to a small tumor or lesion in the brain with minimum dose exposure to normal tissue surrounding the tumor or lesion. Linac-based stereotactic radiosurgery is a technique that focuses a circular radiation beam of x-rays to deliver a single fraction of high dose to a precisely defined spherical target volume through multiple noncoplanar arcs that simulate isotropic radiation. Prior art methods of stereotactic radiosurgery use multiple overlapping spherical treatments to treat nonspherical target volumes. This method has many drawbacks, including significantly increased treatment times, and dose inhomogeneity in the target volume. Such inhomogeneity problems are discussed in Nedzi, L. A.; Kooy, H. M.; Alexander, E.; Gelman, R. S.; Loeffler, J. S. Variables Associated With the Development of Complications From Radiosurgery of Intracranial Tumors, *Int. J. Radiat. Oncol. Biol. Phys.* 21: 591–99, 1991.

In the past, attempts in the prior art to minimize the dose inhomogeneity problem have led to underdosing near the edge of the target volume just outside the overlapping region of the successive spheres. Such underdosing problems are discussed in Bova, F. University of Florida Stereotactic Radiosurgery Program (Abstr.). SSII 4: AAPM Annual meeting, Med. Phys. 16:511, 1989.

Other prior art devices have attempted to more precisely shape the radiation beam to conform to the geometry of the target volume by using four rectangular blocks in combination with a conventional circular collimator. Such a device is described in Leavitt, D. D.; Gibbs, F. A.; Heibrun, M. P.; Moeller, J. H.; Takach Jr., G. A. Dynamic Field Shaping to Optimize Stereotactic Radiosurgery. *Int. J. Radiat. Oncol. Biol. Phys.* 21:1247–55; 1991. The variety of nonspherical beam shapes achievable with such a device is extremely limited due to the fact that only four straight edges can be used in conjunction with the spherical configuration of the circular collimator to form a dynamically shaped beam.

Another drawback of the prior art multileaf collimators is that they are designed for large field treatments in the range of 40 centimeters by 40 centimeters. Such collimators have leaf widths of 1.0 to 1.25 centimeters at isocenter, the beam-shaping capabilities of such collimators are too coarse for radiosurgical use. An example of a prior art multileaf collimator intended for delivering radiation to a large treatment area is disclosed in U.S. Pat. No. 5,160,847 to Leavitt, et al. ("the Leavitt patent").

Prior art multileaf collimators lack leaf position-indicating devices that are sufficiently precise and accurate for use in small field treatment applications. Prior art multileaf collimator position-measuring devices have included potentiometers, as disclosed in the Leavitt patent. Potentiometer based position indicating devices are unreliable for measuring leaf movement of less than 0.2 millimeters.

During stereotactic radiosurgery, the radiation source is moved along an arc defined by a gantry. The point at which all radial lines defining this arc intersect is known as the isocenter of the radiation beam. Such movement of the radiation source is customarily employed to totally irradiate a tumor or lesion. Due to the nonuniform shape of tumors and lesions, it is desirable to change the beam geometry as the radiation source moves along the arc. This is known as dynamic shaping. Many prior art multileaf collimators have limited dynamic shaping capability because all of the leaves cannot be moved at one time. In order for dynamic shaping to be effective, the multileaf collimator must have the capability to reposition the leaves quickly.

The present invention overcomes the drawbacks of the prior art by providing a computer-controlled miniature multileaf collimator capable of dynamically shaping beam geometry to closely conform to nonspherical targets. Additionally, the present invention is designed for small field treatments, in the range of 6 centimeters by 6 centimeters at isocenter. The present invention further comprises position-indicating means sufficiently accurate and precise for use in small field treatments.

SUMMARY OF THE INVENTION

The present invention provides a computer-controlled miniature multileaf collimator capable of dynamically shaping a radiation beam projected at isocenter from a radiation source. The present invention comprises a first bank of tapered leaves, arranged one behind the other. This configuration is referred to herein as a "substantially stacked configuration." When used in conjunction with a radiation source, each leaf has a proximal edge nearest to the radiation source, a leading edge perpendicular to the proximal edge, and a distal edge, opposite the proximal edge.

In conventional uses of a collimator in stereotactic radiosurgery, the radiation source is usually placed above the leaves and the patient is positioned below the leaves. In this conventional configuration, the leaves in each bank are vertically oriented, with their proximal edges on top and their distal edges on the bottom. Each leaf in the first bank is sufficiently thin such that when the distal edge of each leaf is spaced approximately 75 centimeters from the radiation source projected at isocenter, the projected width of each leaf at isocenter is less than 5 millimeters. The term "width" as used in this specification refers to the distance between the distal and proximal edges of any leaf.

The present invention further comprises a second bank of tapered leaves arranged in a substantially stacked configuration. The second bank of leaves contains at least as many leaves as the first bank of leaves. When used in conjunction with a radiation source, each leaf in the second bank has a proximal edge Nearest to the radiation source, a leading edge perpendicular to the proximal edge and a distal edge opposite the proximal edge. Each leaf in the second bank is sufficiently thin such that when the distal edge of each leaf is spaced approximately 75 centimeters from the radiation source projected at isocenter, the projected width of each leaf at isocenter is less than 5 millimeters. The projected width at isocenter of the leaves in the first and second banks is a feature of the present invention that makes it suitable for small field treatment.

A drive shaft is attached to each leaf such that axial movement of the drive shaft results in movement of a leaf in one of the banks toward or away from a leaf in the other bank.

A reversible motor is coupled to each drive shaft. The motor is capable of axially displacing each drive shaft resulting in the displacement of each leaf along an axis parallel to the proximal edge of the leaf. The reversible characteristic of the motor allows it to move a leaf in one bank either toward or away from a leaf in the other bank.

The invention further comprises a motor controller electrically coupled to each motor. Each controller comprises a memory capable of receiving, storing, and transmitting a signal indicative of the position of the leaf coupled to the drive shaft that is coupled to the motor to which the controller is coupled. The controller is further capable of transmitting a signal to the motor to change the position of the drive shaft by a predetermined distance.

The present invention further comprises a first position-indicating device coupled to each motor and capable of detecting the position of each leaf, detecting axial movement of each leaf of less than 0.1 millimeters, and transmitting a first signal indicative of each leaf's position.

The present invention further comprises a programmable computer comprising a memory capable of storing desired position data for each leaf for a multiplicity of predetermined radiation beam shapes, and a display screen capable of indicating the position of each leaf. The computer further comprises a comparator electrically coupled to receive signals from the first position-indicating means, to compare those signals to desired position data stored in memory for each leaf, to transmit a message to the display screen if the difference between the position indicated by the position-indicating signal and the desired position for any leaf is not within a predetermined tolerance, and to transmit signals to the motor controller to move any of the leaves to a desired position.

DETAILED DESCRIPTION OF THE PREFERRED EMBODIMENTS

Figure 1:
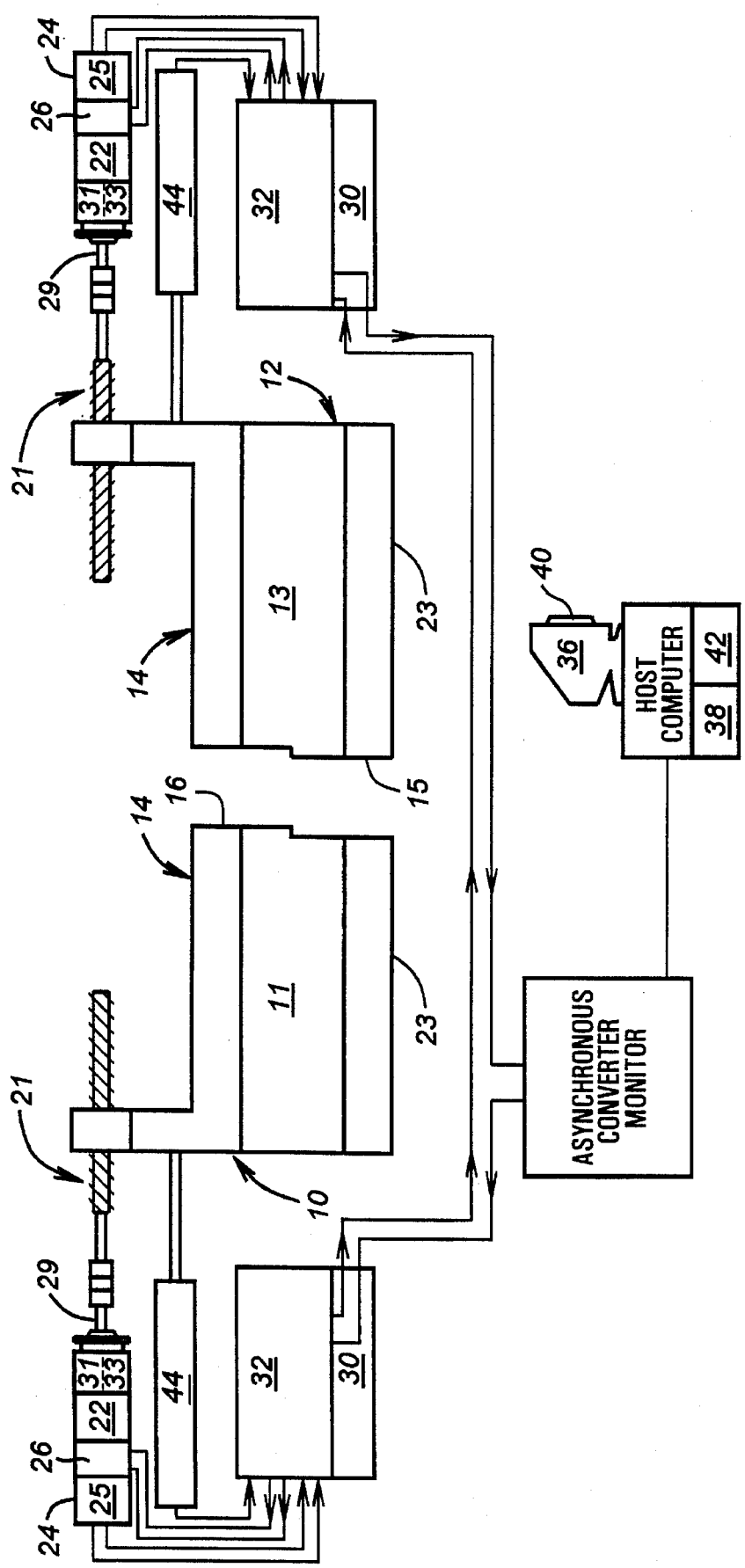
FIG. 1 is a front view of a preferred embodiment of the present invention.
Figure 2:
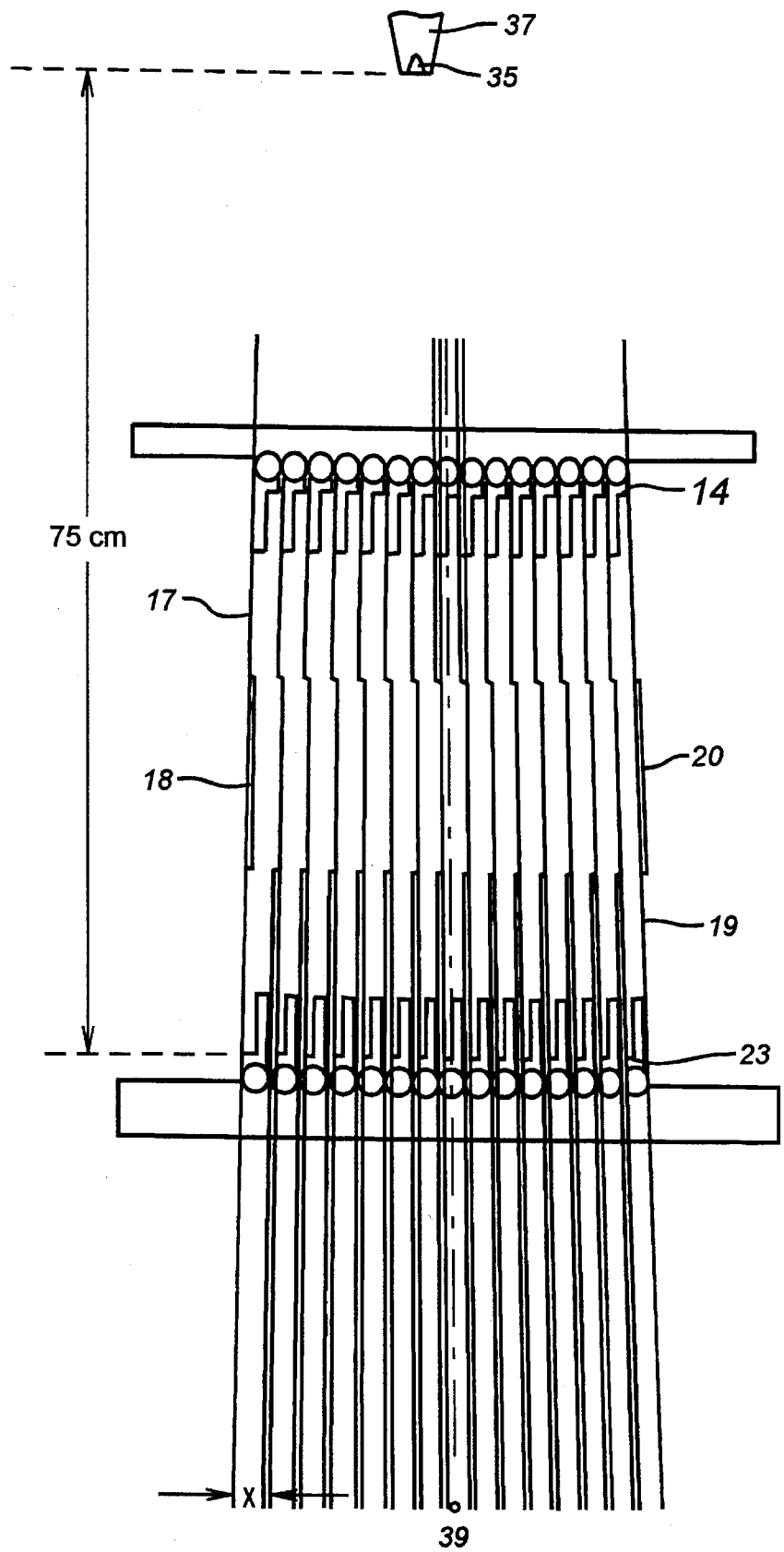
FIG. 2 is a side view of a leaf bank of the present invention.
Figure 3A:
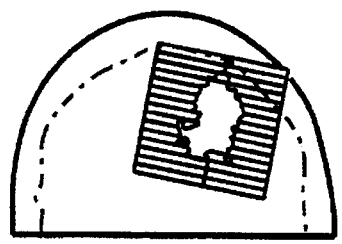
FIGS. 3A–3B are top views of the present invention depicting a dynamic shaping sequence.
Figure 3B:
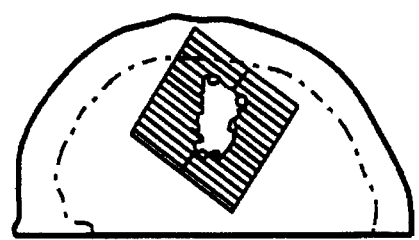
Figure 4:
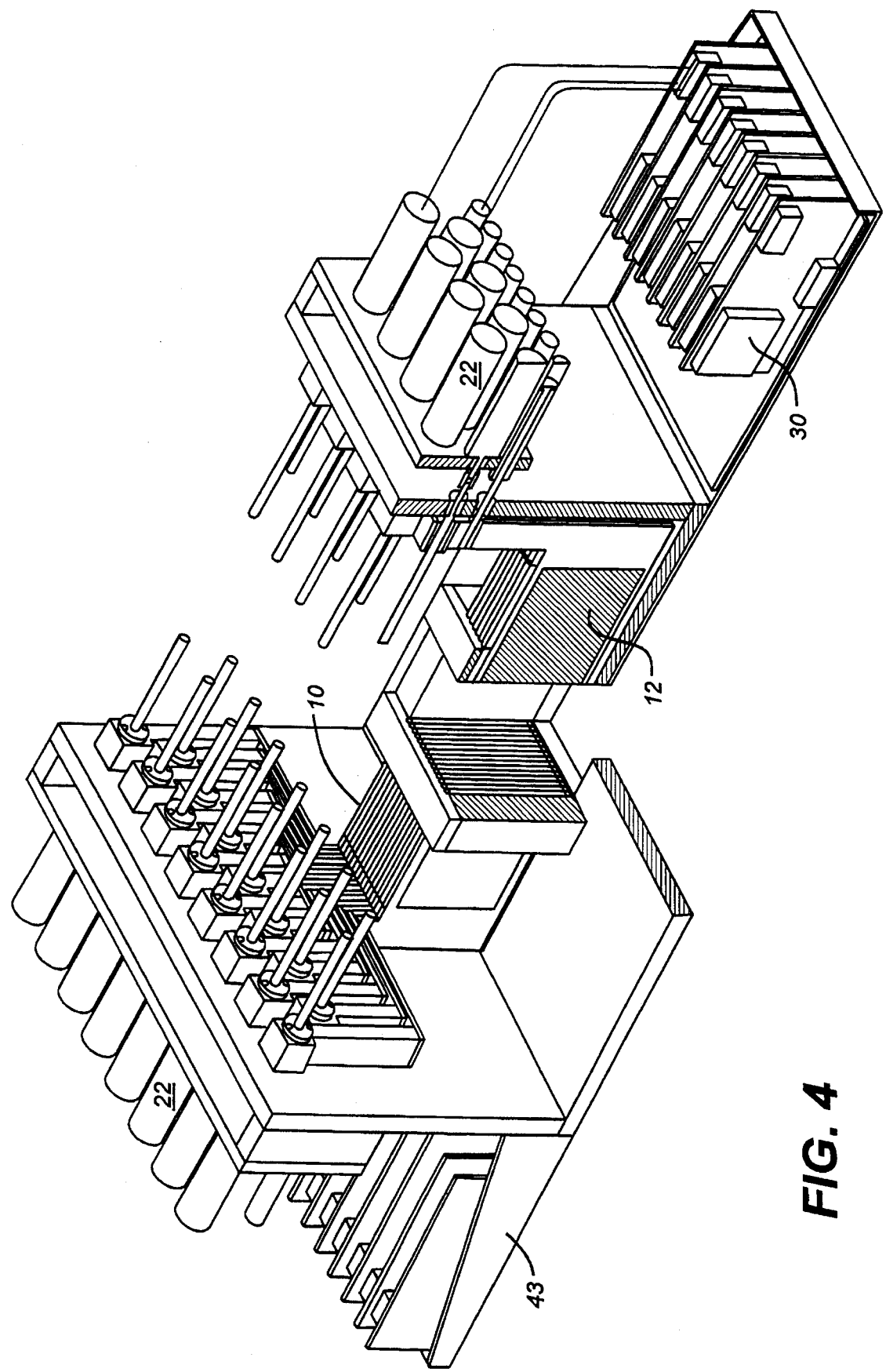
FIG. 4 is an isometric view of the present invention.

The present invention is directed toward a computer-controlled miniature multileaf collimator capable of dynamically shaping a radiation beam projected at isocenter from a radiation source. As shown in FIGS. 1, 2, and 4, the miniature multileaf collimator comprises a first bank of tapered leaves 10 arranged in a substantially stacked configuration. Each leaf has a proximal edge 14 nearest to a radiation source 35, a leading edge 15–16 perpendicular to the proximal edge, and a distal edge 23 opposite the proximal edge.

The present invention further comprises a second bank of tapered leaves 12 arranged in a substantially stacked configuration and containing at least as many leaves as the first bank of tapered leaves. Each leaf in the second bank also has a proximal edge nearest to a radiation source, and a leading edge perpendicular to the proximal edge. The leaves in the first and second banks are sufficiently thin such that when the distal edges of each leaf are spaced approximately 75 centimeters from a radiation source projected at isocenter, the projected width of each leaf at isocenter is less than 5 millimeters. The projected width "X" in FIG. 2 is less than 5 millimeters.

As shown in FIG. 1, the leading edge 16 of the leaves in the second bank of leaves face the leading edge 15 of the leaves in the first bank of leaves. In a preferred embodiment, each leaf is comprised of tungsten by over 90% on a weight basis.

In another preferred embodiment, as shown in FIG. 2, the proximal edges of the leaves in each bank are arranged along an arc defined by the arc length of a circle whose radius equals the distance from a leaf in the center of the bank to a radiation source whose beam the collimator is intended to shape. In yet another embodiment, the number of leaves in each bank is sufficiently large such that the distance from the first leaf to the last leaf in each bank is at least 45 centimeters.

In a preferred embodiment, the present invention further comprises a radiation source 35 capable of projecting a radiation beam at isocenter as shown in FIG. 2. The source is mounted above the intersection of said first and second leaf banks such that the proximal edges of said leaves are nearest to the radiation source. In another preferred embodiment, the radiation source is spaced approximately 75 centimeters from the distal edges of said leaves as shown in FIG. 2. In another preferred embodiment, the radiation source is contained within a radiation source housings 37.

In a preferred embodiment of the present invention, the leading edges in one of the leaf banks are stepped down 16 and the leading edges of the leaves in the other leaf bank are stepped up 15. As shown in FIG. 1, when the leaves in each bank are moved toward each other as far as they can go, the stepped up portion of each leading edge overhangs the stepped down portion of a corresponding leading edge.

In another preferred embodiment, as shown in FIG. 2, each leaf contains a front face 17 comprising a horizontal ridge 18 extending substantially across the front face. Each leaf further comprises a rear face 19 comprising a horizontal channel 20 extending substantially across the rear face and mounted at substantially the same height as said ridge such that each ridge protrudes into the channel of an adjacent leaf.

As shown in FIGS. 1 and 4, the invention further comprises a drive shaft 21 attached to each leaf such that axial movement of the drive shaft results in movement of the attached leaf in one of the banks toward or away from a leaf in the other leaf bank. In a preferred embodiment, the drive shaft is a rotatable drive screw, as shown in FIG. 1.

The invention further comprises a reversible motor 22 coupled to each drive shaft and capable of axially displacing each drive shaft, resulting in the displacement of each leaf attached to each drive shaft. In a preferred embodiment, the motor is a Model No. 1624, available from MicroMo Electronics, Inc. of St. Petersburg, Fla.

Figure 5:
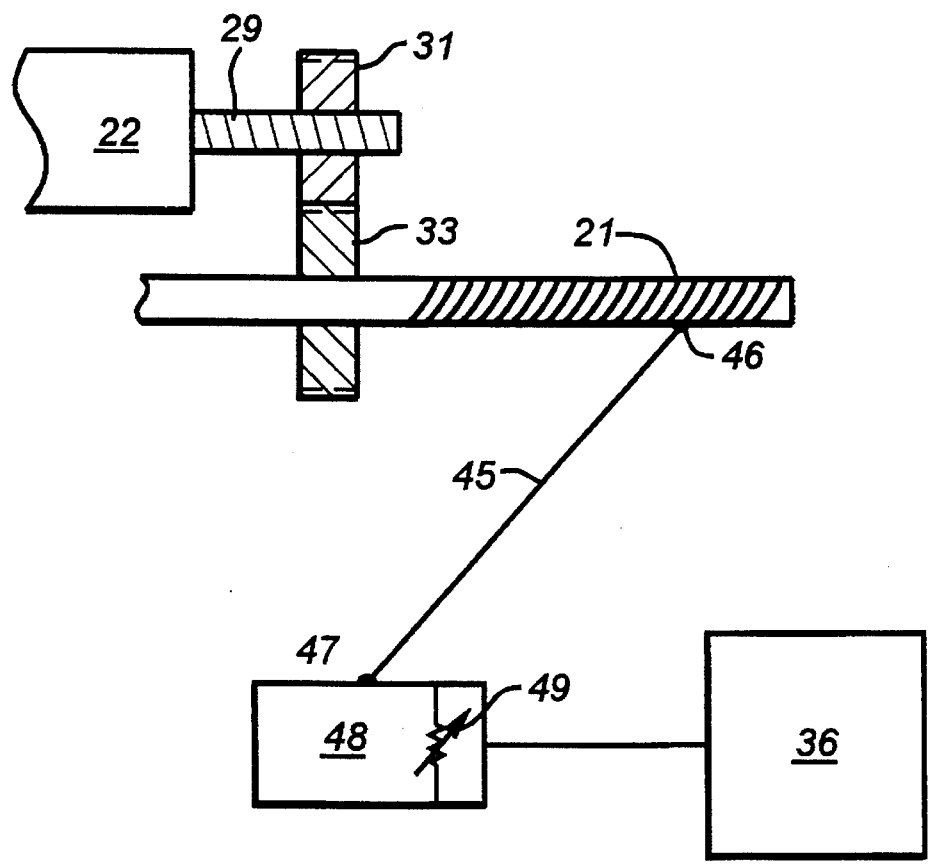
FIG. 5 is a block diagram of a second position-indicating device of the present invention.

In another preferred embodiment, each motor comprises a rotatable motor shaft 29, a first drive gear 31 attached to the rotatable motor shaft, and a second drive gear 33 attached to the drive shaft and rotatably coupled to the first drive gear as shown in FIG. 5. This rotatable coupling may be by direct "tooth-to-tooth" engagement or by a mechanical linkage, such as a chain or belt. In this embodiment, the speed of axial movement of the drive shaft is predetermined by selecting the rotational speed of the motor shaft and the gear ratio of the first drive gear to the second drive gear.

The invention further comprises a first position-indicating device 24 capable of detecting the position of each leaf, detecting axial leaf movement of less than 0.1 millimeters, and transmitting a first signal indicative of each leaf's position, as shown in FIG. 1. In a preferred embodiment, the first position-indicating device comprises a magnetic encoder 25 coupled to the motor to send out a pulse signal at a set rate and at a predetermined phase angle when the motor is operating. In a preferred embodiment, the encoder generates 16 pulses per motor shaft rotation. The encoder changes the phase angle of its signal when the motor reverses direction. In a preferred embodiment, the magnetic encoder is Model No. HEM1624E16, sold by MicroMo Electronics of St. Petersburg, Fla. The first position-indicating device further comprises a counter 26 capable of counting the pulses at each phase angle generated by the encoder.

In one embodiment, the motor shaft rotates at 700 revolutions per millimeter of leaf movement. The magnetic encoder measures each revolution, thereby having a resolution of 1/700 millimeters or 0.0014 millimeters. This fine resolution exceeds that achievable with potentiometer based measurement systems.

The invention further comprises a motor controller 30 electrically coupled to each motor as shown in FIG. 5. The controller comprises a memory 32 capable of receiving, storing, and transmitting a signal indicative of the position of the leaf coupled to the drive shaft that is coupled to the motor to which the controller is coupled. The controller is coupled to receive a position indicating signal from the position indicating device. The controller is further capable of transmitting a signal to the motor to change the position of the drive shaft a predetermined distance.

In a preferred embodiment, the motor controller is a Model No. PRV-0228A-01, sold under the name "SRS Vane Driver Board," by the Parvus Corporation of Salt Lake City, Utah. In a preferred embodiment, all of the motor controllers for a single bank of leaves are mounted on a mother board, sold by the Parvus Corporation of Salt Lake City, Utah, under the trade name "SRS Mother Board," bearing Model No. PRV-0227A-01. In another preferred embodiment, the mother boards associated with each bank of leaves can communicate with each other by use of an RS-422 Serial Driver Board, sold by the Parvus Corporation of Salt Lake City, Utah, under Model No. PRV-0105A-02.

In a preferred embodiment, the first and second banks of leaves, drive shafts, motor, motor controllers, and position-indicating devices are contained in a portable collimator housing 43 as shown in FIG. 4. In this embodiment, the collimator housing is detachably mountable to the radiation source housing.

The invention further comprises a programmable computer 36 comprising a memory 38 capable of storing desired position data for each leaf for a multiplitity of predetermined radiation beam shapes as shown in FIG. 5. In a preferred embodiment, a computer program, referred to as the "MMLC Setting Program," may be used to calculate the leaf positions that conform to a desired radiation field shape and graphically display the contour of the leaves. A listing of the MMLC Setting Program source code is presented at the end of this patent specification. The MMLC Setting Program provides desired leaf position coordinates to another program, known as the "MMLC Control Program."

In a preferred embodiment, the MMLC Control Program receives position data for each leaf from the MMLC Setting Program and sends a signal to each motor controller memory, instructing each motor controller where to position its respective leaf. A listing of the MMLC Control Program source code is presented at the end of this patent specification.

As shown in FIG. 5, the computer further comprises a display screen 40 capable of indicating the position of each leaf and a comparator 42 electrically coupled to receive signals from the first position-indicating device, to compare those signals to desired position data stored in memory for each leaf, and to transmit a message to the display screen that the difference between the position indicated by the position-indicating signal and the desired position for each leaf is not within a predetermined tolerance. In a preferred embodiment, the computer can also transit signals to each motor controller to move any leaf to a desired position.

In a preferred embodiment, the programmable computer can communicate with each of the mother boards via an asynchronous converter monitor, sold by the Parvus Corporation of Salt Lake City, Utah, under Model No. PRV-0011A-01. The software used to the allow programmable computer to communicate with each vane driver broad in a preferred embodiment is available from the Parvus Corporation of Salt Lake City, Utah, under the trade name "PC ParvNET."

In a preferred embodiment, as shown in FIG. 5, the invention further comprises a second position-indicating device 44 attached to each drive shaft and coupled to send a position-indicating signal to the programmable computer. The second position-indicating devices comprises a wiper blade 45 having a first end 46 attached to a drive shaft such that when the drive shaft moves, the wiper blade moves. Each wiper blade also comprises a second end 47. The second position-indicating device further comprises a potentiometer 48 comprising a variable resistor 49 coupled to the second end of the wiper blade such that movement of the wiper blade resulting from movement of the drive shaft results in a change in the resistance of said resistor.

Many modifications and variations may be made in the embodiments described herein and depicted in the accompanying drawing without departing from the concept of the present invention. Accordingly, it is understood that the embodiments described and illustrated herein are illustrative only and are not intended as a limitation upon the scope of this invention.

The source code for the MMLC Setting Program and the MMLC Control Program are provided below.

MMLC SETTING PROGRAM

```
misc.c
/* ========================= include files ========================= */ include <stdio.h>

/* ========================= function name ========================= */ int SYSbufinit (buf, offset, size)

/* ========================= comments ========================= */
/*
Initializes a buffer.
 */
/* ========================= declarations ========================= */
/*
type       parameter    i/o      description
---------  -----------  -------  --------------------------------------*/
char       *buf;        /* i/o   buffer                                */
int        offset;      /* i     offset in bytes to start of buffer    */
int        size;        /* i     number of bytes to initialize         */

/* ========================= log ========================= */
/*
return status description
---------------  -----------------------------------------------------
 1              Success
-1              Failure date      comments
--------  -----------------------------------------------------------
04/30/92  Creation - Jeremy Wong
 */
/* ================================================================ */

{ int i, j;

if ( buf == NULL ) goto ERROR_RETURN;

for ( i = offset, j = 0; j < size; i++, j++ ) buf[i] = 0;

return (1);

ERROR_RETURN:
fputs ("Error: SYSbufinit\n", stderr);
return (-1);

} mlc.c
/* ========================= include files ========================= */ include <stdio.h>
include <sys/param.h>
#include <sys/types.h>
#include <xview/xview.h>
#include <xview/panel.h>
```

```
#include <xview/notice.h>
#include <xview/textsw.h>
#include <xview/xv_xrect.h>
#include <xview/cms.h>
#include <xview/font.h>
#include <gdd.h>
#include "mlc_ui.h"
#include "mlc_u.h"
#include "mlc.h"

Attr_attribute    INSTANCE;
Attr_attribute    XINSTANCE;
void mlc_done_proc();

/* ======================= function name ======================= */ void main(argc, argv)

/* ======================= comments ======================= */
/*
MLC program
*/
/* ======================= declarations ======================= */
/*
type       parameter     i/o       description
---------  ------------  -------   ----------------------------------------*/
int        argc;         /* i      argument count                         */
char       *argv;        /* i      program arguments                      */

/* ======================= log ======================= */
/*
return status description
--------------  ---------------------------------------------------------- date      comments
--------  ----------------------------------------------------------------
07/17/92  Creation - Jeremy Wong
*/
/* ======================================================================= */

{
mlc_objects *mlc;
mlc_win_objects  *mlc_win;
mlc_popup1_objects    *mlc_popup1;
mlc_popup2_objects    *mlc_popup2;
mlc_popup3_objects    *mlc_popup3;
/*mlc_popup4_objects    *mlc_popup4;*/
mlc_x_objects *x_objects;
Rect rect, rect1;
Cms cms;
Xv_singlecolor colors[6];
char dir[MAXPATHLEN];
int i, j, stat;
void mlc_show_message1();

xv_init(XV_INIT_ARGC_PTR_ARGV, &argc, argv, 0);
INSTANCE = xv_unique_key();
XINSTANCE = xv_unique_key();

colors[0].red=255; colors[0].green=255; colors[0].blue=255; /*white */
```

```
colors[1].red=255; colors[1].green=0;   colors[1].blue=0;   /*red    */
colors[2].red=34;  colors[2].green=139; colors[2].blue=34;  /*green  */
colors[3].red=0;   colors[3].green=0;   colors[3].blue=139; /*blue   */
colors[4].red=255; colors[4].green=255; colors[4].blue=0;   /*yellow*/
colors[5].red=0;   colors[5].green = 0; colors[5].blue=0;   /*black  */ cms = xv_create (NULL, CMS,
                 CMS_SIZE, 6,
                 CMS_COLORS, colors,
                 CMS_TYPE, XV_STATIC_CMS);

mlc = mlc_objects_initialize(NULL, NULL);
mlc_win = mlc_win_objects_initialize(NULL, mlc->win);
mlc_popup1 = mlc_popup1_objects_initialize(NULL, mlc_win->win);
mlc_popup2 = mlc_popup2_objects_initialize(NULL, mlc_win->win);
mlc_popup3 = mlc_popup3_objects_initialize(NULL, mlc_win->win);
/*mlc_popup4 = mlc_popup4_objects_initialize(NULL, mlc_win->win);*/ x_objects = (mlc_x_objects *) malloc (sizeof (mlc_x_objects));
x_objects->ip = mlc_win;
x_objects->ip1 = mlc_popup1;
x_objects->ip2 = mlc_popup2;
x_objects->ip3 = mlc_popup3;
/*x_objects->ip4 = mlc_popup4;*/
x_objects->pmap = NULL;
x_objects->ngantry = 0;
x_objects->npoints = 0;
x_objects->save_npoints = 0;
x_objects->points = NULL;
x_objects->save_points = NULL;
for ( i = 0; i < NGANTRY; i++ ) {
   x_objects->gantry[i] = 0;
   x_objects->ngpoints[i] = 0;
   x_objects->gpoints[i] = NULL;

for ( j = 0; j < (NLEAF-1); j++ ) {
      x_objects->gpt_left[i][j].x = 0.;
      x_objects->gpt_right[i][j].x = 0.;
   } x_objects->stat_leaf[i] = 0;
   x_objects->stat_coll[i] = 0;
   x_objects->rotate_angle[i] = -90;
   x_objects->leaf_area[i] = 50;
   x_objects->average[i] = 5;
   x_objects->x1[i] = 0.;
   x_objects->x2[i] = 0.;
   x_objects->y1[i] = 0.;
   x_objects->y2[i] = 0.;
   SYSbufinit (x_objects->field[i], 0, FIELDNAME);
}
x_objects->stat = 0;
x_objects->beam = -1;
x_objects->interval = 10;
x_objects->shift_x = 0.;
x_objects->shift_y = 0.;
SYSbufinit (x_objects->infile, 0, sizeof (x_objects->infile));
SYSbufinit (x_objects->outfile, 0, sizeof (x_objects->outfile));
xv_get (cms, CMS_X_COLORS, x_objects->mlc_colors);
```

```
xv_set(mlc_win->win, XV_SHOW, TRUE, NULL);
xv_set(mlc_win->win, FRAME_CLOSED, FALSE, NULL);
xv_set(mlc_win->win, FRAME_DONE_PROC, mlc_done_proc, NULL);
xv_set(mlc_win->win, FRAME_SHOW_RESIZE_CORNER, FALSE, NULL);
xv_set(mlc_win->win, XV_KEY_DATA, XINSTANCE, x_objects, NULL);
xv_set(mlc_popup1->popup1, XV_KEY_DATA, XINSTANCE, x_objects, NULL);
xv_set(mlc_popup2->popup2, XV_KEY_DATA, XINSTANCE, x_objects, NULL);
xv_set(mlc_popup3->popup3, XV_KEY_DATA, XINSTANCE, x_objects, NULL);
/*xv_set(mlc_popup4->popup4, XV_KEY_DATA, XINSTANCE, x_objects,NULL);*/
mlc_show_message1 (x_objects, FALSE);
/*mlc_show_message2 (x_objects, FALSE);*/
xv_set (x_objects->ip->leaf_area, PANEL_VALUE, 50, NULL);
xv_set (x_objects->ip->interval, PANEL_VALUE, 10, NULL);
xv_set (x_objects->ip->average, PANEL_VALUE, 1, NULL);

SYSbufinit (dir, 0, sizeof (dir));
stat = getwd (dir);
if ( stat == 0 )
    fputs("mlc: cannot getwd\n", stderr);

frame_get_rect (x_objects->ip1->popup1, &rect);
rect.r_left = 20;
rect.r_top = 20;
frame_set_rect (x_objects->ip1->popup1, &rect);
xv_set (x_objects->ip1->dir1, PANEL_VALUE, dir, NULL);
xv_set (x_objects->ip1->file1, PANEL_VALUE, "", NULL);
xv_set (x_objects->ip1->dir3, PANEL_VALUE, dir, NULL);
xv_set (x_objects->ip1->file3, PANEL_VALUE, "", NULL);

frame_get_rect (x_objects->ip2->popup2, &rect);
rect.r_left = 20;
rect.r_top = 20;
frame_set_rect (x_objects->ip2->popup2, &rect);
xv_set (x_objects->ip2->dir2, PANEL_VALUE, dir, NULL);
xv_set (x_objects->ip2->file2, PANEL_VALUE, "", NULL);

frame_get_rect (x_objects->ip3->popup3, &rect);
frame_get_rect (x_objects->ip->win, &rect1);
rect.r_left = rect1.r_width;
rect.r_top = 0;
frame_set_rect (x_objects->ip3->popup3, &rect);
xv_set (x_objects->ip3->opt1, PANEL_VALUE, "", NULL);
xv_set (x_objects->ip3->opt2, PANEL_VALUE, "", NULL);
xv_set (x_objects->ip3->opt3, PANEL_VALUE, "", NULL);
xv_set (x_objects->ip3->opt4, PANEL_VALUE, "", NULL);
/*
frame_get_rect (x_objects->ip4->popup4, &rect);
frame_get_rect (x_objects->ip->win, &rect1);
rect.r_left = rect1.r_width - 150;
rect.r_top = 0;
frame_set_rect (x_objects->ip4->popup4, &rect);
xv_set (x_objects->ip4->openx1, PANEL_VALUE, "", NULL);
xv_set (x_objects->ip4->openx2, PANEL_VALUE, "", NULL);
xv_set (x_objects->ip4->openy1, PANEL_VALUE, "", NULL);
xv_set (x_objects->ip4->openy2, PANEL_VALUE, "", NULL);
*/
xv_main_loop(mlc->win);
exit(0);
}
```

```
/* ========================= include files ========================= */

/* ========================= function name ========================= */ void mlc_done_proc(frame)

/* ========================= comments ========================= */
/*
Exit from mlc window
 */
/* ========================= declarations ========================= */
/*
type       parameter   i/o     description
---------  ----------- ------- ------------------------------------*/
Frame      frame;      /* i    mlc window frame                    */

/* ========================= log ========================= */
/*
return status description
------------------------------------------------------------------- date       comments
--------   -------------------------------------------------------
07/17/92   Creation - Jeremy Wong
 */
/* ================================================================ */

{
 mlc_x_objects    *x_objects = (mlc_x_objects *) xv_get(frame,
XV_KEY_DATA, XINSTANCE);
 Xv_notice notice;
 int stat;

notice = xv_create (x_objects->ip->win, NOTICE,
                     NOTICE_MESSAGE_STRINGS,
                     "Please confirm exit from MLC", NULL,
                     NOTICE_BUTTON_YES, "Exit",
                     NOTICE_BUTTON_NO, "Cancel",
                     NOTICE_STATUS, &stat,
                     XV_SHOW, TRUE, NULL);
 switch ( stat ) {
    case NOTICE_YES:
       exit (0);
       break;
    case NOTICE_NO:
       xv_destroy_safe (notice);
       return;
       break;
 }
}

/* ========================= include files ========================= */

/* ========================= function name ========================= */ void mlc_done1_proc(frame)
```

```
/* ========================= comments ========================= */
/*
Undisplay optimize mlc window
 */
/* ========================= declarations ========================= */
/*
type       parameter    i/o      description
---------  ------------ -------- --------------------------------------*/
Frame      frame;       /* i     mlc window frame                     */

/* ============================= log ============================= */
/*
return status description
---------------  --------------------------------------------------- date     comments
-------- ---------------------------------------------------------
07/17/92 Creation - Jeremy Wong
 */
/* =============================================================== */

{
 mlc_x_objects    *x_objects = (mlc_x_objects *) xv_get(frame,
XV_KEY_DATA, XINSTANCE);
 void mlc_show_button();

xv_set (x_objects->ip3->popup3, FRAME_CMD_PUSHPIN_IN, FALSE, NULL);
 xv_set (x_objects->ip3->popup3, XV_SHOW, FALSE, NULL);
 mlc_show_button (x_objects, TRUE);
}

/* ======================= include files ======================= */

/* ======================= function name ======================= */ void mlc_cancel_mlc(item, event)

/* ========================= comments ========================= */
/*
Undisplay optimize mlc window
 */
/* ========================= declarations ========================= */
/*
type       parameter    i/o      description
---------  ------------ -------- --------------------------------------*/
Panel_item item;        /* i     panel item                            */
Event      *event;      /* i     pointer to event                      */

/* ============================= log ============================= */
/*
return status description
---------------  --------------------------------------------------- date     comments
-------- ---------------------------------------------------------
07/17/92 Creation - Jeremy Wong
 */
```

```
/* ================================================================== */
{
  mlc_popup3_objects   *ip = (mlc_popup3_objects *) xv_get(item,
XV_KEY_DATA, INSTANCE);
  mlc_x_objects   *x_objects = (mlc_x_objects *) xv_get(ip->popup3,
XV_KEY_DATA, XINSTANCE);
  void mlc_show_button();

xv_set (x_objects->ip3->popup3, FRAME_CMD_PUSHPIN_IN, FALSE, NULL);
  xv_set (x_objects->ip3->popup3, XV_SHOW, FALSE, NULL);
  mlc_show_button (x_objects, TRUE);

fputs("mlc: mlc_cancel_mlc\n", stderr);
}

/* ====================== include files ====================== */
/* ====================== function name ====================== */
void mlc_load_contour(item, event)

/* ========================== comments ========================== */
/*
Display load contour window
*/
/* ========================== declarations ========================== */
/*
type         parameter    i/o      description
---------    -----------  -----    -------------------------------------*/
Panel_item   item;        /* i     panel item                           */
Event        *event;      /* i     pointer to event                     */
/* ============================ log ============================ */
/*
return status description
--------------- ------------------------------------------------ date     comments
-------- ------------------------------------------------
07/17/92 Creation - Jeremy Wong
*/
/* ================================================================== */
{
  mlc_win_objects  *ip = (mlc_win_objects *) xv_get(item, XV_KEY_DATA,
INSTANCE);
  mlc_x_objects   *x_objects = (mlc_x_objects *) xv_get(ip->win,
XV_KEY_DATA, XINSTANCE);

xv_set (x_objects->ip->win, FRAME_LEFT_FOOTER, "", NULL);
  xv_set (x_objects->ip1->popup1, FRAME_CMD_PUSHPIN_IN, TRUE, NULL);
  xv_set (x_objects->ip1->popup1, XV_SHOW, TRUE, NULL);
  xv_set (x_objects->ip3->popup3, FRAME_CMD_PUSHPIN_IN, FALSE, NULL);
  xv_set (x_objects->ip3->popup3, XV_SHOW, FALSE, NULL);

fputs("mlc: mlc_load_contour\n", stderr);
}
```

```
/* ===================== include files ===================== */

/* ===================== function name ===================== */ void mlc_exit_mlc(item, event)

/* ===================== comments ===================== */
/*
Exit from mlc program
 */
/* ===================== declarations ===================== */
/*
type        parameter    i/o      description
---------   ------------ -------- -----------------------------------------*/
Panel_item  item;        /* i     panel item                              */
Event       *event;      /* i     pointer to event                        */

/* ===================== log ===================== */
/*
return status description
--------------  --------------------------------------------------------- date       comments
--------   ---------------------------------------------------------
07/17/92   Creation - Jeremy Wong
 */
/* ========================================================= */
{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 Xv_notice notice;
 int stat;

if ( x_objects->stat == 2 ) {
    notice = xv_create (x_objects->ip->win, NOTICE,
                       NOTICE_MESSAGE_STRINGS, "MLC has not been saved",
                       "Please confirm exit from MLC", NULL,
                       NOTICE_BUTTON_YES, "Exit",
                       NOTICE_BUTTON_NO, "Cancel",
                       NOTICE_STATUS, &stat,
                       XV_SHOW, TRUE, NULL);
    switch ( stat ) {
       case NOTICE_YES:
          exit (0);
          break;
       case NOTICE_NO:
          xv_destroy_safe (notice);
          return;
          break;
    }
 }
 else
    exit (0);
```

```
  fputs("mlc: mlc_exit_mlc\n", stderr);
}

/* ===================== include files ===================== */

/* ===================== function name ===================== */ int mlc_list_mlc(item, string, client_data, op, event)

/* ===================== comments ===================== */
/*
Select contour to display
*/
/* ===================== declarations ===================== */
/*
type         parameter    i/o      description
---------    ------------ -------- ---------------------------------------*/
Panel_item   item;        /* i     panel item                             */
char         *string;     /* i     label selected                         */
Xv_opaque    client_data; /* i     client data                            */
Panel_list_op op;         /* i     panel operation                        */
Event        *event;      /* i     pointer to event                       */

/* ===================== log ===================== */
/*
return status description
--------------  --------------------------------------------------------- date      comments
--------  ---------------------------------------------------------------
07/17/92  Creation - Jeremy Wong
*/
/* ========================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 int i, j, stat;
 void mlc_rotate();

xv_set (x_objects->ip->win, FRAME_LEFT_FOOTER, "", NULL);
 switch(op) {
 case PANEL_LIST_OP_DESELECT:
    fprintf(stderr, "mlc: mlc_list_mlc: PANEL_LIST_OP_DESELECT:
%s\n",string);
    break;

case PANEL_LIST_OP_SELECT:
    if ( x_objects->points != NULL ) {
       free (x_objects->points);
       x_objects->points = NULL;
    }
    if ( x_objects->save_points != NULL ) {
       free (x_objects->save_points);
       x_objects->save_points = NULL;
    }
```

```
      i = (int) client_data;
      x_objects->beam = i;
      x_objects->npoints = x_objects->ngpoints[i];
      x_objects->save_npoints = x_objects->npoints;
      if ( x_objects->npoints > 0 ) {
          x_objects->points = (point *) malloc (sizeof (point) *
                                              x_objects->npoints);
          x_objects->save_points = (point *) malloc (sizeof (point) *
                                              x_objects->npoints);
      }
      for ( j = 0; j < x_objects->ngpoints[i]; j++ ) {
          x_objects->points[j] = x_objects->gpoints[i][j];
          x_objects->save_points[j] = x_objects->gpoints[i][j];
      } x_objects->shift_x = 0.;
      x_objects->shift_y = 0.;
      xv_set (x_objects->ip->rotate, PANEL_VALUE,
              mlc_int_ext_rot (x_objects->rotate_angle[i]), NULL);
      XClearWindow ((Display *) xv_get(x_objects->ip->canvas1,XV_DISPLAY),
                    (Window) xv_get (canvas_paint_window(
                                     x_objects->ip->canvas1), XV_XID));
      XFlush ((Display *) xv_get (x_objects->ip->canvas1, XV_DISPLAY));

/*mlc_rotate (x_objects, x_objects->rotate_angle[i]);*/ x_objects->stat = 0;
      stat = mlc_disp_cont (x_objects);
      if ( stat != 1 ) {
          xv_set (x_objects->ip->win, FRAME_LEFT_FOOTER,
                  "Cannot display contour", NULL);
          return XV_OK;
      } stat = MLCfit (x_objects->points, x_objects->npoints);
      if ( stat == 0 ) {
          xv_set (x_objects->ip->win, FRAME_LEFT_FOOTER,
                  "Contour does not fit in mlc", NULL);
          /*return XV_OK;*/
      }
      x_objects->stat = 1;

if ( !x_objects->stat_leaf[i] ) {
          stat = MLCleaves (x_objects->points, x_objects->npoints,
                            x_objects->rotate_angle[i],
                            x_objects->leaf_area[i], x_objects->average[i],
                            x_objects->gpt_left[i],
                            x_objects->gpt_right[i]);
          if ( stat != 1 ) {
              xv_set (x_objects->ip->win, FRAME_LEFT_FOOTER,
                      "Cannot position mlc", NULL);
              return XV_OK;
          }
          x_objects->stat_leaf[i] = 1;
      } stat = MLCcheck (x_objects->points, x_objects->npoints,
                       x_objects->gpt_left[i], x_objects->gpt_right[i]);
      if ( stat != 1 ) {
        xv_set(x_objects->ip->win,FRAME_LEFT_FOOTER,"Cannot position mlc",
```

```
              NULL);
        return XV_OK;
    } stat = mlc_disp_mlc (x_objects);
    if ( stat != 1 ) {
       xv_set(x_objects->ip->win,FRAME_LEFT_FOOTER,"Cannot display mlc",
              NULL);
       return XV_OK;
    }
    x_objects->stat = 2;
    /*if ( x_objects->stat_coll[i] )
        stat = mlc_disp_coll (x_objects);*/
    xv_set (x_objects->ip->leaf_area, PANEL_VALUE,
            x_objects->leaf_area[i], NULL);
    if ( x_objects->average[i] == 3 )
       xv_set (x_objects->ip->average, PANEL_VALUE, 0, NULL);
    else if ( x_objects->average[i] == 5 )
       xv_set (x_objects->ip->average, PANEL_VALUE, 1, NULL);

fprintf(stderr, "mlc: mlc_list_mlc: PANEL_LIST_OP_SELECT:
%s\n",string);
    break;

case PANEL_LIST_OP_VALIDATE:
    fprintf(stderr, "mlc: mlc_list_mlc: PANEL_LIST_OP_VALIDATE:
%s\n",string);
    break;

case PANEL_LIST_OP_DELETE:
    fprintf(stderr, "mlc: mlc_list_mlc: PANEL_LIST_OP_DELETE:
%s\n",string);
    break;
 }
 return XV_OK;
}

/* ======================= include files ======================= */

/* ======================= function name ======================= */ void mlc_draw_mlc(item, event)

/* ======================= comments ======================= */
/*
Draw mlc on contour
 */
/* ======================= declarations ======================= */
/*
type       parameter     i/o      description
---------  ------------  -------  ------------------------------------*/
Panel_item item;         /* i     panel item                          */
Event      *event;       /* i     pointer to event                    */

/* ======================= log ======================= */
/*
return status description
-------------  -----------------------------------------------------
```

```
date      comments
--------  ----------------------------------------------------------
07/17/92  Creation - Jeremy Wong
 */
/* ================================================================ */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 int i, stat;

xv_set (x_objects->ip->win, FRAME_LEFT_FOOTER, "", NULL);
 if ( x_objects->stat == 0 ) {
    xv_set (x_objects->ip->win, FRAME_LEFT_FOOTER, "Load contour first",
            NULL);
    return;
 }

/*
   find intersection points of leaves and contour points
*/ i = x_objects->beam;
 stat = MLCleaves (x_objects->points, x_objects->npoints,
                   x_objects->rotate_angle[i], x_objects->leaf_area[i],
                   x_objects->average[i], x_objects->gpt_left[i],
                   x_objects->gpt_right[i]);
 if ( stat != 1 ) {
    xv_set (x_objects->ip->win, FRAME_LEFT_FOOTER,"Cannot position mlc",
            NULL);
    return;
 }
 x_objects->stat_leaf[i] = 1;

/*
   check for small contour that fits between 2 leaves
*/ stat = MLCcheck (x_objects->points, x_objects->npoints,
                  x_objects->gpt_left[i], x_objects->gpt_right[i]);
 if ( stat != 1 ) {
    xv_set (x_objects->ip->win, FRAME_LEFT_FOOTER,"Cannot position mlc",
            NULL);
    return;
 }

/*
   display mlc
*/

XClearWindow ((Display *) xv_get (x_objects->ip->canvas1, XV_DISPLAY),
               (Window) xv_get (canvas_paint_window(
                                 x_objects->ip->canvas1), XV_XID));
 XFlush ((Display *) xv_get (x_objects->ip->canvas1, XV_DISPLAY));

stat = mlc_disp_cont (x_objects);
 stat = mlc_disp_mlc (x_objects);
```

```
  if ( stat != 1 ) {
     xv_set (x_objects->ip->win, FRAME_LEFT_FOOTER, "Cannot display mlc",
             NULL);
     return;
  }
  x_objects->stat = 2;

fputs("mlc: mlc_draw_mlc\n", stderr);
}

/* ========================= include files ========================= */

/* ========================= function name ========================= */ void mlc_adjust_mlc(item, event)

/* ========================= comments ========================= */
/*
Adjust mlc manually
 */
/* ========================= declarations ========================= */
/*
type        parameter    i/o       description
---------   ------------ -------   ------------------------------------------*/
Panel_item  item;        /* i      panel item                                */
Event       *event;      /* i      pointer to event                          */

/* ========================= log ========================= */
/*
return status description
------------------------ ------------------------------------------------ date      comments
--------  ------------------------------------------------------------
07/17/92  Creation - Jeremy Wong
 */
/* ========================================================================= */

{
  mlc_win_objects  *ip = (mlc_win_objects *) xv_get(item, XV_KEY_DATA,
INSTANCE);
  mlc_x_objects    *x_objects = (mlc_x_objects *) xv_get(ip->win,
XV_KEY_DATA, XINSTANCE);
  void mlc_show_message1(), mlc_show_button(), mlc_adjust();

xv_set (x_objects->ip->win, FRAME_LEFT_FOOTER, "", NULL);
  if ( x_objects->stat < 2 ) {
     xv_set (x_objects->ip->win, FRAME_LEFT_FOOTER, "Draw mlc first",
             NULL);
     return;
  } xv_set (canvas_paint_window (x_objects->ip->canvas1),
          XV_KEY_DATA, XINSTANCE, x_objects,
          WIN_EVENT_PROC, mlc_adjust, NULL);

mlc_show_button (x_objects, FALSE);
  mlc_show_message1 (x_objects, TRUE);
```

```
 fputs("mlc: mlc_adjust_mlc\n", stderr);
}

/* ========================= include files ========================= */
/* ========================= function name ========================= */ void mlc_opt_mlc(item, event)

/* ========================= comments ========================= */
/*
Optimize mlc automatically
*/
/* ========================= declarations ========================= */
/*
type         parameter    i/o       description
---------    -----------  --------  ------------------------------------*/
Panel_item   item;        /* i      panel item                          */
Event        *event;      /* i      pointer to event                    */

/* ========================= log ========================= */
/*
return status description
--------------   ------------------------------------------------------ date       comments
--------   ------------------------------------------------------
07/17/92   Creation - Jeremy Wong
*/
/* ========================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 void mlc_show_button(), mlc_opt();

xv_set (x_objects->ip->win, FRAME_LEFT_FOOTER, "", NULL);
 if ( x_objects->ngantry == 0 ) {
    xv_set (x_objects->ip->win, FRAME_LEFT_FOOTER, "Load contour first",
           NULL);
    return;
 } xv_set (x_objects->ip3->popup3, FRAME_CMD_PUSHPIN_IN, FALSE, NULL);
 xv_set (x_objects->ip3->popup3, XV_SHOW, FALSE, NULL);
 mlc_show_button (x_objects, FALSE);
 mlc_opt (x_objects);

fputs("mlc: mlc_opt_mlc\n", stderr);
}

/* ========================= include files ========================= */
/* ========================= function name ========================= */
```

```
void mlc_save_mlc(item, event)

/* =========================== comments =========================== */
/*
Display save mlc window
 */
/* ========================== declarations ======================== */
/*
type        parameter    i/o      description
---------   -----------  ------   -------------------------------------*/
Panel_item item;         /* i     panel item                          */
Event      *event;       /* i     pointer to event                    */

/* ============================== log ============================= */
/*
return status description
--------------  --------------------------------------------------- date       comments
--------   ---------------------------------------------------
07/17/92   Creation - Jeremy Wong
 */
/* =============================================================== */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 Xv_notice notice;
 int i, found, stat;

xv_set (x_objects->ip->win, FRAME_LEFT_FOOTER, "", NULL);
 if ( x_objects->ngantry == 0 ) {
    xv_set (x_objects->ip->win, FRAME_LEFT_FOOTER, "Load contour first",
            NULL);
    return;
 } found = 0;
 for ( i = 0; i < x_objects->ngantry; i++ ) {
    if ( !x_objects->stat_leaf[i] )
       found = 1;
 } if ( found ) {
    notice = xv_create (x_objects->ip->win, NOTICE,
                        NOTICE_MESSAGE_STRINGS,
              "MLC not drawn for all leaves, do you want to save?", NULL,
                        NOTICE_BUTTON_YES, "Yes",
                        NOTICE_BUTTON_NO, "No",
                        NOTICE_STATUS, &stat,
                        XV_SHOW, TRUE, NULL);
    switch ( stat ) {
       case NOTICE_YES:
          xv_set (x_objects->ip2->popup2, FRAME_CMD_PUSHPIN_IN, TRUE,
                  NULL);
          xv_set (x_objects->ip2->popup2, XV_SHOW, TRUE, NULL);
          break;
```

```
        case NOTICE_NO:
           xv_destroy_safe (notice);
           return;
           break;
    }
 }
 else {
    xv_set (x_objects->ip2->popup2, FRAME_CMD_PUSHPIN_IN, TRUE, NULL);
    xv_set (x_objects->ip2->popup2, XV_SHOW, TRUE, NULL);
 } fputs("mlc: mlc_save_mlc\n", stderr);
}

/* ========================= include files ========================= */

/* ========================= function name ========================= */ void mlc_leaf_area(item, value, event)

/* ========================= comments ========================= */
/*
Set percent leaf area inserted into contour
 */
/* ========================= declarations ========================= */
/*
type       parameter      i/o     description
---------- -------------- ------- ----------------------------------------*/
Panel_item item;          /* i    panel item                              */
int        value;         /* i    percent leaf insertion                  */
Event      *event;        /* i    pointer to event                        */

/* ========================= log ========================= */
/*
return status description
--------------- --------------------------------------------------------- date      comments
--------- --------------------------------------------------------------
07/17/92  Creation - Jeremy Wong
 */
/* ================================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 int i;

i = x_objects->beam;
 x_objects->leaf_area[i] = value;

fprintf(stderr, "mlc: mlc_leaf_area: value: %d\n", value);
}
```

```
/* ======================= include files ======================= */

/* ======================= function name ======================= */ void mlc_rotation_mlc(item, value, event)

/* ======================= comments ======================= */
/*
Rotate contour
 */
/* ======================= declarations ======================= */
/*
type       parameter    i/o      description
---------  -----------  -------  -------------------------------------*/
Panel_item item;        /* i     panel item                           */
int        value;       /* i     degrees to rotate                    */
Event      *event;      /* i     pointer to event                     */

/* ======================= log ======================= */
/*
return status description
--------------- ---------------------------------------------------- date     comments
-------- ----------------------------------------------------------
07/17/92 Creation - Jeremy Wong
 */
/* ================================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 int i, stat;
 double area;
 char str[80];
 void mlc_rotate(), mlc_area();

xv_set (x_objects->ip->win, FRAME_LEFT_FOOTER, "", NULL);
 if ( x_objects->stat == 0 ) {
    xv_set (x_objects->ip->win, FRAME_LEFT_FOOTER, "Load contour first",
            NULL);
    return;
 }

XClearWindow ((Display *) xv_get (x_objects->ip->canvas1, XV_DISPLAY),
               (Window) xv_get (canvas_paint_window(
                                     x_objects->ip->canvas1), XV_XID));
 XFlush ((Display *) xv_get (x_objects->ip->canvas1, XV_DISPLAY));

/*mlc_rotate (x_objects, value);*/ x_objects->stat = 0;
 stat = mlc_disp_cont (x_objects);
 if ( stat != 1 ) {
    xv_set (x_objects->ip->win, FRAME_LEFT_FOOTER,
            "Cannot display contour", NULL);
    return;
 }
```

```
  stat = MLCfit (x_objects->points, x_objects->npoints);
  if ( stat == 0 ) {
     xv_set (x_objects->ip->win, FRAME_LEFT_FOOTER,
             "Contour does not fit in mlc", NULL);
     /*return;*/
  }
  x_objects->stat = 1;

/*
   find intersection points of leaves and contour points
*/

/*xv_set (x_objects->ip->win, FRAME_LEFT_FOOTER, "", NULL);*/
  i = x_objects->beam;
  x_objects->rotate_angle[i] = mlc_ext_int_rot (value);
  stat = MLCleaves (x_objects->points, x_objects->npoints,
                    x_objects->rotate_angle[i], x_objects->leaf_area[i],
                    x_objects->average[i], x_objects->gpt_left[i],
                    x_objects->gpt_right[i]);
  if ( stat != 1 ) {
     xv_set (x_objects->ip->win, FRAME_LEFT_FOOTER,"Cannot position mlc",
             NULL);
     return;
  }
  x_objects->stat_leaf[i] = 1;

/*
   check for small contour that fits between 2 leaves
*/ stat = MLCcheck (x_objects->points, x_objects->npoints,
                   x_objects->gpt_left[i], x_objects->gpt_right[i]);
  if ( stat != 1 ) {
     xv_set (x_objects->ip->win, FRAME_LEFT_FOOTER,"Cannot position mlc",
             NULL);
     return;
  }

/*
   display mlc
*/ stat = MLCarea (x_objects->points, x_objects->npoints,
                  x_objects->rotate_angle[i], x_objects->gpt_left[i],
                  x_objects->gpt_right[i], &area);
  mlc_area (x_objects);
  sprintf (str, "Area: %.2f", area);
  xv_set (x_objects->ip->win, FRAME_LEFT_FOOTER, str, NULL);

stat = mlc_disp_mlc (x_objects);
  if ( stat != 1 ) {
     xv_set (x_objects->ip->win, FRAME_LEFT_FOOTER, "Cannot display mlc",
             NULL);
     return;
  }
  x_objects->stat = 2;

fprintf(stderr, "mlc: mlc_rotation_mlc: value: %d\n", value);
}
```

```
/* ===================== include files ===================== */
/* ===================== function name ===================== */ void mlc_interval_mlc(item, value, event)

/* ======================= comments ======================= */
/*
Set interval of rotation for optimize mlc
 */
/* ====================== declarations ===================== */
/*
type        parameter    i/o      description
---------   ----------   ------   ----------------------------------------*/
Panel_item  item;        /* i     panel item                              */
int         value;       /* i     interval of rotation                    */
Event       *event;      /* i     pointer to event                        */

/* ========================== log ========================== */
/*
return status description
--------------   ----------------------------------------------- date       comments
--------   -----------------------------------------------
07/17/92   Creation - Jeremy Wong
 */
/* ========================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);

x_objects->interval = value;

fprintf(stderr, "mlc: mlc_interval_mlc: value %d\n", value);
}

/* ===================== include files ===================== */
/* ===================== function name ===================== */ void mlc_average_mlc(item, value, event)

/* ======================= comments ======================= */
/*
Set number of leaf intervals for average intersection
 */
/* ====================== declarations ===================== */
/*
type        parameter    i/o      description
---------   ----------   ------   ----------------------------------------*/
Panel_item  item;        /* i     panel item                              */
```

```
int      value;    /* i    leaf average                    */
Event    *event;   /* i    pointer to event                */

/* ========================= log ========================= */
/*
return status description
-------------- ------------------------------------------ date     comments
-------- ------------------------------------------
07/17/92 Creation - Jeremy Wong
*/
/* ======================================================= */

{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 int i;

i = x_objects->beam;
 if ( value == 0 )
    x_objects->average[i] = 3;
 else if ( value == 1 )
    x_objects->average[i] = 5;

fprintf(stderr, "mlc: mlc_average_mlc: value %d\n", value);
}

/* ========================= include files ========================= */

/* ========================= function name ========================= */ void mlc_tshift_mlc(item, event)

/* ========================= comments ========================= */
/*
Shift contour to the top
*/
/* ========================= declarations ========================= */
/*
type       parameter    i/o    description
---------- ------------ ------ ---------------------------------------*/
Panel_item item;       /* i    panel item                         */
Event      *event;     /* i    pointer to event                   */

/* ========================= log ========================= */
/*
return status description
-------------- ------------------------------------------ date     comments
-------- ------------------------------------------
07/17/92 Creation - Jeremy Wong
*/
/* ======================================================= */
```

```
{
 mlc_win_objects  *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 void mlc_translate(), mlc_translation();

switch ( event_action (event) ) {
    case ACTION_SELECT:
       if (event_is_up(event)) {
          x_objects->shift_y += 0.01;
          mlc_translate (x_objects, 0., 0.01); /* 0.1 mm */
          mlc_translation (x_objects);
       }
       break;
    case ACTION_MENU:
       if (event_is_up(event)) {
          x_objects->shift_y += 0.1;
          mlc_translate (x_objects, 0., 0.1); /* 1 mm */
          mlc_translation (x_objects);
       }
       break;
 }
 fputs("mlc: mlc_tshift_mlc\n", stderr);
 panel_default_handle_event(item,event);
}

/* ======================== include files ======================== */

/* ======================== function name ======================== */ void mlc_bshift_mlc(item, event)

/* ======================== comments ======================== */
/*
Shift contour to the bottom
*/
/* ======================== declarations ======================== */
/*
type      parameter     i/o      description
--------- ------------- -------- ----------------------------------------*/
Panel_item item;        /* i     panel item                              */
Event      *event;      /* i     pointer to event                        */

/* ======================== log ======================== */
/*
return status description
--------------- ---------------------------------------------------------- date     comments
-------- ----------------------------------------------------------------
07/17/92 Creation - Jeremy Wong
*/
/* =============================================================== */

{
 mlc_win_objects  *ip = (mlc_win_objects *) xv_get(item, XV_KEY_DATA,
INSTANCE);
```

```
   mlc_x_objects    *x_objects = (mlc_x_objects *) xv_get(ip->win,
XV_KEY_DATA, XINSTANCE);
 void mlc_translate(), mlc_translation();

switch ( event_action (event) ) {
     case ACTION_SELECT:
        if (event_is_up(event)) {
           x_objects->shift_y += -0.01;
           mlc_translate (x_objects, 0., -0.01); /* 0.1 mm */
           mlc_translation (x_objects);
        }
        break;
     case ACTION_MENU:
        if (event_is_up(event)) {
           x_objects->shift_y += -0.1;
           mlc_translate (x_objects, 0., -0.1); /* 1 mm */
           mlc_translation (x_objects);
        }
        break;
  }
 fputs("mlc: mlc_bshift_mlc\n", stderr);
 panel_default_handle_event(item,event);
}

/* ========================= include files ========================= */

/* ========================= function name ========================= */ void mlc_rshift_mlc(item, event)

/* ========================= comments ========================= */
/*
Shift contour to the right
*/
/* ========================= declarations ========================= */
/*
type        parameter    i/o       description
---------   -----------  --------  ------------------------------------*/
Panel_item  item;        /* i      panel item                          */
Event       *event;      /* i      pointer to event                    */

/* ========================= log ========================= */
/*
return status description
--------------  ------------------------------------------------------ date      comments
--------  ------------------------------------------------------------
07/17/92  Creation - Jeremy Wong
*/
/* ================================================================== */

{
 mlc_win_objects *ip = (mlc_win_objects *) xv_get(item, XV_KEY_DATA,
INSTANCE);
 mlc_x_objects    *x_objects = (mlc_x_objects *) xv_get(ip->win,
XV_KEY_DATA, XINSTANCE);
 void mlc_translate(), mlc_translation();
```

```
   switch ( event_action (event) ) {
      case ACTION_SELECT:
         if (event_is_up(event)) {
            x_objects->shift_x += 0.01;
            mlc_translate (x_objects, 0.01, 0.); /* 0.1 mm */
            mlc_translation (x_objects);
         }
         break;
      case ACTION_MENU:
         if (event_is_up(event)) {
            x_objects->shift_x += 0.1;
            mlc_translate (x_objects, 0.1, 0.); /* 1 mm */
            mlc_translation (x_objects);
         }
         break;
   }
   fputs("mlc: mlc_rshift_mlc\n", stderr);
   panel_default_handle_event(item,event);
}

/* ====================== include files ======================= */

/* ====================== function name ======================= */ void mlc_lshift_mlc(item, event)

/* ========================== comments ======================== */
/*
Shift contour to the left
 */
/* ========================= declarations ===================== */
/*
type        parameter    i/o      description
---------   ------------ -------- ----------------------------------*/
Panel_item item;         /* i     panel item                        */
Event       *event;      /* i     pointer to event                  */

/* ========================== log ============================= */
/*
return status description
--------------- ----------------------------------------------------- date      comments
--------  --------
07/17/92  Creation - Jeremy Wong
 */
/* ============================================================ */

{
 mlc_win_objects *ip = (mlc_win_objects *) xv_get(item, XV_KEY_DATA,
INSTANCE);
 mlc_x_objects  *x_objects = (mlc_x_objects *) xv_get(ip->win,
XV_KEY_DATA, XINSTANCE);
 void mlc_translate(), mlc_translation();

switch ( event_action (event) ) {
    case ACTION_SELECT:
```

```
      if (event_is_up(event)) {
          x_objects->shift_x += -0.01;
          mlc_translate (x_objects, -0.01, 0.); /* 0.1 mm */
          mlc_translation (x_objects);
      }
      break;
    case ACTION_MENU:
      if (event_is_up(event)) {
          x_objects->shift_x += -0.1;
          mlc_translate (x_objects, -0.1, 0.); /* 1 mm */
          mlc_translation (x_objects);
      }
      break;
  }
  fputs("mlc: mlc_lshift_mlc\n", stderr);
  panel_default_handle_event(item,event);
}

/* ========================= include files ========================= */

/* ========================= function name ========================= */ void mlc_translation (x_objects)

/* ========================= comments ========================= */
/*
Shift contour to the top/bottom/right/left
 */
/* ========================= declarations ========================= */
/*
type        parameter       i/o       description
---------   ------------    ------    -------------------------------------*/
mlc_x_objects *x_objects;   /* i      mlc header                           */

/* ========================= log ========================= */
/*
return status description
--------------- --------------------------------------------------------- date      comments
--------  -------------------------------------------------------------
07/17/92  Creation - Jeremy Wong
 */
/* ================================================================ */

{
 int i, stat;
 double area;
 char str[80];
 void mlc_area();

xv_set (x_objects->ip->win, FRAME_LEFT_FOOTER, "", NULL);
 if ( x_objects->stat == 0 ) {
    xv_set (x_objects->ip->win, FRAME_LEFT_FOOTER, "Load contour first",
            NULL);
    return;
 }
```

```c
  XClearWindow ((Display *) xv_get (x_objects->ip->canvas1, XV_DISPLAY),
             (Window) xv_get (canvas_paint_window(
                                 x_objects->ip->canvas1), XV_XID));
  XFlush ((Display *) xv_get (x_objects->ip->canvas1, XV_DISPLAY));

x_objects->stat = 0;
  stat = mlc_disp_cont (x_objects);
  if ( stat != 1 ) {
     xv_set (x_objects->ip->win, FRAME_LEFT_FOOTER,
            "Cannot display contour", NULL);
     return;
  } stat = MLCfit (x_objects->points, x_objects->npoints);
  if ( stat == 0 ) {
     xv_set (x_objects->ip->win, FRAME_LEFT_FOOTER,
            "Contour does not fit in mlc", NULL);
     /*return;*/
  }
  x_objects->stat = 1;

/*
    find intersection points of leaves and contour points
*/

/*xv_set (x_objects->ip->win, FRAME_LEFT_FOOTER, "", NULL);*/
  i = x_objects->beam;
  stat = MLCleaves (x_objects->points, x_objects->npoints,
                    x_objects->rotate_angle[i], x_objects->leaf_area[i],
                    x_objects->average[i], x_objects->gpt_left[i],
                    x_objects->gpt_right[i]);
  if ( stat != 1 ) {
     xv_set (x_objects->ip->win, FRAME_LEFT_FOOTER,"Cannot position mlc",
            NULL);
     return;
  }
  x_objects->stat_leaf[i] = 1;

/*
   check for small contour that fits between 2 leaves
*/ stat = MLCcheck (x_objects->points, x_objects->npoints,
                   x_objects->gpt_left[i], x_objects->gpt_right[i]);
  if ( stat != 1 ) {
     xv_set (x_objects->ip->win, FRAME_LEFT_FOOTER,"Cannot position mlc",
            NULL);
     return;
  }

/*
   display mlc
*/ stat = MLCarea (x_objects->points, x_objects->npoints,
                  x_objects->rotate_angle[i], x_objects->gpt_left[i],
                  x_objects->gpt_right[i], &area);
  mlc_area (x_objects);
  sprintf (str, "Area: %.2f", area);
  xv_set (x_objects->ip->win, FRAME_LEFT_FOOTER, str, NULL);
```

```
  stat = mlc_disp_mlc (x_objects);
  if ( stat != 1 ) {
     xv_set (x_objects->ip->win, FRAME_LEFT_FOOTER, "Cannot display mlc",
             NULL);
     return;
  }
  x_objects->stat = 2;

fputs("mlc: mlc_translation\n", stderr);
}

/* ========================= include files ========================= */

/* ========================= function name ========================= */ void mlc_repaint_mlc(canvas, paint_window, rects)

/* ========================= comments ========================= */
 /*
Display contour and mlc
 */
 /* ========================= declarations ========================= */
 /*
type       parameter     i/o     description
---------- ------------- ------- --------------------------------------*/
Canvas     canvas;       /* i    window canvas                         */
Xv_window  paint_window; /* i    paint window                          */
Rectlist   *rects;       /* i    window rectangle                      */

/* ========================= log ========================= */
 /*
return status description
------------ ---------------------------------------------------------- date       comments
---------- ----------------------------------------------------------
07/17/92   Creation - Jeremy Wong
 */
 /* ================================================================= */

{
 mlc_win_objects *ip = (mlc_win_objects *) xv_get(canvas, XV_KEY_DATA,
INSTANCE);
 mlc_x_objects   *x_objects = (mlc_x_objects *) xv_get(ip->win,
XV_KEY_DATA, XINSTANCE);
 int i, stat;

i = x_objects->beam;
 if ( x_objects->stat != 0 ) {
    stat = mlc_disp_cont (x_objects);
    if ( x_objects->stat >= 2 ) {
       stat = mlc_disp_mlc (x_objects);
       /*if ( x_objects->stat_coll[i] )
          stat = mlc_disp_coll (x_objects);*/
    }
 }
```

```
 fputs("mlc: mlc_repaint_mlc\n", stderr);
}

/* ========================= include files ========================= */

/* ========================= function name ========================= */

Panel_setting mlc_load_text(item, event)

/* ========================= comments ========================= */
/*
Load contour file
 */
/* ========================= declarations ========================= */
/*
type        parameter      i/o     description
---------   -------------  ------  ---------------------------------------*/
Panel_item  item;          /* i    panel item                             */
Event       *event;        /* i    pointer to event                       */

/* ========================= log ========================= */
/*
return status description
--------------   --------------------------------------------------------- date     comments
-------- ---------------------------------------------------------------
07/17/92 Creation - Jeremy Wong
 */
/* ================================================================= */

{
 mlc_popup1_objects    *ip = (mlc_popup1_objects *) xv_get(item,
XV_KEY_DATA, INSTANCE);
 mlc_x_objects   *x_objects = (mlc_x_objects *) xv_get(ip->popup1,
XV_KEY_DATA, XINSTANCE);
 char *    value = (char *) xv_get(item, PANEL_VALUE);
 void mlc_input();

xv_set (x_objects->ip->win, FRAME_LEFT_FOOTER, "", NULL);
 mlc_input (x_objects);

fprintf(stderr, "mlc: mlc_load_text: value: %s\n", value);
 return panel_text_notify(item, event);
}

/* ========================= include files ========================= */

/* ========================= function name ========================= */ void mlc_load_file(item, event)

/* ========================= comments ========================= */
/*
Load contour file
 */
```

```
/* ===================== declarations ===================== */
/*
type        parameter       i/o      description
---------   -------------   -----    -----------------------------------------*/
Panel_item  item;           /* i     panel item                              */
Event       *event;         /* i     pointer to event                        */

/* ===================== log ===================== */
/*
return status description
--------------- ------------------------------------------------- date     comments
-------- -------------------------------------------------
07/17/92 Creation - Jeremy Wong
*/
/* ============================================================= */

{
 mlc_popup1_objects   *ip = (mlc_popup1_objects *) xv_get(item,
XV_KEY_DATA, INSTANCE);
 mlc_x_objects        *x_objects = (mlc_x_objects *) xv_get(ip->popup1,
XV_KEY_DATA, XINSTANCE);
 void mlc_input();

xv_set (x_objects->ip->win, FRAME_LEFT_FOOTER, "", NULL);
 mlc_input (x_objects);

fputs("mlc: mlc_load_file\n", stderr);
}

/* ===================== include files ===================== */
/* ===================== function name ===================== */

Panel_setting mlc_save_text(item, event)

/* ===================== comments ===================== */
/*
Save mlc leaf setting file
*/
/* ===================== declarations ===================== */
/*
type        parameter       i/o      description
---------   -------------   -----    -----------------------------------------*/
Panel_item  item;           /* i     panel item                              */
Event       *event;         /* i     pointer to event                        */

/* ===================== log ===================== */
/*
return status description
--------------- ------------------------------------------------- date     comments
-------- -------------------------------------------------
07/17/92 Creation - Jeremy Wong
*/
/* ============================================================= */
```

```
{
 mlc_popup2_objects    *ip = (mlc_popup2_objects *) xv_get(item,
XV_KEY_DATA, INSTANCE);
 mlc_x_objects    *x_objects = (mlc_x_objects *) xv_get(ip->popup2,
XV_KEY_DATA, XINSTANCE);
 char *    value = (char *) xv_get(item, PANEL_VALUE);
 void mlc_output();

xv_set (x_objects->ip->win, FRAME_LEFT_FOOTER, "", NULL);
 mlc_output (x_objects);

fprintf(stderr, "mlc: mlc_save_text: value: %s\n", value);
 return panel_text_notify(item, event);
}

/* ========================= include files ========================= */

/* ========================= function name ========================= */ void mlc_save_file(item, event)

/* ========================= comments ========================= */
/*
Save mlc leaf setting file
*/
/* ========================= declarations ========================= */
/*
type        parameter    i/o     description
----------  ------------ ------- ---------------------------------------*/
Panel_item item;        /* i     panel item                             */
Event      *event;      /* i     pointer to event                       */

/* ========================= log ========================= */
/*
return status description
--------------- ---------------------------------------------------- date     comments
-------- ----------------------------------------------------
07/17/92 Creation - Jeremy Wong
*/
/* ================================================================ */

{
 mlc_popup2_objects    *ip = (mlc_popup2_objects *) xv_get(item,
XV_KEY_DATA, INSTANCE);
 mlc_x_objects    *x_objects = (mlc_x_objects *) xv_get(ip->popup2,
XV_KEY_DATA, XINSTANCE);
 void mlc_output();

xv_set (x_objects->ip->win, FRAME_LEFT_FOOTER, "", NULL);
 mlc_output (x_objects);

fputs("mlc: mlc_save_file\n", stderr);
}
```

```
/* ========================= include files ========================= */

/* ========================= function name ========================= */ void mlc_rotate (x_objects, value)

/* ========================= comments ========================= */
/*
Rotate contour
 */
/* ========================= declarations ========================= */
/*
type        parameter      i/o       description
----------  -------------  --------  ---------------------------------*/
mlc_x_objects *x_objects;  /* i      mlc header                       */
int         value;         /* i      degrees to rotate                */

/* ========================= log ========================= */
/*
return status description
---------------------   --------------------------------------------- date        comments
---------   ---------------------------------------------
07/17/92    Creation - Jeremy Wong
 */
/* ========================================================== */

{
 int i;
 double rad, sin(), cos();
 void mlc_translate();

rad = value * (3.141592654 / 180.);
 for ( i = 0; i < x_objects->npoints; i++ ) {
    if ( value == 0 ) {
       x_objects->points[i].x = x_objects->save_points[i].x;
       x_objects->points[i].y = x_objects->save_points[i].y;
    }
    else {
       x_objects->points[i].x = (x_objects->save_points[i].x *
                                 cos (rad)) -
                                (x_objects->save_points[i].y *
                                 sin (rad));
       x_objects->points[i].y = (x_objects->save_points[i].x *
                                 sin (rad)) +
                                (x_objects->save_points[i].y *
                                 cos (rad));
    }
 }
 mlc_translate (x_objects, x_objects->shift_x, x_objects->shift_y);
 i = x_objects->beam;
 x_objects->rotate_angle[i] = value;

fputs("mlc: mlc_rotate\n", stderr);
}
```

```
/* ===================== include files ===================== */
/* ===================== function name ===================== */ void mlc_translate (x_objects, value_x, value_y)

/* ===================== comments ===================== */
/*
Translate contour
 */
/* ===================== declarations ===================== */
/*
type        parameter      i/o       description
---------   ------------   --------  ----------------------------------------*/
mlc_x_objects *x_objects;  /* i      mlc header                              */
double       value_x;      /* i      x translation                           */
double       value_y;      /* i      y translation                           */

/* ===================== log ===================== */
/*
return status description
---------------  ----------------------------------------------------- date       comments
---------  -----------------------------------------------------
07/17/92   Creation - Jeremy Wong
 */
/* ============================================================= */

{
 int i;

for ( i = 0; i < x_objects->npoints; i++ ) {
    x_objects->points[i].x = x_objects->points[i].x + value_x;
    x_objects->points[i].y = x_objects->points[i].y + value_y;
 } fputs("mlc: mlc_translate\n", stderr);
}

/* ===================== include files ===================== */
/* ===================== function name ===================== */ void mlc_input (x_objects)

/* ===================== comments ===================== */
/*
Load contour
 */
/* ===================== declarations ===================== */
/*
type        parameter      i/o       description
---------   ------------   --------  ----------------------------------------*/
mlc_x_objects *x_objects;  /* i      mlc header                              */

/* ===================== log ===================== */
/*
```

```
 return status description
 --------------  ------------------------------------------------- date     comments
 --------  -------------------------------------------------
 07/17/92  Creation - Jeremy Wong
 */
/* ==================================================================== */

{
 char *value = NULL, str[64];
 int stat, i, j;
 void mlc_list();

SYSbufinit (x_objects->infile, 0, sizeof (x_objects->infile));
 value = (char *) xv_get (x_objects->ip1->dir1, PANEL_VALUE);
 strcat (x_objects->infile, value);
 if ( strcmp (value, "") != 0 )
    strcat (x_objects->infile, "/");

value = (char *) xv_get (x_objects->ip1->file1, PANEL_VALUE);
 strcat (x_objects->infile, value);
 if ( strcmp (value, "") == 0 )
    return;

SYSbufinit (x_objects->lname, 0, sizeof (x_objects->lname));
 SYSbufinit (x_objects->fname, 0, sizeof (x_objects->fname));
 SYSbufinit (x_objects->pid, 0, sizeof (x_objects->pid));
 value = (char *) xv_get (x_objects->ip1->lname, PANEL_VALUE);
 if ( strcmp (value, "") != 0 )
    strcat (x_objects->lname, value);
 value = (char *) xv_get (x_objects->ip1->fname, PANEL_VALUE);
 if ( strcmp (value, "") != 0 )
    strcat (x_objects->fname, value);
 value = (char *) xv_get (x_objects->ip1->pid, PANEL_VALUE);
 if ( strcmp (value, "") != 0 )
    strcat (x_objects->pid, value);

XClearWindow ((Display *) xv_get (x_objects->ip->canvas1, XV_DISPLAY),
               (Window) xv_get (canvas_paint_window(
                                   x_objects->ip->canvas1), XV_XID));
 XFlush ((Display *) xv_get (x_objects->ip->canvas1, XV_DISPLAY));

x_objects->ngantry = 0;
 x_objects->npoints = 0;
 x_objects->save_npoints = 0;
 if ( x_objects->points != NULL )
    free (x_objects->points);
 if ( x_objects->save_points != NULL )
    free (x_objects->save_points);
 x_objects->points = NULL;
 x_objects->save_points = NULL;
 for ( i = 0; i < NGANTRY; i++ ) {
    x_objects->gantry[i] = 0;
    x_objects->ngpoints[i] = 0;
    if ( x_objects->gpoints[i] != NULL )
       free (x_objects->gpoints[i]);
    x_objects->gpoints[i] = NULL;

for ( j = 0; j < (NLEAF-1); j++ ) {
```

```c
      x_objects->gpt_left[i][j].x = 0.;
      x_objects->gpt_right[i][j].x = 0.;
   } x_objects->stat_leaf[i] = 0;
   x_objects->stat_coll[i] = 0;
   x_objects->rotate_angle[i] = -90;
   x_objects->leaf_area[i] = 50;
   x_objects->average[i] = 5;
   x_objects->x1[i] = 0.;
   x_objects->x2[i] = 0.;
   x_objects->y1[i] = 0.;
   x_objects->y2[i] = 0.;
   SYSbufinit (x_objects->field[i], 0, FIELDNAME);
}
x_objects->stat = 0;

stat = MLCinput (x_objects->infile, x_objects->gantry,
                 &x_objects->ngantry, x_objects->gpoints,
                 x_objects->ngpoints, x_objects->field);
if ( stat != 1 ) {
   xv_set (x_objects->ip->win, FRAME_LEFT_FOOTER,
           "Cannot open contour file", NULL);
   return;
} mlc_list (x_objects);

SYSbufinit (x_objects->outfile, 0, sizeof (x_objects->outfile));
value = (char *) xv_get (x_objects->ip1->dir3, PANEL_VALUE);
strcat (x_objects->outfile, value);
if ( strcmp (value, "") != 0 )
   strcat (x_objects->outfile, "/");

value = (char *) xv_get (x_objects->ip1->file3, PANEL_VALUE);
strcat (x_objects->outfile, value);
if ( strcmp (value, "") != 0 ) {
   stat = MLCinmlc (x_objects->outfile, x_objects->ngantry,
                    x_objects->gpt_left, x_objects->gpt_right,
                    x_objects->rotate_angle, x_objects->stat_leaf,
                    x_objects->lname, x_objects->fname,
                    x_objects->pid);
   if ( stat != 1 ) {
      xv_set (x_objects->ip->win, FRAME_LEFT_FOOTER,
              "Cannot open MLC file", NULL);
      return;
   } stat = MLCinleaf (x_objects->outfile, x_objects->ngantry,
                     x_objects->leaf_area, x_objects->average);
   if ( stat != 1 ) {
      xv_set (x_objects->ip->win, FRAME_LEFT_FOOTER,
              "Cannot open MLC leaf area file", NULL);
      return;
   }
} x_objects->shift_x = 0.;
x_objects->shift_y = 0.;
xv_set (x_objects->ip1->popup1, FRAME_CMD_PUSHPIN_IN, FALSE, NULL);
```

```c
    xv_set (x_objects->ip1->popup1, XV_SHOW, FALSE, NULL);
    xv_set (x_objects->ip->rotate, PANEL_VALUE, 0, NULL);

SYSbufinit (str, 0, sizeof (str));
    strcat (str, x_objects->lname);
    if ( (strcmp (x_objects->lname, "") != 0) &&
         (strcmp (x_objects->fname, "") != 0) )
        strcat (str, ", ");
    strcat (str, x_objects->fname);
    strcat (str, " ");
    strcat (str, x_objects->pid);
    xv_set (x_objects->ip->win, FRAME_RIGHT_FOOTER, str, NULL);
    fputs("mlc: mlc_input\n", stderr);
}

/* ========================= include files ========================= */

/* ========================= function name ========================= */ void mlc_output (x_objects)

/* ========================= comments ========================= */
/*
Save mlc leaf setting file
*/
/* ========================= declarations ========================= */
/*
type         parameter    i/o       description
---------    -----------  --------  ------------------------------------*/
mlc_x_objects *x_objects; /* i   mlc header                             */

/* ========================= log ========================= */
/*
return status description
--------------  ------------------------------------------------------ date     comments
-------- ------------------------------------------------------------
07/17/92 Creation - Jeremy Wong
*/
/* ========================================================= */

{
    char *value = NULL;
    int stat, i;

SYSbufinit (x_objects->outfile, 0, sizeof (x_objects->outfile));
    value = (char *) xv_get (x_objects->ip2->dir2, PANEL_VALUE);
    strcat (x_objects->outfile, value);
    if ( strcmp (value, "") != 0 )
        strcat (x_objects->outfile, "/");

value = (char *) xv_get (x_objects->ip2->file2, PANEL_VALUE);
    strcat (x_objects->outfile, value);
    if ( strcmp (value, "") == 0 )
        return;

stat = MLCoutput (x_objects->outfile, x_objects->ngantry,
```

```
                    x_objects->gantry, x_objects->gpt_left,
                    x_objects->gpt_right, x_objects->rotate_angle,
                    x_objects->shift_x, x_objects->shift_y,
                    x_objects->field, x_objects->lname,
                    x_objects->fname, x_objects->pid);
    if ( stat != 1 ) {
       xv_set (x_objects->ip->win, FRAME_LEFT_FOOTER, "Cannot save file",
              NULL);
       return;
    }

/* output current beam */
    i = x_objects->beam;
    stat = MLCout (x_objects->outfile, x_objects->ngantry, i,
                   x_objects->gantry, x_objects->gpt_left,
                   x_objects->gpt_right, x_objects->rotate_angle,
                   x_objects->shift_x, x_objects->shift_y,
                   x_objects->field, x_objects->lname,
                   x_objects->fname, x_objects->pid);

stat = MLCoutleaf (x_objects->outfile, x_objects->ngantry,
                       x_objects->leaf_area, x_objects->average,
                       x_objects->lname, x_objects->fname, x_objects->pid);
    if ( stat != 1 ) {
       xv_set (x_objects->ip->win, FRAME_LEFT_FOOTER, "Cannot save file",
              NULL);
       return;
    }
    x_objects->stat = 3;

xv_set (x_objects->ip2->popup2, FRAME_CMD_PUSHPIN_IN, FALSE, NULL);
    xv_set (x_objects->ip2->popup2, XV_SHOW, FALSE, NULL);
    fputs("mlc: mlc_output\n", stderr);
 }

/* ========================= include files ========================= */

/* ========================= function name ========================= */ void mlc_list (x_objects)

/* ========================= comments ========================= */
/*
Create list of gantry angles to select
 */
/* ========================= declarations ========================= */
/*
type       parameter    i/o      description
---------  -----------  -------  ----------------------------------------*/
mlc_x_objects *x_objects; /* i   mlc header                              */

/* ========================= log ========================= */
/*
return status description
--------------  ---------------------------------------------------------- date       comments
--------   ----------------------------------------------------------
```

```
07/17/92  Creation - Jeremy Wong
 */
/* =================================================================== */

{
 int i;
 char str[160];
 Xv_Font font;

font = (Xv_Font) xv_find (x_objects->ip->win,FONT,
                           FONT_FAMILY, FONT_FAMILY_LUCIDA_FIXEDWIDTH,
                           FONT_STYLE,  FONT_STYLE_NORMAL,
                           NULL);

xv_set (x_objects->ip->list_mlc, PANEL_LIST_SELECT, 0, TRUE, NULL);
 i = xv_get (x_objects->ip->list_mlc, PANEL_LIST_NROWS);
 xv_set (x_objects->ip->list_mlc, PANEL_LIST_DELETE_ROWS, 0, i, NULL);
 xv_set (x_objects->ip->list_mlc, XV_SHOW, FALSE, NULL);

for ( i = 0; i < x_objects->ngantry; i++ ) {
    SYSbufinit (str, 0, sizeof (str));
    sprintf (str, " %2d                %-4d", i+1,x_objects->gantry[i]);
    xv_set (x_objects->ip->list_mlc,
            PANEL_LIST_INSERT, i,
            PANEL_LIST_STRING, i, str,
            PANEL_LIST_CLIENT_DATA, i, i,
            PANEL_LIST_FONT, i, font,
            NULL);
 }
 xv_set (x_objects->ip->list_mlc, XV_SHOW, TRUE, NULL);

fputs("mlc: mlc_list\n", stderr);
}

/* ======================== include files ======================== */

/* ======================== function name ======================== */ void mlc_pt_pix (pt, x, y)

/* ========================= comments ========================= */
/*
Convert actual to pixel coordinates
 */
/* ========================= declarations ========================= */
/*
type       parameter      i/o      description
--------   -------------  -------  ----------------------------------------*/
point      *pt;           /* i     actual coordinates                      */
int        *x;            /* o     pixel x coordinate                      */
int        *y;            /* o     pixel y coordinate                      */

/* ============================ log ============================ */
/*
return status description
--------------   ------------------------------------------------- date      comments
```

```
--------  ------------------------------------------------------------
07/17/92  Creation - Jeremy Wong
 */
/* ================================================================ */

{
/*
 *x = nint ((20. * pt->x) + 425.);
 *y = nint ((-20. * pt->y) + 285.);
*/
 *x = nint ((100. * pt->x) + 300.);
 *y = nint ((-100. * pt->y) + 300.);
}

/* ======================= include files ======================= */

/* ======================= function name ======================= */ void mlc_pix_pt (pt, x, y)

/* ========================= comments ========================= */
/*
Convert pixel to actual coordinates
 */
/* ========================= declarations ========================= */
/*
type        parameter     i/o        description
---------   ------------  ----       ---------------------------------*/
point       *pt;          /* o       actual coordinates               */
int         x;            /* i       pixel x coordinate               */
int         y;            /* i       pixel y coordinate               */

/* ============================ log ============================ */
/*
return status description

--------    ------------------------------------------------------------ date        comments
--------    ------------------------------------------------------------
07/17/92    Creation - Jeremy Wong
 */
/* ================================================================ */

{
/*
 pt->x = (x - 425.) / 20.;
 pt->y = -1. * ((y - 285.) / 20.);
*/
 pt->x = (x - 300.) / 100.;
 pt->y = -1. * ((y - 300.) / 100.);
}

/* ======================= include files ======================= */

/* ======================= function name ======================= */
```

```
int mlc_disp_cont (x_objects)

/* ============================ comments ============================ */
/*
Display contour
 */
/* ============================ declarations ============================ */
/*
type       parameter    i/o     description
---------- ------------ ------- ------------------------------------------*/
mlc_x_objects *x_objects; /* i  mlc header                                */

/* ============================ log ============================ */
/*
return status description
---------------- ----------------------------------------------------- date     comments
-------- -----------------------------------------------------------
07/17/92 Creation - Jeremy Wong
 */
/* ============================================================ */

{
 Canvas canvas;
 Display *dpy;
 Window win;
 GC gc;
 XGCValues gc_val;
 int wd, ht, x, y, i;
 XPoint *pts = NULL;

canvas = x_objects->ip->canvas1;
 wd = xv_get (canvas, CANVAS_WIDTH);
 ht = xv_get (canvas, CANVAS_HEIGHT);
 dpy = (Display *) xv_get (canvas, XV_DISPLAY);
 win = (Window) xv_get (canvas_paint_window (canvas), XV_XID);
 gc = XCreateGC (dpy, win, NULL, &gc_val);
 XSetFunction (dpy, gc, GXcopy);
 XSetForeground (dpy, gc, x_objects->mlc_colors[5].pixel);

if ( x_objects->pmap != NULL )
    XFreePixmap (dpy, x_objects->pmap);
 x_objects->pmap = XCreatePixmap (dpy, XDefaultRootWindow (dpy, 0), wd,
                                  ht, 8);

if ( x_objects->npoints > 0 ) {
    pts = (XPoint *) malloc (sizeof (XPoint) * x_objects->npoints);
    for ( i = 0; i < x_objects->npoints; i++ ) {
       mlc_pt_pix (&x_objects->points[i], &x, &y);
       pts[i].x = x;
       pts[i].y = y;
    }
    XFillPolygon (dpy, win, gc, pts, x_objects->npoints, Convex,
                  CoordModeOrigin);
    free (pts);
 }
 XCopyArea (dpy, win, x_objects->pmap, gc, 0, 0, wd, ht, 0, 0);
 XFreeGC (dpy, gc);
```

```
 fputs("mlc: mlc_disp_cont\n", stderr);
 return 1;
}

/* ======================== include files ======================== */

/* ======================== function name ======================== */ int mlc_disp_mlc (x_objects)

/* ========================== comments ========================== */
/*
Display mlc
*/
/* ======================== declarations ======================== */
/*
type         parameter    i/o       description
---------    -----------  -----     --------------------------------------*/
mlc_x_objects *x_objects; /* i  mlc header                                */

/* ============================ log ============================ */
/*
return status description
-----------              ------------------------------------------------ date     comments
-------- --------------------------------------------------------------
07/17/92 Creation - Jeremy Wong
*/
/* ============================================================== */

{
 Canvas canvas;
 Display *dpy;
 Window win;
 GC gc;
 XFontStruct *font;
 XGCValues gc_val;
 point pt1, pt2, pt3, pt4, pta, ptb, ptc, ptd;
 int x1, y1, x2, y2, x3, y3, x4, y4, i, j, dir, asc, des, ht;
 char string[16];
 XPoint pts[5];
 XCharStruct overall;
 point mlc_rot();

canvas = x_objects->ip->canvas1;
 dpy = (Display *) xv_get (canvas, XV_DISPLAY);
 win = (Window) xv_get (canvas_paint_window (canvas), XV_XID);
 font = XLoadQueryFont (dpy, "fixed");
 gc_val.font = font->fid;
 gc = XCreateGC (dpy, win, GCFont, &gc_val);
 XSetFunction (dpy, gc, GXcopy);
 XSetForeground (dpy, gc, x_objects->mlc_colors[1].pixel);

SYSbufinit (string, 0, sizeof (string));
 strcat (string, "0123456789");
 XQueryTextExtents (dpy, font->fid, string, strlen (string), &dir, &asc,
                    &des, &overall);
```

```
  ht = asc + des;
/*

*/
  SYSbufinit (string, 0, sizeof (string));
  sprintf (string, "%s", "Gantry");
  x1 = 283;
  y1 = 10;
  XDrawString (dpy, win, gc, x1, y1, string, strlen (string));

SYSbufinit (string, 0, sizeof (string));
  sprintf (string, "%s", "Table");
  x1 = 286;
  y1 = 595;
  XDrawString (dpy, win, gc, x1, y1, string, strlen (string));

j = x_objects->beam;
  pt1.y = MINLEAFy;
  pt2.y = MINLEAFy + INCRLEAF;
  for ( i = 0; i < (NLEAF-1); i++ ) {
     pt1.x = MINLEAFx;
     pt2.x = x_objects->gpt_left[j][i].x;
     pt3.x = pt1.x;
     pt3.y = pt2.y;
     pt4.x = pt2.x;
     pt4.y = pt1.y;
     pta = mlc_rot (x_objects->rotate_angle[j], pt1);
     ptb = mlc_rot (x_objects->rotate_angle[j], pt2);
     ptc = mlc_rot (x_objects->rotate_angle[j], pt3);
     ptd = mlc_rot (x_objects->rotate_angle[j], pt4);
     mlc_pt_pix (&pta, &x1, &y1);
     mlc_pt_pix (&ptb, &x2, &y2);
     mlc_pt_pix (&ptc, &x3, &y3);
     mlc_pt_pix (&ptd, &x4, &y4);
     /*if ( i != 0 )
          y1 -= 1;*/
     pts[0].x = x1;
     pts[0].y = y1;
     pts[1].x = x3;
     pts[1].y = y3;
     pts[2].x = x2;
     pts[2].y = y2;
     pts[3].x = x4;
     pts[3].y = y4;
     pts[4].x = x1;
     pts[4].y = y1;
     XSetForeground (dpy, gc, x_objects->mlc_colors[1].pixel);
     XDrawLines (dpy, win, gc, pts, 5, CoordModeOrigin);

pt3.x = pt2.x - 0.3;
     pt3.y = ((pt1.y + pt2.y) / 2.) /*- ((ht / 2.) / 100.)*/;
     pta = mlc_rot (x_objects->rotate_angle[j], pt3);
     mlc_pt_pix (&pta, &x1, &y1);
     SYSbufinit (string, 0, sizeof (string));
     sprintf (string, "%2dA", i+1);
     XDrawString (dpy, win, gc, x1, y1, string, strlen (string));

pt3.x = x_objects->gpt_left[j][i].x - 0.2;
```

```
pt4.x = x_objects->gpt_left[j][i].x - 0.2;
pt3.y = pt1.y;
pt4.y = pt2.y;
pta = mlc_rot (x_objects->rotate_angle[j], pt3);
ptb = mlc_rot (x_objects->rotate_angle[j], pt4);
mlc_pt_pix (&pta, &x1, &y1);
mlc_pt_pix (&ptb, &x2, &y2);
XSetForeground (dpy, gc, x_objects->mlc_colors[3].pixel);
XDrawLine (dpy, win, gc, x1, y1, x2, y2);

pt1.x = MAXLEAFx;
pt2.x = x_objects->gpt_right[j][i].x;
pt3.x = pt1.x;
pt3.y = pt2.y;
pt4.x = pt2.x;
pt4.y = pt1.y;
pta = mlc_rot (x_objects->rotate_angle[j], pt1);
ptb = mlc_rot (x_objects->rotate_angle[j], pt2);
ptc = mlc_rot (x_objects->rotate_angle[j], pt3);
ptd = mlc_rot (x_objects->rotate_angle[j], pt4);
mlc_pt_pix (&pta, &x1, &y1);
mlc_pt_pix (&ptb, &x2, &y2);
mlc_pt_pix (&ptc, &x3, &y3);
mlc_pt_pix (&ptd, &x4, &y4);
/*if ( i != 0 )
    y1 -= 1;*/
pts[0].x = x1;
pts[0].y = y1;
pts[1].x = x3;
pts[1].y = y3;
pts[2].x = x2;
pts[2].y = y2;
pts[3].x = x4;
pts[3].y = y4;
pts[4].x = x1;
pts[4].y = y1;
XSetForeground (dpy, gc, x_objects->mlc_colors[1].pixel);
XDrawLines (dpy, win, gc, pts, 5, CoordModeOrigin);

pt3.x = pt2.x + 0.3;
pt3.y = ((pt1.y + pt2.y) / 2.) /*- ((ht / 2.) / 100.)*/;
pta = mlc_rot (x_objects->rotate_angle[j], pt3);
mlc_pt_pix (&pta, &x1, &y1);
SYSbufinit (string, 0, sizeof (string));
sprintf (string, "%dB", i+1);
XDrawString (dpy, win, gc, x1, y1, string, strlen (string));

pt3.x = x_objects->gpt_right[j][i].x + 0.2;
pt4.x = x_objects->gpt_right[j][i].x + 0.2;
pt3.y = pt1.y;
pt4.y = pt2.y;
pta = mlc_rot (x_objects->rotate_angle[j], pt3);
ptb = mlc_rot (x_objects->rotate_angle[j], pt4);
mlc_pt_pix (&pta, &x1, &y1);
mlc_pt_pix (&ptb, &x2, &y2);
XSetForeground (dpy, gc, x_objects->mlc_colors[3].pixel);
XDrawLine (dpy, win, gc, x1, y1, x2, y2);

pt1.y += INCRLEAF;
pt2.y += INCRLEAF;
```

```
}
XFreeGC (dpy, gc);

fputs("mlc: mlc_disp_mlc\n", stderr);
return 1;
}

/* ===================== include files ===================== */
/* ===================== function name ===================== */ void mlc_show_message1 (x_objects, stat)

/* ===================== comments ===================== */
/*
Display/undisplay messages in mlc window
*/
/* ===================== declarations ===================== */
/*
type         parameter    i/o       description
---------    ----------   -------   -----------------------------------*/
mlc_x_objects *x_objects; /* i  mlc header                              */
int           stat;       /* i  0 - undisplay, 1 - display messages    */

/* ===================== log ===================== */
/*
return status description
------------- ------------------------------------------------------ date      comments
--------  ------------------------------------------------------
07/17/92  Creation - Jeremy Wong
*/
/* ===================== */

{ xv_set (x_objects->ip->adjust1, XV_SHOW, stat, NULL);
 xv_set (x_objects->ip->adjust2, XV_SHOW, stat, NULL);
 xv_set (x_objects->ip->adjust3, XV_SHOW, stat, NULL);

}

/* ===================== include files ===================== */
/* ===================== function name ===================== */ void mlc_show_button (x_objects, stat)

/* ===================== comments ===================== */
/*
Display/undisplay items in mlc window
*/
/* ===================== declarations ===================== */
/*
type         parameter    i/o       description
```

```
   ---------  -------------  --------  --------------------------------------*/
   mlc_x_objects *x_objects; /* i   mlc header                                */
   int       stat;       /* i   0 - undisplay, 1 - display items              */

/* ============================ log ============================ */
   /*
   return status description
   --------------  ----------------------------------------------------------- date      comments
   --------  -----------------------------------------------------------------
   07/17/92  Creation - Jeremy Wong
    */
   /* ================================================================= */

{ xv_set (x_objects->ip->load_contour, PANEL_INACTIVE, !stat, NULL);
    xv_set (x_objects->ip->draw_mlc, PANEL_INACTIVE, !stat, NULL);
    xv_set (x_objects->ip->adjust_mlc, PANEL_INACTIVE, !stat, NULL);
    xv_set (x_objects->ip->rotate, XV_SHOW, stat, NULL);
    xv_set (x_objects->ip->leaf_area, XV_SHOW, stat, NULL);
    xv_set (x_objects->ip->interval, XV_SHOW, stat, NULL);
    xv_set (x_objects->ip->average, XV_SHOW, stat, NULL);
    xv_set (x_objects->ip->list_mlc, PANEL_INACTIVE, !stat, NULL);
   /*
    xv_set (x_objects->ip->coll_set, PANEL_INACTIVE, !stat, NULL);
    xv_set (x_objects->ip->coll_edit, PANEL_INACTIVE, !stat, NULL);
   */
    xv_set (x_objects->ip->opt_mlc, PANEL_INACTIVE, !stat, NULL);
    xv_set (x_objects->ip->save_mlc, PANEL_INACTIVE, !stat, NULL);
    xv_set (x_objects->ip->exit_mlc, PANEL_INACTIVE, !stat, NULL);
   /*
    xv_set (x_objects->ip->lshift, PANEL_INACTIVE, !stat, NULL);
    xv_set (x_objects->ip->rshift, PANEL_INACTIVE, !stat, NULL);
    xv_set (x_objects->ip->tshift, PANEL_INACTIVE, !stat, NULL);
    xv_set (x_objects->ip->bshift, PANEL_INACTIVE, !stat, NULL);
    xv_set (x_objects->ip->shift, PANEL_INACTIVE, !stat, NULL);
   */

}

/* ===================== include files ===================== */

/* ===================== function name ===================== */ void mlc_adjust (window, event, arg)

/* ======================== comments ======================== */
   /*
   Adjust mlc manually
    */
   /* ======================= declarations ======================= */
   /*
   type       parameter    i/o      description
   ---------  -------------  --------  --------------------------------------*/
   Xv_window window;      /* i   mlc window                                   */
   Event     *event;      /* i   pointer to event                             */
```

```
Notify_arg arg;          /* i     argument                                      */
/* =========================== log =========================== */
/*
return status description
--------------- -------------------------------------------------- date      comments
--------- --------------------------------------------------
07/17/92  Creation - Jeremy Wong
*/
/* =========================================================== */

{
 mlc_x_objects   *x_objects = (mlc_x_objects *) xv_get(window,
XV_KEY_DATA, XINSTANCE);
 Canvas canvas;
 Display *dpy;
 Window win;
 GC gc;
 XGCValues gc_val;
 XPoint pts[5];
 int i, j, k, x, y, x1, y1, x2, y2, wd, ht, found, stat;
 double min_ln, max_ln, save_x;
 point pt, pt1, pt2;
 point mlc_inv_rot();

canvas = x_objects->ip->canvas1;
 dpy = (Display *) xv_get (canvas, XV_DISPLAY);
 win = (Window) xv_get (canvas_paint_window (canvas), XV_XID);
 gc = XCreateGC (dpy, win, NULL, &gc_val);
 XSetFunction (dpy, gc, GXcopy);

k = x_objects->beam;
 switch ( event_action (event) ) {
    case ACTION_SELECT: /* left leaf */
    case ACTION_MENU: /* right leaf */
       if ( event_is_up (event) ) {
          mlc_pix_pt (&pt1, event_x(event), event_y(event));
          pt = mlc_inv_rot (x_objects->rotate_angle[k], pt1);
          min_ln = MINLEAFy;
          max_ln = MINLEAFy + INCRLEAF;
          found = 0;
          for ( i = 0; (i < (NLEAF-1)) && (!found); i++ ) {
             if ( (pt.y >= min_ln) && (pt.y < max_ln) ) {
                found = 1;
                j = i;
             }
             else {
                min_ln += INCRLEAF;
                max_ln += INCRLEAF;
             }
          } if ( (pt.x >= MINLEAFx) && (pt.x <= MAXLEAFx) && found ) {
             found = 0;
             if ( event_action (event) == ACTION_SELECT ) {
                if (pt.x <= x_objects->gpt_right[k][j].x){
                   save_x = x_objects->gpt_left[k][j].x;
                   x_objects->gpt_left[k][j].x = pt.x;
```

```
            found = 1;
         }
      }
      else if ( event_action (event) == ACTION_MENU ) {
         if ( pt.x >= x_objects->gpt_left[k][j].x){
            save_x = x_objects->gpt_right[k][j].x;
            x_objects->gpt_right[k][j].x = pt.x;
            found = 1;
         }
      } if ( found ) {
         XClearWindow ((Display *)
                    xv_get (x_objects->ip->canvas1, XV_DISPLAY),
                       (Window) xv_get (canvas_paint_window(
                       x_objects->ip->canvas1), XV_XID));
         XFlush ((Display *) xv_get (x_objects->ip->canvas1,
                 XV_DISPLAY));
         mlc_repaint_mlc (canvas, canvas_paint_window(canvas),
                          NULL);
/*
         if ( event_action (event) == ACTION_SELECT )
            pt1.x = MINLEAFx - 0.05;
         else if ( event_action (event) == ACTION_MENU )
            pt1.x = MAXLEAFx + 0.05;
         pt2.x = save_x;
         found = 0;
         pt1.y = MINLEAFy;
         pt2.y = MINLEAFy + INCRLEAF;
         for ( i = 0; (i < (NLEAF-1)) && (!found); i++ ) {
            if ( i == j )
               found = 1;
            else {
               pt1.y += INCRLEAF;
               pt2.y += INCRLEAF;
            }
         }
         mlc_pt_pix (&pt1, &x1, &y1);
         mlc_pt_pix (&pt2, &x2, &y2);
         if ( j != 0 )
            y1 -= 1;

if ( event_action (event) == ACTION_SELECT ) {
            x = x1;
            y = y2;
         }
         else if ( event_action (event) == ACTION_MENU ) {
            x = x2;
            y = y2;
         }
         wd = abs (x2 - x1) + 1;
         ht = abs (y2 - y1) + 1;
         XCopyArea (dpy, x_objects->pmap, win, gc, x, y,
                    wd, ht, x, y);

if ( event_action (event) == ACTION_SELECT )
            pt2.x = x_objects->gpt_left[k][j].x;
         else if ( event_action (event) == ACTION_MENU )
            pt2.x = x_objects->gpt_right[k][j].x;
         mlc_pt_pix (&pt2, &x2, &y2);
```

```
                    pts[0].x = x1;
                    pts[0].y = y1;
                    pts[1].x = x1;
                    pts[1].y = y2;
                    pts[2].x = x2;
                    pts[2].y = y2;
                    pts[3].x = x2;
                    pts[3].y = y1;
                    pts[4].x = x1;
                    pts[4].y = y1;
                    XSetForeground (dpy, gc,x_objects->mlc_colors[1].pixel);
                    XDrawLines (dpy, win, gc, pts, 5, CoordModeOrigin);

if ( event_action (event) == ACTION_SELECT )
                       pt2.x = x_objects->gpt_right[k][j].x;
                    else if ( event_action (event) == ACTION_MENU )
                       pt2.x = x_objects->gpt_left[k][j].x;
                    mlc_pt_pix (&pt2, &x2, &y2);
                    XDrawLine (dpy, win, gc, x2, y1, x2, y2);
*/
                }
            }
        }
        break;
    case ACTION_ADJUST:
        if ( event_is_up (event) ) {
            xv_set (canvas_paint_window(x_objects->ip->canvas1),
                WIN_EVENT_PROC, NULL, NULL);
            mlc_show_message1 (x_objects, FALSE);
            mlc_show_button (x_objects, TRUE);
        }
        break;
    }
    XFreeGC (dpy, gc);

/*fputs("mlc: mlc_adjust\n", stderr);*/
}

/* ======================= include files ======================= */

/* ======================= function name ======================= */ void mlc_opt (x_objects)

/* ======================= comments ======================= */
/*
Optimize mlc by calculating area of overdose/underdose
*/
/* ======================= declarations ======================= */
/*
type        parameter    i/o     description
---------   -----------  -----   -----------------------------------
mlc_x_objects *x_objects; /* i   mlc header                         */

/* ======================= log ======================= */
/*
return status description
--------------  ------------------------------------------------------
```

```
date     comments
-------- ---------------------------------------------------------------
07/17/92 Creation - Jeremy Wong
 */
/* ================================================================== */

{
  int i, j, k, stat, num, num1, gantry_angle, gantry_angle1, coll_angle,
      coll_angle1, leaf_area, average, beam, rotate;
  double area, min_area, min_area1;
  char str[160], tmp[160];
  Xv_Font font;

xv_set (x_objects->ip3->optl1, PANEL_VALUE, "", NULL);
  xv_set (x_objects->ip3->optl2, PANEL_VALUE, "", NULL);
  xv_set (x_objects->ip3->optl3, PANEL_VALUE, "", NULL);

leaf_area = (int) xv_get (x_objects->ip->leaf_area, PANEL_VALUE);
  average = (int) xv_get (x_objects->ip->average, PANEL_VALUE);
  if ( average == 0 )
     average = 3;
  else if ( average == 1 )
     average = 5;
  i = xv_get (x_objects->ip3->optl_mlc, PANEL_LIST_NROWS);
  xv_set (x_objects->ip3->optl_mlc, PANEL_LIST_DELETE_ROWS, 0, i, NULL);
  font = (Xv_Font) xv_find (x_objects->ip->win, FONT,
                            FONT_FAMILY, FONT_FAMILY_LUCIDA_FIXEDWIDTH,
                            FONT_STYLE, FONT_STYLE_NORMAL,
                            NULL);

x_objects->shift_x = 0.;
  x_objects->shift_y = 0.;
  min_area1 = -1.;
  beam = x_objects->beam;
  for ( i = 0; i < x_objects->ngantry; i++ ) {
     rotate = x_objects->rotate_angle[i];
     min_area = -1.;
     x_objects->beam = i;
     for ( j = -90; j <= 270; j += x_objects->interval ) {
/* if ( ((j >= 0) && (j <= 90)) || ((j >= 270) && (j <= 360)) ) { */
        SYSbufinit (str, 0, sizeof (str));
        sprintf (str, "Finding area for beam: %d (%s), coll. angle: %d",
                 i+1, x_objects->field[i], mlc_int_ext_rot (j));
        xv_set (x_objects->ip->win, FRAME_LEFT_FOOTER, str, NULL);
        XFlush ((Display *) xv_get (x_objects->ip->win, XV_DISPLAY));

if ( x_objects->points != NULL ) {
           free (x_objects->points);
           x_objects->points = NULL;
        }
        if ( x_objects->save_points != NULL ) {
           free (x_objects->save_points);
           x_objects->save_points = NULL;
        } x_objects->npoints = x_objects->ngpoints[i];
        x_objects->save_npoints = x_objects->npoints;
        if ( x_objects->npoints > 0 ) {
           x_objects->points = (point *) malloc (sizeof (point) *
```

```
                                            x_objects->npoints);
    x_objects->save_points = (point *) malloc (sizeof (point) *
                                            x_objects->npoints);
}
for ( k = 0; k < x_objects->ngpoints[i]; k++ ) {
    x_objects->points[k] = x_objects->gpoints[i][k];
    x_objects->save_points[k] = x_objects->gpoints[i][k];
}

/*mlc_rotate (x_objects, j);*/ stat = MLCleaves (x_objects->points, x_objects->npoints, j,
                  leaf_area, average, x_objects->pt_left,
                  x_objects->pt_right);
if ( stat != 1 ) {
    xv_set (x_objects->ip->win,FRAME_LEFT_FOOTER,
            "Cannot position mlc", NULL);
    return;
} stat = MLCcheck (x_objects->points, x_objects->npoints,
                 x_objects->pt_left, x_objects->pt_right);
if ( stat != 1 ) {
    xv_set (x_objects->ip->win,FRAME_LEFT_FOOTER,
            "Cannot position mlc", NULL);
    return;
} stat = MLCarea (x_objects->points, x_objects->npoints, j,
                x_objects->pt_left, x_objects->pt_right,
                &area);
if ( stat != 1 ) {
    xv_set (x_objects->ip->win,FRAME_LEFT_FOOTER,
            "Cannot find area", NULL);
    return;
} if ( min_area == -1. ) {
    min_area = area;
    gantry_angle = x_objects->gantry[i];
    coll_angle = j;
}
else if ( area < min_area ) {
    min_area = area;
    gantry_angle = x_objects->gantry[i];
    coll_angle = j;
} if ( min_area1 == - 1. ) { /* not used */
    min_area1 = area;
    gantry_angle1 = x_objects->gantry[i];
    coll_angle1 = j;
    num1 = i;
}
else if ( area < min_area1 ) {
    min_area1 = area;
    gantry_angle1 = x_objects->gantry[i];
    coll_angle1 = j;
    num1 = i;
}
```

```
/* } */
    }
    x_objects->rotate_angle[i] = rotate;

SYSbufinit (str, 0, sizeof (str));
    SYSbufinit (tmp, 0, sizeof (tmp));
    sprintf (tmp, "%2d", i+1);
    strcat (str, tmp);
    strcat (str, "      ");
    SYSbufinit (tmp, 0, sizeof (tmp));
    sprintf (tmp, "%4d", gantry_angle);
    strcat (str, tmp);
    strcat (str, "        ");
    SYSbufinit (tmp, 0, sizeof (tmp));
    sprintf (tmp, "%4d", mlc_int_ext_rot (coll_angle));
    strcat (str, tmp);
    strcat (str, "        ");
    SYSbufinit (tmp, 0, sizeof (tmp));
    sprintf (tmp, "%.2f", min_area);
    strcat (str, tmp);

num = xv_get (x_objects->ip3->optl_mlc, PANEL_LIST_NROWS);
    xv_set (x_objects->ip3->optl_mlc,
            PANEL_LIST_INSERT, num,
            PANEL_LIST_STRING, num, str,
            PANEL_LIST_FONT, num, font,
            NULL);
    xv_set (x_objects->ip->win, FRAME_LEFT_FOOTER, "", NULL);
    XFlush ((Display *) xv_get (x_objects->ip->win, XV_DISPLAY));
} sprintf (str, "%.2f", min_area1);
xv_set (x_objects->ip3->optl1, PANEL_VALUE, str, NULL);
sprintf (str, "%d", gantry_angle1);
xv_set (x_objects->ip3->optl2, PANEL_VALUE, str, NULL);
sprintf (str, "%d", mlc_int_ext_rot (coll_angle1));
xv_set (x_objects->ip3->optl3, PANEL_VALUE, str, NULL);
sprintf (str, "%d", num1+1);
xv_set (x_objects->ip3->optl4, PANEL_VALUE, str, NULL);
xv_set (x_objects->ip3->popup3, FRAME_CMD_PUSHPIN_IN, TRUE, NULL);
xv_set (x_objects->ip3->popup3, XV_SHOW, TRUE, NULL);

x_objects->beam = beam;
i = x_objects->beam;
if ( x_objects->points != NULL ) {
    free (x_objects->points);
    x_objects->points = NULL;
}
if ( x_objects->save_points != NULL ) {
    free (x_objects->save_points);
    x_objects->save_points = NULL;
} x_objects->npoints = x_objects->ngpoints[i];
x_objects->save_npoints = x_objects->npoints;
if ( x_objects->npoints > 0 ) {
    x_objects->points = (point *) malloc (sizeof (point) *
                                          x_objects->npoints);
    x_objects->save_points = (point *) malloc (sizeof (point) *
                                               x_objects->npoints);
```

```c
    }
    for ( j = 0; j < x_objects->ngpoints[i]; j++ ) {
        x_objects->points[j] = x_objects->gpoints[i][j];
        x_objects->save_points[j] = x_objects->gpoints[i][j];
    }
    /*mlc_rotate (x_objects, x_objects->rotate_angle[i]);*/ mlc_show_button (x_objects, TRUE);
}

/* ========================= include files ========================= */

/* ========================= function name ========================= */ void mlc_area (x_objects)

/* ========================= comments ========================= */
/*
Display squares for calculating area of overdose/underdose
*/
/* ========================= declarations ========================= */
/*
type        parameter    i/o        description
---------   -----------  ---------  ------------------------------------*/
mlc_x_objects *x_objects; /* i   mlc header                             */

/* ========================= log ========================= */
/*
return status description
---------------  ------------------------------------------------------ date      comments
--------  ------------------------------------------------------------
07/17/92  Creation - Jeremy Wong
*/
/* ========================================================= */

{
    int i, j, found, num_row, num_col, x1, y1, x2, y2;
    point min_pt1, max_pt1, min_pt2, max_pt2, pta, ptb, ptc, ptd, pt, pt1,
          pt2;
    Canvas canvas;
    Display *dpy;
    Window win;
    GC gc;
    XGCValues gc_val;
    XPoint pts[2];
    double ceil();
    point mlc_rot(), mlc_inv_rot();

canvas = x_objects->ip->canvas1;
    dpy = (Display *) xv_get (canvas, XV_DISPLAY);
    win = (Window) xv_get (canvas_paint_window (canvas), XV_XID);
    gc = XCreateGC (dpy, win, NULL, &gc_val);
    XSetFunction (dpy, gc, GXcopy);
    XSetForeground (dpy, gc, x_objects->mlc_colors[2].pixel);

/*
```

```
    find bounding box of contour
*/ j = x_objects->beam;
min_pt1.x = x_objects->points[0].x;
max_pt1.x = x_objects->points[0].x;
for ( i = 1; i < x_objects->npoints; i++ ) {
   if ( x_objects->points[i].x < min_pt1.x )
      min_pt1.x = x_objects->points[i].x;
   if ( x_objects->points[i].x > max_pt1.x )
      max_pt1.x = x_objects->points[i].x;
} if ( min_pt1.x < MINLEAFx )
   min_pt1.x = MINLEAFx;
if ( max_pt1.x > MAXLEAFx )
   max_pt1.x = MAXLEAFx;

min_pt1.y = x_objects->points[0].y;
max_pt1.y = x_objects->points[0].y;
for ( i = 1; i < x_objects->npoints; i++ ) {
   if ( x_objects->points[i].y < min_pt1.y )
      min_pt1.y = x_objects->points[i].y;
   if ( x_objects->points[i].y > max_pt1.y )
      max_pt1.y = x_objects->points[i].y;
} if ( min_pt1.y < MINLEAFy )
   min_pt1.y = MINLEAFy;
if ( max_pt1.y > MAXLEAFy )
   max_pt1.y = MAXLEAFy;

pt.x = min_pt1.x;
pt.y = min_pt1.y;
pta = mlc_rot (x_objects->rotate_angle[j], pt);
pt.x = min_pt1.x;
pt.y = max_pt1.y;
ptb = mlc_rot (x_objects->rotate_angle[j], pt);
pt.x = max_pt1.x;
pt.y = max_pt1.y;
ptc = mlc_rot (x_objects->rotate_angle[j], pt);
pt.x = max_pt1.x;
pt.y = min_pt1.y;
ptd = mlc_rot (x_objects->rotate_angle[j], pt);

/*
   find bounding box of mlc
*/ found = 0;
pt1.y = MINLEAFy;
pt2.y = pt1.y + INCRLEAF;
for ( i = 0; i < (NLEAF - 1); i++ ) {
   if ( x_objects->gpt_left[j][i].x !=
        x_objects->gpt_right[j][i].x ) {
      if ( found == 0 ) {
         min_pt2.y = pt1.y;
         max_pt2.y = pt2.y;
         found = 1;
      }
```

```
            else
                max_pt2.y = pt2.y;
        } pt1.y += INCRLEAF;
        if ( i != (NLEAF - 3) )
            pt2.y += INCRLEAF;
        else
            pt2.y = MAXLEAFy;
    }
    if ( found == 0 ) return;

found = 0;
    for ( i = 0; i < (NLEAF - 1); i++ ) {
        if ( x_objects->gpt_left[j][i].x !=
             x_objects->gpt_right[j][i].x ) {
            if ( found == 0 ) {
                min_pt2.x = x_objects->gpt_left[j][i].x;
                max_pt2.x = x_objects->gpt_right[j][i].x;
                found = 1;
            }
            else {
                if ( x_objects->gpt_left[j][i].x < min_pt2.x )
                    min_pt2.x = x_objects->gpt_left[j][i].x;
                if ( x_objects->gpt_right[j][i].x > max_pt2.x )
                    max_pt2.x = x_objects->gpt_right[j][i].x;
            }
        }
    }

/*
    find bounding box of contour and mlc
*/ if ( min_pt2.x > pta.x )
        min_pt2.x = pta.x;
    if ( min_pt2.x > ptb.x )
        min_pt2.x = ptb.x;
    if ( min_pt2.x > ptc.x )
        min_pt2.x = ptc.x;
    if ( min_pt2.x > ptd.x )
        min_pt2.x = ptd.x;

if ( min_pt2.y > pta.y )
        min_pt2.y = pta.y;
    if ( min_pt2.y > ptb.y )
        min_pt2.y = ptb.y;
    if ( min_pt2.y > ptc.y )
        min_pt2.y = ptc.y;
    if ( min_pt2.y > ptd.y )
        min_pt2.y = ptd.y;

if ( max_pt2.x < pta.x )
        max_pt2.x = pta.x;
    if ( max_pt2.x < ptb.x )
        max_pt2.x = ptb.x;
    if ( max_pt2.x < ptc.x )
        max_pt2.x = ptc.x;
    if ( max_pt2.x < ptd.x )
        max_pt2.x = ptd.x;
```

```
   if ( max_pt2.y < pta.y )
      max_pt2.y = pta.y;
   if ( max_pt2.y < ptb.y )
      max_pt2.y = ptb.y;
   if ( max_pt2.y < ptc.y )
      max_pt2.y = ptc.y;
   if ( max_pt2.y < ptd.y )
      max_pt2.y = ptd.y;

/*
   display area squares
*/ num_col = (int) (ceil ((max_pt2.x - min_pt2.x) / INCRMLEAF));
   num_row = (int) (ceil ((max_pt2.y - min_pt2.y) / INCRMLEAF));

pt1.x = min_pt2.x;
   pt1.y = min_pt2.y;
   pt2.x = min_pt2.x;
   pt2.y = max_pt2.y;
   for ( i = 0; i <= num_col; i++ ) {
      pta = mlc_rot (x_objects->rotate_angle[j], pt1);
      ptb = mlc_rot (x_objects->rotate_angle[j], pt2);
      mlc_pt_pix (&pta, &x1, &y1);
      mlc_pt_pix (&ptb, &x2, &y2);
      pts[0].x = x1;
      pts[0].y = y1;
      pts[1].x = x2;
      pts[1].y = y2;
      XDrawLine (dpy, win, gc, pts[0].x, pts[0].y, pts[1].x, pts[1].y);

if ( i != (num_col - 1) )
         pt1.x += INCRMLEAF;
      else
         pt1.x = max_pt2.x;
      pt2.x = pt1.x;
   } pt1.x = min_pt2.x;
   pt1.y = min_pt2.y;
   pt2.x = max_pt2.x;
   pt2.y = min_pt2.y;
   for ( i = 0; i <= num_row; i++ ) {
      pta = mlc_rot (x_objects->rotate_angle[j], pt1);
      ptb = mlc_rot (x_objects->rotate_angle[j], pt2);
      mlc_pt_pix (&pta, &x1, &y1);
      mlc_pt_pix (&ptb, &x2, &y2);
      pts[0].x = x1;
      pts[0].y = y1;
      pts[1].x = x2;
      pts[1].y = y2;
      XDrawLine (dpy, win, gc, pts[0].x, pts[0].y, pts[1].x, pts[1].y);

if ( i != (num_row - 1) )
         pt1.y += INCRMLEAF;
      else
         pt1.y = max_pt2.y;
      pt2.y = pt1.y;
   }
```

}

```
/* ======================= include files ======================= */
/* ======================= function name ======================= */ point mlc_rot (value, pt)

/* ======================= comments ======================= */
/*
Rotate point clockwise by specified value
*/
/* ======================= declarations ======================= */
/*
type      parameter    i/o     description
--------- ------------ ------- ----------------------------------*/
int       value;       /* i    degrees to rotate                 */
point     pt;          /* i    point to rotate                   */

/* ======================= log ======================= */
/*
return status description
------------- ---------------------------------------------------- date      comments
--------- ----------------------------------------------------
07/17/92  Creation - Jeremy Wong
*/
/* ============================================================ */

{
 double rad, sin(), cos();
 point p;

rad = value * (3.141592654 / 180.);
 if ( value == 0 ) {
    p.x = pt.x;
    p.y = pt.y;
 }
 else {
    p.x = (pt.x * cos (rad)) - (pt.y * sin (rad));
    p.y = (pt.x * sin (rad)) + (pt.y * cos (rad));
 } return p;
}

/* ======================= include files ======================= */
/* ======================= function name ======================= */ point mlc_inv_rot (value, pt)

/* ======================= comments ======================= */
/*
Rotate point counter-clockwise by specified value
```

```
 */
/* ===================== declarations ===================== */
/*
type      parameter    i/o      description
--------- ------------ -------- -------------------------------------------*/
int       value;       /* i     degrees to rotate                          */
point     pt;          /* i     point to rotate                            */

/* ========================== log ========================== */
/*
return status description
---------------- ------------------------------------------------ date      comments
--------- -----------------------------------------------------
07/17/92  Creation - Jeremy Wong
 */
/* ========================================================= */

{
 double rad, sin(), cos();
 point p;

rad = value * (3.141592654 / 180.);
 if ( value == 0 ) {
    p.x = pt.x;
    p.y = pt.y;
 }
 else {
    p.x = (pt.x * cos (rad)) + (pt.y * sin (rad));
    p.y = (pt.x * -1. * sin (rad)) + (pt.y * cos (rad));
 } return p;
}

/* ===================== include files ===================== */

/* ===================== function name ===================== */ int mlc_int_ext_rot (value)

/* ========================= comments ====================== */
/*
Transform rotation from internal to external degrees
 */
/* ===================== declarations ====================== */
/*
type      parameter    i/o      description
--------- ------------ -------- -------------------------------------------*/
int       value;       /* i     degrees to transform                       */

/* ========================== log ========================== */
/*
return status description
---------------- ------------------------------------------------ date      comments
```

```
--------  ----------------------------------------------------------
07/17/92  Creation - Jeremy Wong
 */
/* ================================================================ */

{ return value + 90;

}

/* ====================== include files ====================== */

/* ====================== function name ====================== */ int mlc_ext_int_rot (value)

/* ========================= comments ========================= */
/*
Transform rotation from external to internal degrees
 */
/* ======================= declarations ======================= */
/*
type      parameter    i/o      description
--------  -----------  -------  ---------------------------------------*/
int       value;       /* i     degrees to transform                 */

/* ========================== log ========================== */
/*
return status description
--------------  --------------------------------------------- date      comments
--------  ----------------------------------------------------------
07/17/92  Creation - Jeremy Wong
 */
/* ================================================================ */

{ return value - 90;

} mlc.h
/* ====================== include files ====================== */

/* ====================== include name ====================== */ include <xview/xview.h>
include "mlc_ui.h"

/* ======================= comments ======================= */
/*
mlc
 */
/* ========================== log ========================== */
/*
```

```
date     comments
-------- ----------------------------------------------------------------
07/17/92 Creation - Jeremy Wong
 */
/* ================================================================= */ ifndef MLC
define MLC define NGANTRY    50       /* max. number of gantry angles */
define NLEAF      16       /* number of leaves + 1 */
#define MLEAF      4        /* number of intervals/leaf */
#define MAXLEAFx   3.       /* max. x coord. of leaf (in cm) */
#define MINLEAFx   -3.      /* min. x coord. of leaf (in cm) */
#define MAXLEAFy   3.       /* max. y coord. of leaf (in cm) */
#define MINLEAFy   -3.      /* min. y coord. of leaf (in cm) */
#define INCRLEAF   0.4      /* leaf increment (in cm) */
#define INCRMLEAF  0.1      /* interval increment (in cm) */
#define CLOSELEAF  1.e-6    /* error correction */
#define LSLEAF     0.73     /* SCD = 75 cm, SAD = 100cm */
#define RSLEAF     0.695    /* SCD = 75 cm, SAD = 100cm */
#define CSLEAF     0.69     /* SCD = 75 cm, SAD = 100cm */
define FIELDNAME  50       /* max. length of field name */ typedef struct point { double x, y;

} point;

typedef struct { mlc_win_objects *ip;
mlc_popup1_objects *ip1;
mlc_popup2_objects *ip2;
mlc_popup3_objects *ip3;
/*mlc_popup4_objects *ip4;*/
char lname[32], fname[32], pid[32];
int ngantry, npoints, save_npoints;
int gantry[NGANTRY], ngpoints[NGANTRY];
point *gpoints[NGANTRY], *points, *save_points;
point gpt_left[NGANTRY][NLEAF-1], gpt_right[NGANTRY][NLEAF-1];
point pt_left[NLEAF-1], pt_right[NLEAF-1];
char field[NGANTRY][FIELDNAME];
char infile[128], outfile[128];
int stat, stat_leaf[NGANTRY], stat_coll[NGANTRY];
int rotate_angle[NGANTRY], leaf_area[NGANTRY], beam, interval,
    average[NGANTRY];
double shift_x, shift_y;
double x1[NGANTRY], x2[NGANTRY], y1[NGANTRY], y2[NGANTRY];
XColor mlc_colors[6];
Pixmap pmap;

} mlc_x_objects;

extern int mlc_int_ext_rot();
extern int mlc_ext_int_rot();
```

```
endif /* MLC */ mlc_u.c
/*
 * mlc_u.c - User interface object initialization functions.
 * This file was generated by `gxv' from `mlc.G'.
 * DO NOT EDIT BY HAND.
 */ include <stdio.h>
include <sys/param.h>
#include <sys/types.h>
#include <xview/xview.h>
#include <xview/canvas.h>
#include <xview/icon_load.h>
#include <xview/panel.h>
#include <xview/scrollbar.h>
#include <xview/svrimage.h>
#include <xview/termsw.h>
#include <xview/text.h>
#include <xview/tty.h>
#include <xview/xv_xrect.h>
#include "mlc_u.h"

/*
 * Initialize an instance of object `win'.
 */
mlc_objects *
mlc_objects_initialize(ip, owner)
        mlc_objects *ip;
        Xv_opaque   owner;
{
        if (!ip && !(ip = (mlc_objects *) calloc(1, sizeof
(mlc_objects))))
                return (mlc_objects *) NULL;
        if (!ip->win)
                ip->win = mlc_win_create(ip, owner);
        return ip;
}

/*
 * Create object `win' in the specified instance.

*/
Xv_opaque
mlc_win_create(ip, owner)
        caddr_t     ip;
        Xv_opaque   owner;
{
        Xv_opaque   obj;

obj = xv_create(owner, FRAME,
                XV_KEY_DATA, INSTANCE, ip,
                XV_WIDTH, 1,
                XV_HEIGHT, 1,
                XV_LABEL, "Base Window",
        WIN_TRANSPARENT,
        WIN_TOP_LEVEL_NO_DECOR, TRUE,
                FRAME_CLOSED, FALSE,
                FRAME_SHOW_FOOTER, TRUE,
```

```
               FRAME_SHOW_RESIZE_CORNER, TRUE,
               NULL);
        return obj;
} mlc_u.h
ifndef    mlcu_HEADER
#define    mlcu_HEADER

/*
 * mlc_u.h - User interface object and function declarations.
 * This file was generated by `gxv' from `mlc.G'.
 * DO NOT EDIT BY HAND.
 */ extern Attr_attribute   INSTANCE;

typedef struct {
        Xv_opaque    win;
} mlc_objects;

extern mlc_objects     *mlc_objects_initialize();

extern Xv_opaque  mlc_win_create();
endif mlc_ui.c
/*
 * mlc_ui.c - User interface object initialization functions.
 * This file was generated by `gxv' from `mlc.G'.
 * DO NOT EDIT BY HAND.
 */ include <stdio.h>
include <sys/param.h>
#include <sys/types.h>
#include <xview/xview.h>
#include <xview/canvas.h>
#include <xview/panel.h>
#include <xview/scrollbar.h>
#include <xview/svrimage.h>
#include <xview/termsw.h>
#include <xview/text.h>
#include <xview/tty.h>
#include <xview/xv_xrect.h>
#include "mlc_ui.h"

/*
 * Initialize an instance of object `win'.
 */
mlc_win_objects *
mlc_win_objects_initialize(ip, owner)
        mlc_win_objects   *ip;
        Xv_opaque    owner;
{
        if (!ip && !(ip = (mlc_win_objects *) calloc(1, sizeof
(mlc_win_objects))))
                return (mlc_win_objects *) NULL;
        if (!ip->win)
```

```
               ip->win = mlc_win_win_create(ip, owner);
       if (!ip->controls1)
               ip->controls1 = mlc_win_controls1_create(ip, ip->win);
       if (!ip->list_mlc)
               ip->list_mlc = mlc_win_list_mlc_create(ip, ip->controls1);
       if (!ip->load_contour)
               ip->load_contour = mlc_win_load_contour_create(ip, ip-
>controls1);
       if (!ip->opt_mlc)
               ip->opt_mlc = mlc_win_opt_mlc_create(ip, ip->controls1);
       if (!ip->tshift)
               ip->tshift = mlc_win_tshift_create(ip, ip->controls1);
       if (!ip->lshift)
               ip->lshift = mlc_win_lshift_create(ip, ip->controls1);
       if (!ip->rshift)
               ip->rshift = mlc_win_rshift_create(ip, ip->controls1);
       if (!ip->draw_mlc)
               ip->draw_mlc = mlc_win_draw_mlc_create(ip, ip->controls1);
       if (!ip->save_mlc)
               ip->save_mlc = mlc_win_save_mlc_create(ip, ip->controls1);
       if (!ip->shift)
               ip->shift = mlc_win_shift_create(ip, ip->controls1);
       if (!ip->bshift)
               ip->bshift = mlc_win_bshift_create(ip, ip->controls1);
       if (!ip->adjust_mlc)
               ip->adjust_mlc = mlc_win_adjust_mlc_create(ip, ip-
>controls1);
       if (!ip->exit_mlc)
               ip->exit_mlc = mlc_win_exit_mlc_create(ip, ip->controls1);
       if (!ip->adjust1)
               ip->adjust1 = mlc_win_adjust1_create(ip, ip->controls1);
       if (!ip->rotate)
               ip->rotate = mlc_win_rotate_create(ip, ip->controls1);
       if (!ip->interval)
               ip->interval = mlc_win_interval_create(ip, ip->controls1);
       if (!ip->adjust2)
               ip->adjust2 = mlc_win_adjust2_create(ip, ip->controls1);
       if (!ip->leaf_area)
               ip->leaf_area = mlc_win_leaf_area_create(ip, ip->controls1);
       if (!ip->average)
               ip->average = mlc_win_average_create(ip, ip->controls1);
       if (!ip->adjust3)
               ip->adjust3 = mlc_win_adjust3_create(ip, ip->controls1);
       if (!ip->canvas1)
               ip->canvas1 = mlc_win_canvas1_create(ip, ip->win);
       return ip;
}

/*
 * Create object `win' in the specified instance.
 */
Xv_opaque
mlc_win_win_create(ip, owner)
       mlc_win_objects   *ip;
       Xv_opaque   owner;
{
       Xv_opaque   obj;
       Xv_opaque   win_image;
       static unsigned short   win_bits[] = {
#include "mlc.icon"
```

```
      };
      Xv_opaque         win_image_mask;
      static unsigned short  win_mask_bits[] = {
#include "mlc_mask.icon"
      };

win_image = xv_create(XV_NULL, SERVER_IMAGE,
            SERVER_IMAGE_DEPTH, 1,
            SERVER_IMAGE_BITS, win_bits,
            XV_WIDTH, 64,
            XV_HEIGHT, 64,
            NULL);
      win_image_mask = xv_create(XV_NULL, SERVER_IMAGE,
            SERVER_IMAGE_DEPTH, 1,
            SERVER_IMAGE_BITS, win_mask_bits,
            XV_WIDTH, 64,
            XV_HEIGHT, 64,
            NULL);
      obj = xv_create(owner, FRAME,
            XV_KEY_DATA, INSTANCE, ip,
            XV_WIDTH, 650,
            XV_HEIGHT, 800,
            XV_LABEL, "MLC",
            FRAME_SHOW_FOOTER, TRUE,
            FRAME_SHOW_RESIZE_CORNER, FALSE,
            FRAME_ICON, xv_create(XV_NULL, ICON,
                  ICON_IMAGE, win_image,
                  ICON_MASK_IMAGE, win_image_mask,
                  NULL),
            NULL);
      return obj;
}

/*
 * Create object `controls1' in the specified instance.
 */
Xv_opaque
mlc_win_controls1_create(ip, owner)
      mlc_win_objects  *ip;
      Xv_opaque   owner;
{
      Xv_opaque   obj;

obj = xv_create(owner, PANEL,
            XV_KEY_DATA, INSTANCE, ip,
            XV_X, 0,
            XV_Y, 0,
            XV_WIDTH, WIN_EXTEND_TO_EDGE,
            XV_HEIGHT, 200,
            WIN_BORDER, FALSE,
            NULL);
      return obj;
}

/*
 * Create object `list_mlc' in the specified instance.
 */
Xv_opaque
mlc_win_list_mlc_create(ip, owner)
      mlc_win_objects   *ip;
```

```c
        Xv_opaque    owner;
{
        extern int       mlc_list_mlc();
        Xv_opaque    obj;

obj = xv_create(owner, PANEL_LIST,
                XV_KEY_DATA, INSTANCE, ip,
                XV_X, 160,
                XV_Y, 5,
                PANEL_LIST_WIDTH, 200,
                PANEL_LIST_DISPLAY_ROWS, 5,
                PANEL_LABEL_STRING, "  Beam                    Gantry Angle",
                PANEL_LAYOUT, PANEL_VERTICAL,
                PANEL_READ_ONLY, FALSE,
                PANEL_CHOOSE_ONE, TRUE,
                PANEL_CHOOSE_NONE, TRUE,
                PANEL_NOTIFY_PROC, mlc_list_mlc,
                NULL);
        return obj;
}

/*
 * Create object `load_contour' in the specified instance.
 */
Xv_opaque
mlc_win_load_contour_create(ip, owner)
        mlc_win_objects   *ip;
        Xv_opaque    owner;
{
        extern void      mlc_load_contour();
        Xv_opaque    obj;

obj = xv_create(owner, PANEL_BUTTON,
                XV_KEY_DATA, INSTANCE, ip,
                XV_X, 30,
                XV_Y, 20,
                PANEL_LABEL_STRING, "Load Contour",
                PANEL_NOTIFY_PROC, mlc_load_contour,
                NULL);
        return obj;
}

/*
 * Create object `opt_mlc' in the specified instance.
 */
Xv_opaque
mlc_win_opt_mlc_create(ip, owner)
        mlc_win_objects   *ip;
        Xv_opaque    owner;
{
        extern void      mlc_opt_mlc();
        Xv_opaque    obj;

obj = xv_create(owner, PANEL_BUTTON,
                XV_KEY_DATA, INSTANCE, ip,
                XV_X, 516,
                XV_Y, 20,
                PANEL_LABEL_STRING, "Optimize MLC",
                PANEL_NOTIFY_PROC, mlc_opt_mlc,
                NULL);
```

```
        return obj;
}

/*
 * Create object `tshift' in the specified instance.
 */
Xv_opaque
mlc_win_tshift_create(ip, owner)
        mlc_win_objects   *ip;
        Xv_opaque    owner;
{
        extern void       mlc_tshift_mlc();
        Xv_opaque    obj;
        Xv_opaque         tshift_image;
        static unsigned short   tshift_bits[] = {
#include "mlc_tshift.icon"
        };

tshift_image = xv_create(XV_NULL, SERVER_IMAGE,
                SERVER_IMAGE_DEPTH, 1,
                SERVER_IMAGE_BITS, tshift_bits,
                XV_WIDTH, 16,
                XV_HEIGHT, 16,
                NULL);
        obj = xv_create(owner, PANEL_BUTTON,
                XV_KEY_DATA, INSTANCE, ip,
                XV_X, 457,
                XV_Y, 33,
                PANEL_LABEL_IMAGE, tshift_image,
                XV_SHOW, FALSE,
                PANEL_EVENT_PROC, mlc_tshift_mlc,
                NULL);
        return obj;
}

/*
 * Create object `lshift' in the specified instance.
 */
Xv_opaque
mlc_win_lshift_create(ip, owner)
        mlc_win_objects   *ip;
        Xv_opaque    owner;
{
        extern void       mlc_lshift_mlc();
        Xv_opaque    obj;
        Xv_opaque         lshift_image;
        static unsigned short   lshift_bits[] = {
#include "mlc_lshift.icon"
        };

lshift_image = xv_create(XV_NULL, SERVER_IMAGE,
                SERVER_IMAGE_DEPTH, 1,
                SERVER_IMAGE_BITS, lshift_bits,
                XV_WIDTH, 16,
                XV_HEIGHT, 16,
                NULL);
        obj = xv_create(owner, PANEL_BUTTON,
                XV_KEY_DATA, INSTANCE, ip,
                XV_X, 435,
                XV_Y, 58,
```

```
              PANEL_LABEL_IMAGE, lshift_image,
              XV_SHOW, FALSE,
              PANEL_EVENT_PROC, mlc_lshift_mlc,
              NULL);
       return obj;
}

/*
 * Create object `rshift' in the specified instance.
 */
Xv_opaque
mlc_win_rshift_create(ip, owner)
       mlc_win_objects   *ip;
       Xv_opaque   owner;
{
       extern void       mlc_rshift_mlc();
       Xv_opaque   obj;
       Xv_opaque         rshift_image;
       static unsigned short   rshift_bits[] = {
#include "mlc_rshift.icon"
       };

rshift_image = xv_create(XV_NULL, SERVER_IMAGE,
              SERVER_IMAGE_DEPTH, 1,
              SERVER_IMAGE_BITS, rshift_bits,
              XV_WIDTH, 16,
              XV_HEIGHT, 16,
              NULL);
       obj = xv_create(owner, PANEL_BUTTON,
              XV_KEY_DATA, INSTANCE, ip,
              XV_X, 478,
              XV_Y, 58,
              PANEL_LABEL_IMAGE, rshift_image,
              XV_SHOW, FALSE,
              PANEL_EVENT_PROC, mlc_rshift_mlc,
              NULL);
       return obj;
}

/*
 * Create object `draw_mlc' in the specified instance.
 */
Xv_opaque
mlc_win_draw_mlc_create(ip, owner)
       mlc_win_objects   *ip;
       Xv_opaque   owner;
{
       extern void       mlc_draw_mlc();
       Xv_opaque   obj;

obj = xv_create(owner, PANEL_BUTTON,
              XV_KEY_DATA, INSTANCE, ip,
              XV_X, 30,
              XV_Y, 60,
              PANEL_LABEL_STRING, "Draw MLC",
              PANEL_NOTIFY_PROC, mlc_draw_mlc,
              NULL);
       return obj;
}
```

```c
/*
 * Create object `save_mlc' in the specified instance.
 */
Xv_opaque
mlc_win_save_mlc_create(ip, owner)
    mlc_win_objects  *ip;
    Xv_opaque   owner;
{
    extern void     mlc_save_mlc();
    Xv_opaque  obj;

obj = xv_create(owner, PANEL_BUTTON,
        XV_KEY_DATA, INSTANCE, ip,
        XV_X, 544,
        XV_Y, 60,
        PANEL_LABEL_STRING, "Save MLC",
        PANEL_NOTIFY_PROC, mlc_save_mlc,
        NULL);
    return obj;
}

/*
 * Create object `shift' in the specified instance.
 */
Xv_opaque
mlc_win_shift_create(ip, owner)
    mlc_win_objects  *ip;
    Xv_opaque   owner;
{
    Xv_opaque  obj;

obj = xv_create(owner, PANEL_MESSAGE,
        XV_KEY_DATA, INSTANCE, ip,
        XV_X, 394,
        XV_Y, 64,
        PANEL_LABEL_STRING, "Shift:",
        PANEL_LABEL_BOLD, TRUE,
        XV_SHOW, FALSE,
        NULL);
    return obj;
}

/*
 * Create object `bshift' in the specified instance.
 */
Xv_opaque
mlc_win_bshift_create(ip, owner)
    mlc_win_objects  *ip;
    Xv_opaque   owner;
{
    extern void     mlc_bshift_mlc();
    Xv_opaque  obj;
    Xv_opaque       bshift_image;
    static unsigned short   bshift_bits[] = {
#include "mlc_bshift.icon"
    };

bshift_image = xv_create(XV_NULL, SERVER_IMAGE,
        SERVER_IMAGE_DEPTH, 1,
        SERVER_IMAGE_BITS, bshift_bits,
```

```
            XV_WIDTH, 16,
            XV_HEIGHT, 16,
            NULL);
    obj = xv_create(owner, PANEL_BUTTON,
            XV_KEY_DATA, INSTANCE, ip,
            XV_X, 457,
            XV_Y, 83,
            PANEL_LABEL_IMAGE, bshift_image,
            XV_SHOW, FALSE,
            PANEL_EVENT_PROC, mlc_bshift_mlc,
            NULL);
    return obj;
}

/*
 * Create object `adjust_mlc' in the specified instance.
 */
Xv_opaque
mlc_win_adjust_mlc_create(ip, owner)
    mlc_win_objects   *ip;
    Xv_opaque   owner;
{
    extern void     mlc_adjust_mlc();
    Xv_opaque   obj;

obj = xv_create(owner, PANEL_BUTTON,
            XV_KEY_DATA, INSTANCE, ip,
            XV_X, 30,
            XV_Y, 100,
            PANEL_LABEL_STRING, "Adjust MLC",
            PANEL_NOTIFY_PROC, mlc_adjust_mlc,
            NULL);
    return obj;
}

/*
 * Create object `exit_mlc' in the specified instance.
 */
Xv_opaque
mlc_win_exit_mlc_create(ip, owner)
    mlc_win_objects   *ip;
    Xv_opaque   owner;
{
    extern void     mlc_exit_mlc();
    Xv_opaque   obj;

obj = xv_create(owner, PANEL_BUTTON,
            XV_KEY_DATA, INSTANCE, ip,
            XV_X, 580,
            XV_Y, 100,
            PANEL_LABEL_STRING, "Exit",
            PANEL_NOTIFY_PROC, mlc_exit_mlc,
            NULL);
    return obj;
}

/*
 * Create object `adjust1' in the specified instance.
 */
Xv_opaque
```

```
mlc_win_adjust1_create(ip, owner)
    mlc_win_objects   *ip;
    Xv_opaque   owner;
{
    Xv_opaque   obj;

obj = xv_create(owner, PANEL_MESSAGE,
          XV_KEY_DATA, INSTANCE, ip,
          XV_X, 358,
          XV_Y, 140,
          PANEL_LABEL_STRING, "Left button for adjusting left leaf",
          PANEL_LABEL_BOLD, TRUE,
          XV_SHOW, FALSE,
          NULL);
    return obj;
}

/*
 * Create object `rotate' in the specified instance.
 */
Xv_opaque
mlc_win_rotate_create(ip, owner)
    mlc_win_objects   *ip;
    Xv_opaque   owner;
{
    extern void     mlc_rotation_mlc();
    Xv_opaque   obj;

obj = xv_create(owner, PANEL_SLIDER,
          XV_KEY_DATA, INSTANCE, ip,
          XV_X, 4,
          XV_Y, 145,
          PANEL_SLIDER_WIDTH, 91,
          PANEL_TICKS, 10,
          PANEL_LABEL_STRING, "Coll. Angle:",
          PANEL_DIRECTION, PANEL_HORIZONTAL,
          PANEL_SLIDER_END_BOXES, TRUE,
          PANEL_SHOW_RANGE, TRUE,
          PANEL_SHOW_VALUE, TRUE,
          PANEL_MIN_VALUE, 0,
          PANEL_MAX_VALUE, 360,
          PANEL_VALUE, 0,
          PANEL_NOTIFY_PROC, mlc_rotation_mlc,
          NULL);
    return obj;
}

/*
 * Create object `interval' in the specified instance.
 */
Xv_opaque
mlc_win_interval_create(ip, owner)
    mlc_win_objects   *ip;
    Xv_opaque   owner;
{
    extern void     mlc_interval_mlc();
    Xv_opaque   obj;

obj = xv_create(owner, PANEL_SLIDER,
          XV_KEY_DATA, INSTANCE, ip,
```

```
                XV_X, 325,
                XV_Y, 145,
                PANEL_SLIDER_WIDTH, 91,
                PANEL_TICKS, 10,
                PANEL_LABEL_STRING, "Interval for Opt.:",
                PANEL_DIRECTION, PANEL_HORIZONTAL,
                PANEL_SLIDER_END_BOXES, TRUE,
                PANEL_SHOW_RANGE, TRUE,
                PANEL_SHOW_VALUE, TRUE,
                PANEL_MIN_VALUE, 1,
                PANEL_MAX_VALUE, 90,
                PANEL_VALUE, 0,
                PANEL_NOTIFY_PROC, mlc_interval_mlc,
                NULL);
        return obj;
}

/*
 * Create object `adjust2' in the specified instance.
 */
Xv_opaque
mlc_win_adjust2_create(ip, owner)
        mlc_win_objects  *ip;
        Xv_opaque        owner;
{
        Xv_opaque        obj;

obj = xv_create(owner, PANEL_MESSAGE,
                XV_KEY_DATA, INSTANCE, ip,
                XV_X, 358,
                XV_Y, 160,
                PANEL_LABEL_STRING, "Middle button for terminating adjustment",
                PANEL_LABEL_BOLD, TRUE,
                XV_SHOW, FALSE,
                NULL);
        return obj;
}

/*
 * Create object `leaf_area' in the specified instance.
 */
Xv_opaque
mlc_win_leaf_area_create(ip, owner)
        mlc_win_objects  *ip;
        Xv_opaque        owner;
{
        extern void      mlc_leaf_area();
        Xv_opaque        obj;

obj = xv_create(owner, PANEL_SLIDER,
                XV_KEY_DATA, INSTANCE, ip,
                XV_X, 295,
                XV_Y, 170,
                PANEL_SLIDER_WIDTH, 101,
                PANEL_TICKS, 11,
                PANEL_LABEL_STRING, "Leaf Insertion (%):",
                PANEL_DIRECTION, PANEL_HORIZONTAL,
                PANEL_SLIDER_END_BOXES, TRUE,
                PANEL_SHOW_RANGE, TRUE,
```

```
            PANEL_SHOW_VALUE, TRUE,
            PANEL_MIN_VALUE, 0,
            PANEL_MAX_VALUE, 100,
            PANEL_VALUE, 0,
            PANEL_NOTIFY_PROC, mlc_leaf_area,
            NULL);
    return obj;
}

/*
 * Create object `average' in the specified instance.
 */
Xv_opaque
mlc_win_average_create(ip, owner)
    mlc_win_objects  *ip;
    Xv_opaque   owner;
{
    extern void     mlc_average_mlc();
    Xv_opaque   obj;

obj = xv_create(owner, PANEL_CHOICE,
            XV_KEY_DATA, INSTANCE, ip,
            XV_X, 4,
            XV_Y, 171,
            PANEL_CHOICE_NROWS, 1,
            PANEL_LAYOUT, PANEL_HORIZONTAL,
            PANEL_CHOOSE_NONE, FALSE,
            PANEL_LABEL_STRING, "Leaf Average:",
            PANEL_NOTIFY_PROC, mlc_average_mlc,
            PANEL_CHOICE_STRINGS,
                "3",
                "5",
                NULL,
            NULL);
    return obj;
}

/*
 * Create object `adjust3' in the specified instance.
 */
Xv_opaque
mlc_win_adjust3_create(ip, owner)
    mlc_win_objects  *ip;
    Xv_opaque   owner;
{
    Xv_opaque   obj;

obj = xv_create(owner, PANEL_MESSAGE,
            XV_KEY_DATA, INSTANCE, ip,
            XV_X, 358,
            XV_Y, 180,
            PANEL_LABEL_STRING, "Right button for adjusting right leaf",
            PANEL_LABEL_BOLD, TRUE,
            XV_SHOW, FALSE,
            NULL);
    return obj;
}

/*
 * Create object `canvas1' in the specified instance.
```

```
*/
Xv_opaque
mlc_win_canvas1_create(ip, owner)
    mlc_win_objects   *ip;
    Xv_opaque   owner;
{
    extern void mlc_repaint_mlc();
    Xv_opaque   obj;

obj = xv_create(owner, CANVAS,
        XV_KEY_DATA, INSTANCE, ip,
        XV_X, 25,
        XV_Y, (int)xv_get(ip->controls1, XV_Y) +
            (int)xv_get(ip->controls1, XV_HEIGHT),
        XV_WIDTH, 600,
        XV_HEIGHT, WIN_EXTEND_TO_EDGE,
        CANVAS_REPAINT_PROC, mlc_repaint_mlc,
        NULL);
    /*
     * This line is here for backwards compatibility. It will be
     * removed for the next release.
     */
    xv_set(canvas_paint_window(obj), XV_KEY_DATA, INSTANCE, ip, NULL);
    return obj;
}

/*
 * Initialize an instance of object `popup1'.
 */
mlc_popup1_objects *
mlc_popup1_objects_initialize(ip, owner)
    mlc_popup1_objects   *ip;
    Xv_opaque   owner;
{
    if (!ip && !(ip = (mlc_popup1_objects *) calloc(1, sizeof
(mlc_popup1_objects))))
            return (mlc_popup1_objects *) NULL;
    if (!ip->popup1)
            ip->popup1 = mlc_popup1_popup1_create(ip, owner);
    if (!ip->controls2)
            ip->controls2 = mlc_popup1_controls2_create(ip, ip->popup1);
    if (!ip->lname)
            ip->lname = mlc_popup1_lname_create(ip, ip->controls2);
    if (!ip->fname)
            ip->fname = mlc_popup1_fname_create(ip, ip->controls2);
    if (!ip->pid)
            ip->pid = mlc_popup1_pid_create(ip, ip->controls2);
    if (!ip->dir1)
            ip->dir1 = mlc_popup1_dir1_create(ip, ip->controls2);
    if (!ip->file1)
            ip->file1 = mlc_popup1_file1_create(ip, ip->controls2);
    if (!ip->dir3)
            ip->dir3 = mlc_popup1_dir3_create(ip, ip->controls2);
    if (!ip->file3)
            ip->file3 = mlc_popup1_file3_create(ip, ip->controls2);
    if (!ip->load_file)
            ip->load_file = mlc_popup1_load_file_create(ip, ip-
>controls2);
    return ip;
}
```

```
/*
 * Create object `popup1' in the specified instance.
 */
Xv_opaque
mlc_popup1_popup1_create(ip, owner)
	mlc_popup1_objects	*ip;
	Xv_opaque	owner;
{
	Xv_opaque	obj;

obj = xv_create(owner, FRAME_CMD,
		XV_KEY_DATA, INSTANCE, ip,
		XV_WIDTH, 600,
		XV_HEIGHT, 300,
		XV_LABEL, "MLC: Load Contour",
		XV_SHOW, FALSE,
		FRAME_SHOW_FOOTER, TRUE,
		FRAME_SHOW_RESIZE_CORNER, TRUE,
		FRAME_CMD_PUSHPIN_IN, FALSE,
		NULL);
	xv_set(xv_get(obj, FRAME_CMD_PANEL), WIN_SHOW, FALSE, NULL);
	return obj;
}

/*
 * Create object `controls2' in the specified instance.
 */
Xv_opaque
mlc_popup1_controls2_create(ip, owner)
	mlc_popup1_objects	*ip;
	Xv_opaque	owner;
{
	Xv_opaque	obj;

obj = xv_create(owner, PANEL,
		XV_KEY_DATA, INSTANCE, ip,
		XV_X, 0,
		XV_Y, 0,
		XV_WIDTH, WIN_EXTEND_TO_EDGE,
		XV_HEIGHT, WIN_EXTEND_TO_EDGE,
		WIN_BORDER, FALSE,
		NULL);
	return obj;
}

/*
 * Create object `lname' in the specified instance.
 */
Xv_opaque
mlc_popup1_lname_create(ip, owner)
	mlc_popup1_objects	*ip;
	Xv_opaque	owner;
{
	Xv_opaque	obj;

obj = xv_create(owner, PANEL_TEXT,
		XV_KEY_DATA, INSTANCE, ip,
		XV_X, 32,
		XV_Y, 32,
```

```c
                PANEL_VALUE_DISPLAY_LENGTH, 19,
                PANEL_VALUE_STORED_LENGTH, 19,
                PANEL_LABEL_STRING, "Patient Last Name:",
                PANEL_LAYOUT, PANEL_HORIZONTAL,
                PANEL_READ_ONLY, FALSE,
                NULL);
        return obj;
}

/*
 * Create object `fname' in the specified instance.
 */
Xv_opaque
mlc_popup1_fname_create(ip, owner)
        mlc_popup1_objects      *ip;
        Xv_opaque       owner;
{
        Xv_opaque       obj;

obj = xv_create(owner, PANEL_TEXT,
                XV_KEY_DATA, INSTANCE, ip,
                XV_X, 30,
                XV_Y, 64,
                PANEL_VALUE_DISPLAY_LENGTH, 19,
                PANEL_VALUE_STORED_LENGTH, 19,
                PANEL_LABEL_STRING, "Patient First Name:",
                PANEL_LAYOUT, PANEL_HORIZONTAL,
                PANEL_READ_ONLY, FALSE,
                NULL);
        return obj;
}

/*
 * Create object `pid' in the specified instance.
 */
Xv_opaque
mlc_popup1_pid_create(ip, owner)
        mlc_popup1_objects      *ip;
        Xv_opaque       owner;
{
        Xv_opaque       obj;

obj = xv_create(owner, PANEL_TEXT,
                XV_KEY_DATA, INSTANCE, ip,
                XV_X, 89,
                XV_Y, 96,
                PANEL_VALUE_DISPLAY_LENGTH, 6,
                PANEL_VALUE_STORED_LENGTH, 6,
                PANEL_LABEL_STRING, "Patient ID:",
                PANEL_LAYOUT, PANEL_HORIZONTAL,
                PANEL_READ_ONLY, FALSE,
                NULL);
        return obj;
}

/*
 * Create object `dir1' in the specified instance.
 */
Xv_opaque
mlc_popup1_dir1_create(ip, owner)
```

```
	mlc_popup1_objects	*ip;
	Xv_opaque	owner;
{
	Xv_opaque	obj;

obj = xv_create(owner, PANEL_TEXT,
		XV_KEY_DATA, INSTANCE, ip,
		XV_X, 35,
		XV_Y, 128,
		PANEL_VALUE_DISPLAY_LENGTH, 50,
		PANEL_VALUE_STORED_LENGTH, 50,
		PANEL_LABEL_STRING, "Contour Directory:",
		PANEL_LAYOUT, PANEL_HORIZONTAL,
		PANEL_READ_ONLY, FALSE,
		NULL);
	return obj;
}

/*
 * Create object `file1' in the specified instance.
 */
Xv_opaque
mlc_popup1_file1_create(ip, owner)
	mlc_popup1_objects	*ip;
	Xv_opaque	owner;
{
	Xv_opaque	obj;

obj = xv_create(owner, PANEL_TEXT,
		XV_KEY_DATA, INSTANCE, ip,
		XV_X, 73,
		XV_Y, 160,
		PANEL_VALUE_DISPLAY_LENGTH, 50,
		PANEL_VALUE_STORED_LENGTH, 50,
		PANEL_LABEL_STRING, "Contour File:",
		PANEL_LAYOUT, PANEL_HORIZONTAL,
		PANEL_READ_ONLY, FALSE,
		NULL);
	return obj;
}

/*
 * Create object `dir3' in the specified instance.
 */
Xv_opaque
mlc_popup1_dir3_create(ip, owner)
	mlc_popup1_objects	*ip;
	Xv_opaque	owner;
{
	Xv_opaque	obj;

obj = xv_create(owner, PANEL_TEXT,
		XV_KEY_DATA, INSTANCE, ip,
		XV_X, 60,
		XV_Y, 192,
		PANEL_VALUE_DISPLAY_LENGTH, 50,
		PANEL_VALUE_STORED_LENGTH, 50,
		PANEL_LABEL_STRING, "MLC Directory:",
		PANEL_LAYOUT, PANEL_HORIZONTAL,
		PANEL_READ_ONLY, FALSE,
```

```
                NULL);
        return obj;
}

/*
 * Create object `file3' in the specified instance.
 */
Xv_opaque
mlc_popup1_file3_create(ip, owner)
        mlc_popup1_objects      *ip;
        Xv_opaque       owner;
{
        extern Panel_setting    mlc_load_text();
        Xv_opaque       obj;

obj = xv_create(owner, PANEL_TEXT,
                XV_KEY_DATA, INSTANCE, ip,
                XV_X, 98,
                XV_Y, 224,
                PANEL_VALUE_DISPLAY_LENGTH, 50,
                PANEL_VALUE_STORED_LENGTH, 50,
                PANEL_LABEL_STRING, "MLC File:",
                PANEL_LAYOUT, PANEL_HORIZONTAL,
                PANEL_READ_ONLY, FALSE,
                PANEL_NOTIFY_PROC, mlc_load_text,
                NULL);
        return obj;
}

/*
 * Create object `load_file' in the specified instance.
 */
Xv_opaque
mlc_popup1_load_file_create(ip, owner)
        mlc_popup1_objects      *ip;
        Xv_opaque       owner;
{
        extern void     mlc_load_file();
        Xv_opaque       obj;

obj = xv_create(owner, PANEL_BUTTON,
                XV_KEY_DATA, INSTANCE, ip,
                XV_X, 268,
                XV_Y, 261,
                PANEL_LABEL_STRING, "Load",
                PANEL_NOTIFY_PROC, mlc_load_file,
                NULL);
        return obj;
}

/*
 * Initialize an instance of object `popup2'.
 */
mlc_popup2_objects *
mlc_popup2_objects_initialize(ip, owner)
        mlc_popup2_objects      *ip;
        Xv_opaque       owner;
{
        if (!ip && !(ip = (mlc_popup2_objects *) calloc(1, sizeof
(mlc_popup2_objects))))
```

```
                return (mlc_popup2_objects *) NULL;
        if (!ip->popup2)
                ip->popup2 = mlc_popup2_popup2_create(ip, owner);
        if (!ip->controls3)
                ip->controls3 = mlc_popup2_controls3_create(ip, ip->popup2);
        if (!ip->dir2)
                ip->dir2 = mlc_popup2_dir2_create(ip, ip->controls3);
        if (!ip->file2)
                ip->file2 = mlc_popup2_file2_create(ip, ip->controls3);
        if (!ip->save_file)
                ip->save_file = mlc_popup2_save_file_create(ip, ip-
>controls3);
        return ip;
}

/*
 * Create object `popup2' in the specified instance.
 */
Xv_opaque
mlc_popup2_popup2_create(ip, owner)
        mlc_popup2_objects      *ip;
        Xv_opaque       owner;
{
        Xv_opaque       obj;

obj = xv_create(owner, FRAME_CMD,
                XV_KEY_DATA, INSTANCE, ip,
                XV_WIDTH, 600,
                XV_HEIGHT, 150,
                XV_LABEL, "MLC: Save MLC",
                XV_SHOW, FALSE,
                FRAME_SHOW_FOOTER, TRUE,
                FRAME_SHOW_RESIZE_CORNER, TRUE,
                FRAME_CMD_PUSHPIN_IN, FALSE,
                NULL);
        xv_set(xv_get(obj, FRAME_CMD_PANEL), WIN_SHOW, FALSE, NULL);
        return obj;
}

/*
 * Create object `controls3' in the specified instance.
 */
Xv_opaque
mlc_popup2_controls3_create(ip, owner)
        mlc_popup2_objects      *ip;
        Xv_opaque       owner;
{
        Xv_opaque       obj;

obj = xv_create(owner, PANEL,
                XV_KEY_DATA, INSTANCE, ip,
                XV_X, 0,
                XV_Y, 0,
                XV_WIDTH, WIN_EXTEND_TO_EDGE,
                XV_HEIGHT, WIN_EXTEND_TO_EDGE,
                WIN_BORDER, FALSE,
                NULL);
        return obj;
}
```

```
/*
 * Create object `dir2' in the specified instance.
 */
Xv_opaque
mlc_popup2_dir2_create(ip, owner)
        mlc_popup2_objects      *ip;
        Xv_opaque       owner;
{
        Xv_opaque       obj;

obj = xv_create(owner, PANEL_TEXT,
                XV_KEY_DATA, INSTANCE, ip,
                XV_X, 68,
                XV_Y, 32,
                PANEL_VALUE_DISPLAY_LENGTH, 50,
                PANEL_VALUE_STORED_LENGTH, 50,
                PANEL_LABEL_STRING, "Directory:",
                PANEL_LAYOUT, PANEL_HORIZONTAL,
                PANEL_READ_ONLY, FALSE,
                NULL);
        return obj;
}

/*
 * Create object `file2' in the specified instance.
 */
Xv_opaque
mlc_popup2_file2_create(ip, owner)
        mlc_popup2_objects      *ip;
        Xv_opaque       owner;
{
        extern Panel_setting    mlc_save_text();
        Xv_opaque       obj;

obj = xv_create(owner, PANEL_TEXT,
                XV_KEY_DATA, INSTANCE, ip,
                XV_X, 106,
                XV_Y, 64,
                PANEL_VALUE_DISPLAY_LENGTH, 50,
                PANEL_VALUE_STORED_LENGTH, 50,
                PANEL_LABEL_STRING, "File:",
                PANEL_LAYOUT, PANEL_HORIZONTAL,
                PANEL_READ_ONLY, FALSE,
                PANEL_NOTIFY_PROC, mlc_save_text,
                NULL);
        return obj;
}

/*
 * Create object `save_file' in the specified instance.
 */
Xv_opaque
mlc_popup2_save_file_create(ip, owner)
        mlc_popup2_objects      *ip;
        Xv_opaque       owner;
{
        extern void     mlc_save_file();
        Xv_opaque       obj;

obj = xv_create(owner, PANEL_BUTTON,
```

```
                XV_KEY_DATA, INSTANCE, ip,
                XV_X, 268,
                XV_Y, 105,
                PANEL_LABEL_STRING, "Save",
                PANEL_NOTIFY_PROC, mlc_save_file,
                NULL);
        return obj;
}

/*
 * Initialize an instance of object `popup3'.
 */
mlc_popup3_objects *
mlc_popup3_objects_initialize(ip, owner)
        mlc_popup3_objects      *ip;
        Xv_opaque       owner;
{
        if (!ip && !(ip = (mlc_popup3_objects *) calloc(1, sizeof
(mlc_popup3_objects))))
                return (mlc_popup3_objects *) NULL;
        if (!ip->popup3)
                ip->popup3 = mlc_popup3_popup3_create(ip, owner);
        if (!ip->controls4)
                ip->controls4 = mlc_popup3_controls4_create(ip, ip->popup3);
        if (!ip->opt11)
                ip->opt11 = mlc_popup3_opt11_create(ip, ip->controls4);
        if (!ip->opt14)
                ip->opt14 = mlc_popup3_opt14_create(ip, ip->controls4);
        if (!ip->cancel_mlc)
                ip->cancel_mlc = mlc_popup3_cancel_mlc_create(ip, ip-
>controls4);
        if (!ip->opt12)
                ip->opt12 = mlc_popup3_opt12_create(ip, ip->controls4);
        if (!ip->opt13)
                ip->opt13 = mlc_popup3_opt13_create(ip, ip->controls4);
        if (!ip->opt4)
                ip->opt4 = mlc_popup3_opt4_create(ip, ip->controls4);
        if (!ip->opt1)
                ip->opt1 = mlc_popup3_opt1_create(ip, ip->controls4);
        if (!ip->opt2)
                ip->opt2 = mlc_popup3_opt2_create(ip, ip->controls4);
        if (!ip->opt3)
                ip->opt3 = mlc_popup3_opt3_create(ip, ip->controls4);
        if (!ip->opt1_mlc)
                ip->opt1_mlc = mlc_popup3_opt1_mlc_create(ip, ip-
>controls4);
        return ip;
}

/*
 * Create object `popup3' in the specified instance.
 */
Xv_opaque
mlc_popup3_popup3_create(ip, owner)
        mlc_popup3_objects      *ip;
        Xv_opaque       owner;
{
        extern void mlc_done1_proc();
        Xv_opaque       obj;
```

```
        obj = xv_create(owner, FRAME_CMD,
                XV_KEY_DATA, INSTANCE, ip,
                XV_WIDTH, 398,
                XV_HEIGHT, 710,
                XV_LABEL, "MLC: Optimize MLC",
                XV_SHOW, FALSE,
                FRAME_SHOW_FOOTER, TRUE,
                FRAME_SHOW_RESIZE_CORNER, TRUE,
                FRAME_CMD_PUSHPIN_IN, FALSE,
                FRAME_DONE_PROC, mlc_done1_proc,
                NULL);
        xv_set(xv_get(obj, FRAME_CMD_PANEL), WIN_SHOW, FALSE, NULL);
        return obj;
}

/*
 * Create object `controls4' in the specified instance.
 */
Xv_opaque
mlc_popup3_controls4_create(ip, owner)
        mlc_popup3_objects      *ip;
        Xv_opaque       owner;
{
        Xv_opaque       obj;

obj = xv_create(owner, PANEL,
                XV_KEY_DATA, INSTANCE, ip,
                XV_X, 0,
                XV_Y, 0,
                XV_WIDTH, WIN_EXTEND_TO_EDGE,
                XV_HEIGHT, WIN_EXTEND_TO_EDGE,
                WIN_BORDER, FALSE,
                NULL);
        return obj;
}

/*
 * Create object `opt11' in the specified instance.
 */
Xv_opaque
mlc_popup3_opt11_create(ip, owner)
        mlc_popup3_objects      *ip;
        Xv_opaque       owner;
{
        Xv_opaque       obj;

obj = xv_create(owner, PANEL_TEXT,
                XV_KEY_DATA, INSTANCE, ip,
                XV_X, 57,
                XV_Y, 20,
                PANEL_VALUE_DISPLAY_LENGTH, 10,
                PANEL_VALUE_STORED_LENGTH, 10,
                PANEL_LABEL_STRING, "Min. area:",
                PANEL_LAYOUT, PANEL_HORIZONTAL,
                PANEL_READ_ONLY, TRUE,
                NULL);
        return obj;
}

/*
```

```
 * Create object `opt14' in the specified instance.
 */
Xv_opaque
mlc_popup3_opt14_create(ip, owner)
      mlc_popup3_objects    *ip;
      Xv_opaque    owner;
{
      Xv_opaque    obj;

obj = xv_create(owner, PANEL_TEXT,
            XV_KEY_DATA, INSTANCE, ip,
            XV_X, 82,
            XV_Y, 40,
            PANEL_VALUE_DISPLAY_LENGTH, 2,
            PANEL_VALUE_STORED_LENGTH, 2,
            PANEL_LABEL_STRING, "Beam:",
            PANEL_LAYOUT, PANEL_HORIZONTAL,
            PANEL_READ_ONLY, TRUE,
            NULL);
      return obj;
}

/*
 * Create object `cancel_mlc' in the specified instance.
 */
Xv_opaque
mlc_popup3_cancel_mlc_create(ip, owner)
      mlc_popup3_objects    *ip;
      Xv_opaque    owner;
{
      extern void    mlc_cancel_mlc();
      Xv_opaque    obj;

obj = xv_create(owner, PANEL_BUTTON,
            XV_KEY_DATA, INSTANCE, ip,
            XV_X, 326,
            XV_Y, 40,
            PANEL_LABEL_STRING, "Quit",
            PANEL_NOTIFY_PROC, mlc_cancel_mlc,
            NULL);
      return obj;
}

/*
 * Create object `opt2' in the specified instance.
 */
Xv_opaque
mlc_popup3_opt2_create(ip, owner)
      mlc_popup3_objects    *ip;
      Xv_opaque    owner;
{
      Xv_opaque    obj;

obj = xv_create(owner, PANEL_TEXT,
            XV_KEY_DATA, INSTANCE, ip,
            XV_X, 32,
            XV_Y, 60,
            PANEL_VALUE_DISPLAY_LENGTH, 4,
            PANEL_VALUE_STORED_LENGTH, 4,
            PANEL_LABEL_STRING, "Gantry Angle:",
```

```c
            PANEL_LAYOUT, PANEL_HORIZONTAL,
            PANEL_READ_ONLY, TRUE,
            NULL);
    return obj;
}

/*
 * Create object `opt13' in the specified instance.
 */
Xv_opaque
mlc_popup3_opt13_create(ip, owner)
    mlc_popup3_objects    *ip;
    Xv_opaque    owner;
{
    Xv_opaque    obj;

obj = xv_create(owner, PANEL_TEXT,
        XV_KEY_DATA, INSTANCE, ip,
        XV_X, 47,
        XV_Y, 80,
        PANEL_VALUE_DISPLAY_LENGTH, 4,
        PANEL_VALUE_STORED_LENGTH, 4,
        PANEL_LABEL_STRING, "Coll. Angle:",
        PANEL_LAYOUT, PANEL_HORIZONTAL,
        PANEL_READ_ONLY, TRUE,
        NULL);
    return obj;
}

/*
 * Create object `opt4' in the specified instance.
 */
Xv_opaque
mlc_popup3_opt4_create(ip, owner)
    mlc_popup3_objects    *ip;
    Xv_opaque    owner;
{
    Xv_opaque    obj;

obj = xv_create(owner, PANEL_MESSAGE,
        XV_KEY_DATA, INSTANCE, ip,
        XV_X, 33,
        XV_Y, 124,
        PANEL_LABEL_STRING, "Beam",
        PANEL_LABEL_BOLD, TRUE,
        NULL);
    return obj;
}

/*
 * Create object `opt1' in the specified instance.
 */
Xv_opaque
mlc_popup3_opt1_create(ip, owner)
    mlc_popup3_objects    *ip;
    Xv_opaque    owner;
{
    Xv_opaque    obj;

obj = xv_create(owner, PANEL_MESSAGE,
```

```c
                XV_KEY_DATA, INSTANCE, ip,
                XV_X, 91,
                XV_Y, 124,
                PANEL_LABEL_STRING, "Gantry Angle",
                PANEL_LABEL_BOLD, TRUE,
                NULL);
        return obj;
}

/*
 * Create object `opt2' in the specified instance.
 */
Xv_opaque
mlc_popup3_opt2_create(ip, owner)
        mlc_popup3_objects      *ip;
        Xv_opaque       owner;
{
        Xv_opaque       obj;

obj = xv_create(owner, PANEL_MESSAGE,
                XV_KEY_DATA, INSTANCE, ip,
                XV_X, 195,
                XV_Y, 124,
                PANEL_LABEL_STRING, "Coll. Angle",
                PANEL_LABEL_BOLD, TRUE,
                NULL);
        return obj;
}

/*
 * Create object `opt3' in the specified instance.
 */
Xv_opaque
mlc_popup3_opt3_create(ip, owner)
        mlc_popup3_objects      *ip;
        Xv_opaque       owner;
{
        Xv_opaque       obj;

obj = xv_create(owner, PANEL_MESSAGE,
                XV_KEY_DATA, INSTANCE, ip,
                XV_X, 284,
                XV_Y, 124,
                PANEL_LABEL_STRING, "Min. Area",
                PANEL_LABEL_BOLD, TRUE,
                NULL);
        return obj;
}

/*
 * Create object `opt1_mlc' in the specified instance.
 */
Xv_opaque
mlc_popup3_opt1_mlc_create(ip, owner)
        mlc_popup3_objects      *ip;
        Xv_opaque       owner;
{
        Xv_opaque       obj;

obj = xv_create(owner, PANEL_LIST,
```

```
            XV_KEY_DATA, INSTANCE, ip,
            XV_X, 32,
            XV_Y, 142,
            PANEL_LIST_WIDTH, 320,
            PANEL_LIST_DISPLAY_ROWS, 30,
            PANEL_LAYOUT, PANEL_VERTICAL,
            PANEL_READ_ONLY, TRUE,
            PANEL_CHOOSE_ONE, TRUE,
            PANEL_CHOOSE_NONE, TRUE,
            NULL);
    return obj;
} mlc_ui.h
ifndef     mlc_HEADER
#define     mlc_HEADER

/*
 * mlc_ui.h - User interface object and function declarations.
 * This file was generated by `gxv' from `mlc.G'.
 * DO NOT EDIT BY HAND.
 */ extern Attr_attribute   INSTANCE;

typedef struct {
    Xv_opaque   win;
    Xv_opaque   controls1;
    Xv_opaque   list_mlc;
    Xv_opaque   load_contour;
    Xv_opaque   opt_mlc;
    Xv_opaque   tshift;
    Xv_opaque   lshift;
    Xv_opaque   rshift;
    Xv_opaque   draw_mlc;
    Xv_opaque   save_mlc;
    Xv_opaque   shift;
    Xv_opaque   bshift;
    Xv_opaque   adjust_mlc;
    Xv_opaque   exit_mlc;
    Xv_opaque   adjust1;
    Xv_opaque   rotate;
    Xv_opaque   interval;
    Xv_opaque   adjust2;
    Xv_opaque   leaf_area;
    Xv_opaque   average;
    Xv_opaque   adjust3;
    Xv_opaque   canvas1;
} mlc_win_objects;

extern mlc_win_objects  *mlc_win_objects_initialize();

extern Xv_opaque  mlc_win_win_create();
extern Xv_opaque  mlc_win_controls1_create();
extern Xv_opaque  mlc_win_list_mlc_create();
extern Xv_opaque  mlc_win_load_contour_create();
extern Xv_opaque  mlc_win_opt_mlc_create();
extern Xv_opaque  mlc_win_tshift_create();
extern Xv_opaque  mlc_win_lshift_create();
```

```
extern Xv_opaque    mlc_win_rshift_create();
extern Xv_opaque    mlc_win_draw_mlc_create();
extern Xv_opaque    mlc_win_save_mlc_create();
extern Xv_opaque    mlc_win_shift_create();
extern Xv_opaque    mlc_win_bshift_create();
extern Xv_opaque    mlc_win_adjust_mlc_create();
extern Xv_opaque    mlc_win_exit_mlc_create();
extern Xv_opaque    mlc_win_adjust1_create();
extern Xv_opaque    mlc_win_rotate_create();
extern Xv_opaque    mlc_win_interval_create();
extern Xv_opaque    mlc_win_adjust2_create();
extern Xv_opaque    mlc_win_leaf_area_create();
extern Xv_opaque    mlc_win_average_create();
extern Xv_opaque    mlc_win_adjust3_create();
extern Xv_opaque    mlc_win_canvas1_create();

typedef struct {
      Xv_opaque    popup1;
      Xv_opaque    controls2;
      Xv_opaque    lname;
      Xv_opaque    fname;
      Xv_opaque    pid;
      Xv_opaque    dir1;
      Xv_opaque    file1;
      Xv_opaque    dir3;
      Xv_opaque    file3;
      Xv_opaque    load_file;
} mlc_popup1_objects;

extern mlc_popup1_objects    *mlc_popup1_objects_initialize();

extern Xv_opaque    mlc_popup1_popup1_create();
extern Xv_opaque    mlc_popup1_controls2_create();
extern Xv_opaque    mlc_popup1_lname_create();
extern Xv_opaque    mlc_popup1_fname_create();
extern Xv_opaque    mlc_popup1_pid_create();
extern Xv_opaque    mlc_popup1_dir1_create();
extern Xv_opaque    mlc_popup1_file1_create();
extern Xv_opaque    mlc_popup1_dir3_create();
extern Xv_opaque    mlc_popup1_file3_create();
extern Xv_opaque    mlc_popup1_load_file_create();

typedef struct {
      Xv_opaque    popup2;
      Xv_opaque    controls3;
      Xv_opaque    dir2;
      Xv_opaque    file2;
      Xv_opaque    save_file;
} mlc_popup2_objects;

extern mlc_popup2_objects    *mlc_popup2_objects_initialize();

extern Xv_opaque    mlc_popup2_popup2_create();
extern Xv_opaque    mlc_popup2_controls3_create();
extern Xv_opaque    mlc_popup2_dir2_create();
extern Xv_opaque    mlc_popup2_file2_create();
extern Xv_opaque    mlc_popup2_save_file_create();

typedef struct {
      Xv_opaque    popup3;
```

```
        Xv_opaque    controls4;
        Xv_opaque    optl1;
        Xv_opaque    optl4;
        Xv_opaque    cancel_mlc;
        Xv_opaque    optl2;
        Xv_opaque    optl3;
        Xv_opaque    opt4;
        Xv_opaque    opt1;
        Xv_opaque    opt2;
        Xv_opaque    opt3;
        Xv_opaque    optl_mlc;
} mlc_popup3_objects;

extern mlc_popup3_objects    *mlc_popup3_objects_initialize();

extern Xv_opaque  mlc_popup3_popup3_create();
extern Xv_opaque  mlc_popup3_controls4_create();
extern Xv_opaque  mlc_popup3_optl1_create();
extern Xv_opaque  mlc_popup3_optl4_create();
extern Xv_opaque  mlc_popup3_cancel_mlc_create();
extern Xv_opaque  mlc_popup3_optl2_create();
extern Xv_opaque  mlc_popup3_optl3_create();
extern Xv_opaque  mlc_popup3_opt4_create();
extern Xv_opaque  mlc_popup3_opt1_create();
extern Xv_opaque  mlc_popup3_opt2_create();
extern Xv_opaque  mlc_popup3_opt3_create();
extern Xv_opaque  mlc_popup3_optl_mlc_create();
endif mlcarea.c
/* ========================= include files ========================= */ include "mlc.h"

/* ========================= function name ========================= */ int MLCarea (points, npoints, rotation, pt_left, pt_right, area)

/* ========================= comments ========================= */
/*
Finds total area of underdose and overdose
 */
/* ========================= declarations ========================= */
/*
type        parameter    i/o      description
---------   ------------ -------- ----------------------------------------*/
point       *points;     /* i     array of contour points                 */
int         npoints;     /* i     number of contour points                */
int         rotation;    /* i     collimator angle rotation               */
point       *pt_left;    /* i     coordinates of left leaves              */
point       *pt_right;   /* i     coordinates of right leaves             */
double      *area;       /* o     total area of underdose and overdose    */

/* ========================= log ========================= */
/*
return status description
--------------  --------------------------------------------------
1               Success
-1              Failure
```

```
date     comments
--------  -----------------------------------------------------------------
02/26/93  Creation - Jeremy Wong
 */
/* =============================================================== */

{ int i, j, found, num_row, num_col;
point min_pt1, max_pt1, min_pt2, max_pt2, pta, ptb, ptc, ptd, pt, pt1,
      pt2;
double udose, odose, ceil();
int MLCptcontour(), MLCptleaf();
point mlc_rot();

/*
   find bounding box of contour
*/

*area = 0.;
if ( npoints <= 0 ) return (1);

min_pt1.x = points[0].x;
max_pt1.x = points[0].x;
for ( i = 1; i < npoints; i++ ) {
   if ( points[i].x < min_pt1.x )
      min_pt1.x = points[i].x;
   if ( points[i].x > max_pt1.x )
      max_pt1.x = points[i].x;
} if ( min_pt1.x < MINLEAFx )
   min_pt1.x = MINLEAFx;
if ( max_pt1.x > MAXLEAFx )
   max_pt1.x = MAXLEAFx;

min_pt1.y = points[0].y;
max_pt1.y = points[0].y;
for ( i = 1; i < npoints; i++ ) {
   if ( points[i].y < min_pt1.y )
      min_pt1.y = points[i].y;
   if ( points[i].y > max_pt1.y )
      max_pt1.y = points[i].y;
} if ( min_pt1.y < MINLEAFy )
   min_pt1.y = MINLEAFy;
if ( max_pt1.y > MAXLEAFy )
   max_pt1.y = MAXLEAFy;

/*
   find bounding box of mlc
*/ found = 0;
pt1.y = MINLEAFy;
pt2.y = pt1.y + INCRLEAF;
for ( i = 0; i < (NLEAF - 1); i++ ) {
   if ( pt_left[i].x != pt_right[i].x ) {
      if ( found == 0 ) {
```

```
            min_pt2.y = pt1.y;
            max_pt2.y = pt2.y;
            found = 1;
        }
        else
            max_pt2.y = pt2.y;
    } pt1.y += INCRLEAF;
    if ( i != (NLEAF - 3) )
        pt2.y += INCRLEAF;
    else
        pt2.y = MAXLEAFy;
}
if ( found == 0 ) return (1);

found = 0;
for ( i = 0; i < (NLEAF - 1); i++ ) {
    if ( pt_left[i].x != pt_right[i].x ) {
        if ( found == 0 ) {
            min_pt2.x = pt_left[i].x;
            max_pt2.x = pt_right[i].x;
            found = 1;
        }
        else {
            if ( pt_left[i].x < min_pt2.x )
                min_pt2.x = pt_left[i].x;
            if ( pt_right[i].x > max_pt2.x )
                max_pt2.x = pt_right[i].x;
        }
    }
} pt.x = min_pt2.x;
pt.y = min_pt2.y;
pta = mlc_rot (rotation, pt);
pt.x = min_pt2.x;
pt.y = max_pt2.y;
ptb = mlc_rot (rotation, pt);
pt.x = max_pt2.x;
pt.y = max_pt2.y;
ptc = mlc_rot (rotation, pt);
pt.x = max_pt2.x;
pt.y = min_pt2.y;
ptd = mlc_rot (rotation, pt);

/*
    find bounding box of contour and mlc
*/ if ( min_pt1.x > pta.x )
    min_pt1.x = pta.x;
if ( min_pt1.x > ptb.x )
    min_pt1.x = ptb.x;
if ( min_pt1.x > ptc.x )
    min_pt1.x = ptc.x;
if ( min_pt1.x > ptd.x )
    min_pt1.x = ptd.x;

if ( min_pt1.y > pta.y )
```

```
      min_pt1.y = pta.y;
   if ( min_pt1.y > ptb.y )
      min_pt1.y = ptb.y;
   if ( min_pt1.y > ptc.y )
      min_pt1.y = ptc.y;
   if ( min_pt1.y > ptd.y )
      min_pt1.y = ptd.y;

if ( max_pt1.x < pta.x )
      max_pt1.x = pta.x;
   if ( max_pt1.x < ptb.x )
      max_pt1.x = ptb.x;
   if ( max_pt1.x < ptc.x )
      max_pt1.x = ptc.x;
   if ( max_pt1.x < ptd.x )
      max_pt1.x = ptd.x;

if ( max_pt1.y < pta.y )
      max_pt1.y = pta.y;
   if ( max_pt1.y < ptb.y )
      max_pt1.y = ptb.y;
   if ( max_pt1.y < ptc.y )
      max_pt1.y = ptc.y;
   if ( max_pt1.y < ptd.y )
      max_pt1.y = ptd.y;

/*
      find total area of underdose and overdose
   */ num_col = (int) (ceil ((max_pt1.x - min_pt1.x) / INCRMLEAF));
   num_row = (int) (ceil ((max_pt1.y - min_pt1.y) / INCRMLEAF));

udose = 0.;
   odose = 0.;
   pt1.x = min_pt1.x;
   pt1.y = min_pt1.y;
   if ( num_col > 1 )
      pt2.x = pt1.x + INCRMLEAF;
   else
      pt2.x = max_pt1.x;
   if ( num_row > 1 )
      pt2.y = pt1.y + INCRMLEAF;
   else
      pt2.y = max_pt1.y;
   for ( i = 0; i < num_row; i++ ) {
      for ( j = 0; j < num_col; j++ ) {
         pt.x = (pt2.x + pt1.x) / 2;
         pt.y = (pt2.y + pt1.y) / 2;

if ( MLCptcontour (&pt, points, npoints) ) {
            if ( !MLCptleaf (rotation, &pt, pt_left, pt_right) )
               udose += (INCRMLEAF * INCRMLEAF);
         }
         else {
            if ( MLCptleaf (rotation, &pt, pt_left, pt_right) )
               odose += (INCRMLEAF * INCRMLEAF);
         } pt1.x = pt2.x;
```

```
            if ( j != (num_col - 2) )
               pt2.x += INCRMLEAF;
            else
               pt2.x = max_pt1.x;
         }
         pt1.x = min_pt1.x;
         pt1.y = pt2.y;
         if ( num_col > 1 )
            pt2.x = pt1.x + INCRMLEAF;
         else
            pt2.x = max_pt1.x;
         if ( i != (num_row - 2) )
            pt2.y += INCRMLEAF;
         else
            pt2.y = max_pt1.y;
      }

*area = udose + odose;

return (1);

ERROR_RETURN:
      fputs ("Error: MLCarea\n", stderr);
      return (-1);

} int
MLCptcontour (pt, points, npoints)
point *pt;
point *points;
int    npoints;
{ int i, j, icount, jcount;
double a, b, c, t, y_int;

icount = 0;
if ( npoints < 3 )
   return FALSE;

for ( i = 0; i < npoints; i++ ) {
   if ( (pt->x == points[i].x) && (pt->y == points[i].y) )
      return TRUE;
} for ( i = 0; i < npoints; i++ ) {
   if ( i != (npoints - 1) )
      j = i + 1;
   else
      j = 0;

if ( (pt->x - points[i].x) * (points[j].x - pt->x) >= 0. ) {
      a = points[j].y - points[i].y;
      b = points[i].x - points[j].x;
      c = points[i].x * a + points[i].y * b;
      if ( a * pt->x + b * pt->y == c ) {
         t = -1.;
```

```
            if ( b != 0. )
                t = (pt->x - points[i].x) / (points[j].x - points[i].x);
            else if ( a != 0. )
                t = (pt->y - points[i].y) / (points[j].y - points[i].y);

if ( (t >= 0.) && (t <= 1.) )
                return TRUE;
        } if ( b != 0. )
            y_int = (c - a * pt->x) / b;
        else {
            y_int = points[j].y;
            if ( points[i].y > points[j].y )
                y_int = points[i].y;
        } if ( pt->y == y_int )
            return TRUE;
        else if ( y_int < pt->y ) {
            if ( (pt->x != points[i].x) && (pt->x != points[j].x) )
                icount++;
            else if ( (pt->x == points[j].x) && (points[i].x < pt->x) )
                icount++;
            else if ( (pt->x == points[i].x) && (points[j].x < pt->x) )
                icount++;
        }
    }
} jcount = (icount / 2) * 2;
return (jcount != icount);

} int
MLCptleaf (rotation, pt, pt_left, pt_right)
int rotation;
point *pt;
point *pt_left;
point *pt_right;
{ int i, j, found;
point p, pt1, pt2;
point mlc_inv_rot();

p = mlc_inv_rot (rotation, *pt);
found = 0;
pt1.y = MINLEAFy;
pt2.y = pt1.y + INCRLEAF;
for ( i = 0; (i < (NLEAF - 1)) && !found; i++ ) {
    if ( (p.y >= pt1.y) && (p.y <= pt2.y) ) {
        found = 1;
        j = i;
    } pt1.y += INCRLEAF;
```

```c
       if ( i != (NLEAF - 3) )
           pt2.y += INCRLEAF;
       else
           pt2.y = MAXLEAFy;
    } if ( found ) {
       if ( (p.x >= pt_left[j].x) && (p.x <= pt_right[j].x) )
           found = 1;
       else
           found = 0;
    } return found;

} mlccheck.c
/* ========================= include files ========================= */ include "mlc.h"

/* ========================= function name ========================= */ int MLCcheck (points, npoints, pt_left, pt_right)

/* ========================= comments ========================= */
/*
Checks for small contour that fits between 2 leaves
 */
/* ========================= declarations ========================= */
/*
type       parameter      i/o       description
---------- -------------- --------- ------------------------------------------*/
 point     *points;       /* i      array of contour points                  */
 int       npoints;       /* i      number of contour points                 */
 point     *pt_left;      /* o      coordinates of left leaves               */
 point     *pt_right;     /* o      coordinates of right leaves              */

/* ========================= log ========================= */
/*
return status description
--------------- -------------------------------------------------
1               Success
-1              Failure date     comments
-------- -------------------------------------------------
07/17/92 Creation - Jeremy Wong
 */
/* ========================================================= */

{ int i, j, found;
double min_ln, max_ln;
point min_pt, max_pt;

/*
   check for small contour that fits between 2 leaves
```

```
*/
return (1);

if ( npoints > 0 ) {
   min_pt.x = points[0].x;
   max_pt.x = points[0].x;
   min_pt.y = points[0].y;
   max_pt.y = points[0].y;
   for ( i = 1; i < npoints; i++ ) {
      if ( points[i].x < min_pt.x )
         min_pt.x = points[i].x;
      if ( points[i].x > max_pt.x )
         max_pt.x = points[i].x;

if ( points[i].y < min_pt.y )
         min_pt.y = points[i].y;
      if ( points[i].y > max_pt.y )
         max_pt.y = points[i].y;
   } min_ln = MINLEAFy;
   max_ln = MINLEAFy + INCRLEAF;
   found = 0;
   for ( i = 0; (i < (NLEAF-1)) && (!found); i++ ) {
      if ( (min_pt.y > min_ln) && (max_pt.y < max_ln) ) {
         found = 1;
         j = i;
      }
      else {
         min_ln += INCRLEAF;
         max_ln += INCRLEAF;
      }
   } if ( found ) {
      found = 0;
      for ( i = 0; i < (NLEAF-1); i++ ) {
         if ( !((pt_left[i].x == 0.) && (pt_right[i].x == 0.)) )
            found = 1;
      } if ( !found ) {
         pt_left[j].x = min_pt.x;
         pt_right[j].x = max_pt.x;
      }
   }
} return (1);

ERROR_RETURN:
fputs ("Error: MLCcheck\n", stderr);
return (-1);

} mlcfit.c
/* ========================= include files ========================= */
```

```c
#include "mlc.h"

/* ======================= function name ======================= */ int MLCfit (points, npoints)

/* ========================= comments ========================== */
/*
Checks contour fits in mlc
*/
/* ======================== declarations ======================= */
/*
type       parameter     i/o      description
---------  ------------  -------  ---------------------------------
point      *points;      /* i     array of contour points          */
int        npoints;      /* i     number of contour points         */

/* ============================ log ============================ */
/*
return status description
---------------  --------------------------------------------------
 1               Success - fit
-1               Failure
 0               Contour does not fit in mlc date       comments
--------   --------------------------------------------------------
07/17/92   Creation - Jeremy Wong
*/
/* ============================================================= */

{ int i;
double minx, maxx, miny, maxy;

/*
   check contour fits in mlc
*/ maxx = MAXLEAFx;
minx = MINLEAFx;
maxy = MAXLEAFy;
miny = MINLEAFy;
for ( i = 0; i < npoints; i++ ) {
   if ( (points[i].x > maxx) || (points[i].x < minx) ||
        (points[i].y > maxy) || (points[i].y < miny) ) {
      fputs ("MLCfit: contour does not fit in mlc\n", stderr);
      return (0);
   }
} return (1);

ERROR_RETURN:
fputs ("Error: MLCfit\n", stderr);
return (-1);

}
```

```
mlcinlef.c
/* ========================= include files ========================= */ include <stdio.h>
include "mlc.h"

/* ========================= function name ========================= */ int MLCinleaf (filename, ngantry, leaf_area, average)

/* ========================= comments ========================= */
/*
Reads leaf insertions from MLC file
*/
/* ========================= declarations ========================= */
/*
type       parameter      i/o       description
---------  -------------  --------  ----------------------------------------*/
char       *filename;     /* i      filename                                */
int        ngantry;       /* i      number of gantry angles read            */
int        *leaf_area;    /* o      leaf areas                              */
int        *average;      /* o      leaf averages                           */

/* ========================= log ========================= */
/*
return status description
---------------  ----------------------------------------------------------
 1               Success
-1               Failure date       comments
--------   ----------------------------------------------------------
07/17/92   Creation - Jeremy Wong
*/
/* ========================================================================= */

{

FILE *fp = NULL, *fopen();
int i, max, num, num1;
char fname[128], str[180];

/*
   open MLC leaf area file
*/

SYSbufinit (fname, 0, sizeof (fname));
strcat (fname, filename);
strcat (fname, ".lfa");
fp = fopen (fname, "r");
if ( fp == NULL ) goto ERROR_RETURN;

/*
   read MLC leaf area file
*/ max = 160;
fgets (str, max, fp); /* File Rev */
fgets (str, max, fp); /* Last Name */
fgets (str, max, fp); /* First Name */
```

```
fgets (str, max, fp); /* Patient ID */

SYSbufinit (str, 0, sizeof (str));
fgets (str, max, fp); /* Number of Fields */
sscanf (str, "Number of Fields = %d", &num);
if ( num != ngantry ) return -1;
fgets (str, max, fp); /*    */ for ( i = 0; i < ngantry; i++ ) {
   SYSbufinit (str, 0, sizeof (str));
   fgets (str, max, fp); /* Leaf Insertion */
   sscanf (str, "Leaf Insertion (%%) = %d,   Leaf Average = %d", &num,
           &num1);
   leaf_area[i] = num;
   average[i] = num1;
}

/*
   close MLC leaf area file
*/ fclose (fp);

return (1);

ERROR_RETURN:
fputs ("Error: MLCinleaf\n", stderr);
return (-1);

} mlcinmlc.c
/* ========================= include files ========================= */ include <stdio.h>
include "mlc.h"

/* ========================= function name ========================= */ int MLCinmlc (filename, ngantry, pt_left, pt_right, rotation, stat,
              lname, fname, pid)

/* ========================= comments ========================= */
/*
Reads leaf coordinates from MLC file
*/
/* ========================= declarations ========================= */
/*
type       parameter      i/o     description
---------- -------------  ------- -----------------------------------*/
char       *filename;     /* i    filename                          */
int        ngantry;       /* i    number of gantry angles read      */
point pt_left[][NLEAF-1]; /*o     coordinates of left leaves        */
point pt_right[][NLEAF-1];/*o     coordinates of right leaves       */
int        *rotation;     /* o    rotation angle of contour         */
int        stat[];        /* o    whether leaves set                */
char       *lname;        /* o    last name                         */
char       *fname;        /* o    first name                        */
char       *pid;          /* o    pid                               */
```

```
/* ========================= log ========================= */
/*
return status description
--------------- ----------------------------------------------
 1              Success
-1              Failure date       comments
--------   ----------------------------------------------------
07/17/92   Creation - Jeremy Wong
 */
/* ====================================================== */

{

FILE *fp = NULL, *fopen();
int i, j, max, num;
double f;
char str[180];

/*
   open MLC file
*/ fp = fopen (filename, "r");
if ( fp == NULL ) goto ERROR_RETURN;

/*
   read MLC file
*/ max = 160;
fgets (str, max, fp); /* File Rev */

SYSbufinit (str, 0, sizeof (str));
fgets (str, max, fp); /* Last Name */
sscanf (str, "Last Name = %s", lname);

SYSbufinit (str, 0, sizeof (str));
fgets (str, max, fp); /* First Name */
sscanf (str, "First Name = %s", fname);

SYSbufinit (str, 0, sizeof (str));
fgets (str, max, fp); /* Patient ID */
sscanf (str, "Patient ID = %s", pid);

SYSbufinit (str, 0, sizeof (str));
fgets (str, max, fp); /* Number of Fields */
sscanf (str, "Number of Fields = %d", &num);
if ( num != ngantry ) return -1;

for ( i = 0; i < ngantry; i++ ) {
   fgets (str, max, fp); /*    */
   fgets (str, max, fp); /* Field */
   fgets (str, max, fp); /* Treatment Count */
   fgets (str, max, fp); /* Operator */

SYSbufinit (str, 0, sizeof (str));
   fgets (str, max, fp); /* Collimator */
   sscanf (str, "Collimator = %d", &num);
```

```
   rotation[i] = mlc_ext_int_rot (num);
   fgets (str, max, fp); /* Gantry */
/*

*/ for ( j = 0; j < (NLEAF-1); j++ ) {
      SYSbufinit (str, 0, sizeof (str));
      fgets (str, max, fp);
      sscanf (str, "Leaf %dA = %lf", &num, &f);
      if ( f <= 0. )
         f /= LSLEAF;
      else if ( f > 0. )
         f /= CSLEAF;
      pt_left[i][j].x = f;
   } for ( j = 0; j < (NLEAF-1); j++ ) {
      SYSbufinit (str, 0, sizeof (str));
      fgets (str, max, fp);
      sscanf (str, "Leaf %dB = %lf", &num, &f);
      if ( f >= 0. )
         f /= RSLEAF;
      else if ( f < 0. )
         f /= CSLEAF;
      pt_right[i][j].x = f;
   }
   fgets (str, max, fp); /* Note */
   fgets (str, max, fp); /* Shape */
   fgets (str, max, fp); /* Magnification */
   stat[i] = 1;
}

/*
   close MLC file
*/ fclose (fp);

return (1);

ERROR_RETURN:
fputs ("Error: MLCinmlc\n", stderr);
return (-1);

} mlcinput.c
/* ======================= include files ======================= */ include <stdio.h>
include "mlc.h"

/* ======================= function name ======================= */ int MLCinput (filename, gantry, ngantry, gpoints, ngpoints)

/* ======================= comments ======================= */
/*
```

```
Reads input file of contour points
*/
/* ========================= declarations ======================== */
/*
type        parameter       i/o     description
--------    ------------    ---     ------------------------------------*/
char        *filename;      /* i    filename                            */
int         gantry[];       /* o    gantry angles read                  */
int         *ngantry;       /* o    number of gantry angles read        */
point*gpoints[NGANTRY];/* o         array of points/gantry angle read   */
int         ngpoints[]  ;/* o       number of points/gantry angle read  */

/* ============================ log ============================ */
/*
return status description
--------------- ------------------------------------------------------
 1              Success
-1              Failure date        comments
--------    ------------------------------------------------------
07/17/92    Creation - Jeremy Wong
*/
/* ================================================================ */

{

FILE *fp = NULL, *fopen();
int i, max, size, pts;
double f1, f2;
char str[100];

/*
   open input file
*/ fp = fopen (filename, "r");
if ( fp == NULL ) goto ERROR_RETURN;

/*
   read file
*/

*ngantry = 0;
for ( i = 0; i < NGANTRY; i++ ) {
   gantry[i] = 0;
   ngpoints[i] = 0;
   gpoints[i] = NULL;
}
max = 80;
SYSbufinit (str, 0, sizeof (str));
while ( fgets (str, max, fp) != NULL ) {
   if ( MLCsearch (str, &i) == 1 ) {
      gantry[*ngantry] = i;
      ngpoints[*ngantry] = 0;
      (*ngantry)++;
   }
   else if ( MLCsearch (str, &i) == 2 ) {
      sscanf (str, "%d %lf %lf", &pts, &f1, &f2);
      size = sizeof (point) * (ngpoints[*ngantry-1] + 1);
```

```
        if ( ngpoints[*ngantry-1] == 0 ) {
            gpoints[*ngantry-1] = (point *) malloc (size);
            if ( gpoints[*ngantry-1] == NULL ) goto ERROR_RETURN;
        }
        else {
            gpoints[*ngantry-1] = (point *) realloc (gpoints[*ngantry-1],
                                                    size);
            if ( gpoints[*ngantry-1] == NULL ) goto ERROR_RETURN;
        } gpoints[*ngantry-1][ngpoints[*ngantry-1]].x = f1 /* * SLEAF */;
        gpoints[*ngantry-1][ngpoints[*ngantry-1]].y = f2 /* * SLEAF */;
        ngpoints[*ngantry-1]++;
    }
    SYSbufinit (str, 0, sizeof (str));
}

/*
    close input file
*/ fclose (fp);

return (1);

ERROR_RETURN:
fputs ("Error: MLCinput\n", stderr);
return (-1);

}

/* ======================= include files ======================= */

/* ======================= function name ======================= */ int MLCsearch (str, num)

/* ======================= comments ======================= */
/*
Search input line for gantry angle/contour point
*/
/* ======================= declarations ======================= */
/*
type        parameter    i/o        description
---------   -----------  ---------  ------------------------------------*/
char        *str;        /* i       input line                          */
int         *num;        /* o       gantry angle                        */

/* ======================= log ======================= */
/*
return status description
-------------   ------------------------------------------------------
0               Failure
1               Success - gantry angle
2               Success - contour point date        comments
--------    ------------------------------------------------------
```

```
07/17/92    Creation - Jeremy Wong
 */
/* =================================================================== */

{ int i, pts;
double f1, f2;

/*
    search for gantry angle/contour point
*/ if ( strstr (str, "Gantry") ) {
    i = 0;
    while ( str[i] != '=' )
        i++;
    i++;
    sscanf (&str[i], "%d", num);

return (1);
}
else if ( sscanf (str, "%d %lf %lf", &pts, &f1, &f2) == 3 ) {
    return (2);
}
else
    return (0);

} mlcleaf.c
/* ======================= include files ======================= */ include "mlc.h"

/* ======================= function name ======================= */ int MLCleaf (pts1, pts2, pt1, pt2, found, pt)

/* ======================= comments ======================= */
/*
Finds intersection point of 1 leaf and 1 contour
 */
/* ======================= declarations ======================= */
/*
type        parameter    i/o        description
---------   -----------  -------    ---------------------------------------*/
point       *pts1;       /* i       coordinates of leaf line                */
point       *pts2;       /* i                                               */
point       *pt1;        /* i       coordinates of contour line             */
point       *pt2;        /* i                                               */
int         *found;      /* o       existence of intersection point         */
point       *pt;         /* o       coordinates of intersection point       */

/* ======================= log ======================= */
/*
return status description
-------------   ---------------------------------------------
  1             Success
 -1             Failure
```

```
date       comments
--------   -----------------------------------------------------------
07/17/92   Creation - Jeremy Wong
 */
/* ================================================================ */

{ double a1, b1, c1, a2, b2, c2, det, fabs();
point p, p1, p2;

/*
   find intersection point
*/ pt->x = 0.;
pt->y = 0.;
*found = 0;
if ( (fabs (pt1->x - pt2->x) < CLOSELEAF) &&    /* same contour points */
     (fabs (pt1->y - pt2->y) < CLOSELEAF) ) {
   *found = 0;
}
else {
   a1 = pts1->y - pts2->y;
   b1 = pts2->x - pts1->x;
   c1 = (pts1->x * pts2->y) - (pts2->x * pts1->y);

a2 = pt1->y - pt2->y;
   b2 = pt2->x - pt1->x;
   c2 = (pt1->x * pt2->y) - (pt2->x * pt1->y);

det = (a1 * b2) - (a2 * b1);
   if ( fabs (det) < CLOSELEAF ) {    /* lines are parallel */
      *found = 0;
   }
   else {
      p.x = (1 / det) * ((-1 * c1 * b2) + (c2 * b1));
      p.y = (1 / det) * ((-1 * c2 * a1) + (c1 * a2));

if ( pt1->x > pt2->x ) {
         p1.x = pt2->x;
         p2.x = pt1->x;
      }
      else {
         p1.x = pt1->x;
         p2.x = pt2->x;
      }
      if ( pt1->y > pt2->y ) {
         p1.y = pt2->y;
         p2.y = pt1->y;
      }
      else {
         p1.y = pt1->y;
         p2.y = pt2->y;
      } if ( (p.x >= (p1.x - CLOSELEAF)) &&
           (p.x <= (p2.x + CLOSELEAF)) &&
           (p.y >= (p1.y - CLOSELEAF)) &&
```

```
              (p.y <= (p2.y + CLOSELEAF)) ) {
          /*if ( p.x > MAXLEAFx )
              p.x = MAXLEAFx;
          else if ( p.x < MINLEAFx )
              p.x = MINLEAFx;*/ pt->x = p.x;
          pt->y = p.y;
          *found = 1;
        }
    }
} return (1);

ERROR_RETURN:
fputs ("Error: MLCleaf\n", stderr);
return (-1);

} mlcleves.c
/* ======================= include files ======================= */ include "mlc.h"

/* ======================= function name ======================= */ int MLCleaves (points, npoints, rotation, leaf_area, average, pt_left,
               pt_right)

/* ======================= comments ======================= */
/*
Finds intersection points of leaves and contour points
*/
/* ======================= declarations ======================= */
/*
type       parameter     i/o     description
---------  ------------  ------  -----------------------------------------*/
point      *points;      /* i    array of contour points                 */
int        npoints;      /* i    number of contour points                */
int        rotation;     /* i    collimator angle rotation               */
int        leaf_area;    /* i    percent leaf area inserted              */
int        average;      /* i    leaf average                            */
point      *pt_left;     /* o    coordinates of left leaves              */
point      *pt_right;    /* o    coordinates of right leaves             */

/* ======================= log ======================= */
/*
return status description
--------------  ----------------------------------------------
 1              Success
-1              Failure date       comments
--------   ----------------------------------------------
07/17/92   Creation - Jeremy Wong
*/
/* ============================================================ */
```

```
{
   int i, j, found, first, count, pt_found[((NLEAF-1)*MLEAF)+1];
   point pts1, pts2, pt1, pt2, pta, ptb, ptc, pt,
         pt_min[((NLEAF-1)*MLEAF)+1], pt_max[((NLEAF-1)*MLEAF)+1];
   double minl, maxl, minr, maxr;
   double MLCmin(), MLCmax();
   int mleaf;
   double incrmleaf;
   point mlc_rot(), mlc_inv_rot();

/*
      find intersection points
   */ if ( average == 3 ) {
      mleaf = 2;
      incrmleaf = 0.2;
   }
   else if ( average == 5 ) {
      mleaf = 4;
      incrmleaf = 0.1;
   }
   pts1.x = MINLEAFx;
   pts1.y = MINLEAFy;
   pts2.x = MAXLEAFx;
   pts2.y = MINLEAFy;
   for ( i = 0; i <= (NLEAF - 1) * mleaf; i++ ) {
      pt_min[i].x = 0.;
      pt_max[i].x = 0.;
      pt_found[i] = 0;
      first = 1;
      for ( j = 0; j < npoints; j++ ) {
         pt1.x = points[j].x;
         pt1.y = points[j].y;
         if ( (j == npoints - 1) ) {
            pt2.x = points[0].x;
            pt2.y = points[0].y;
         }
         else {
            pt2.x = points[j+1].x;
            pt2.y = points[j+1].y;
         } pta = mlc_rot (rotation, pts1);
         ptb = mlc_rot (rotation, pts2);
         MLCleaf (&pta, &ptb, &pt1, &pt2, &found, &ptc);
         pt = mlc_inv_rot (rotation, ptc);

if ( found ) {
            pt_found[i] = 1;
            if ( first ) {
               pt_min[i].x = pt.x;
               pt_max[i].x = pt.x;
               first = 0;
            }
            else {
               if ( pt.x < pt_min[i].x )
                  pt_min[i].x = pt.x;
               if ( pt.x > pt_max[i].x )
```

```
                pt_max[i].x = pt.x;
            }
        }
    }
    pts1.y += incrmleaf;
    pts2.y += incrmleaf;
}

/*
    find leaf position
*/
for ( i = 0; i < (NLEAF-1); i++ ) {
    pt_left[i].x = 0.;
    pt_right[i].x = 0.;

minl = MLCmin (&pt_min[i*mleaf], &pt_found[i*mleaf], mleaf);
    maxl = MLCmax (&pt_min[i*mleaf], &pt_found[i*mleaf], mleaf);
    minr = MLCmax (&pt_max[i*mleaf], &pt_found[i*mleaf], mleaf);
    maxr = MLCmin (&pt_max[i*mleaf], &pt_found[i*mleaf], mleaf);

pt_left[i].x = ((maxl*leaf_area) + (minl*(100.-leaf_area)))/100.;
    pt_right[i].x = ((maxr*leaf_area) + (minr*(100.-leaf_area)))/100.;

if ( pt_left[i].x > MAXLEAFx )
        pt_left[i].x = MAXLEAFx;
    else if ( pt_left[i].x < MINLEAFx )
        pt_left[i].x = MINLEAFx;
    if ( pt_right[i].x > MAXLEAFx )
        pt_right[i].x = MAXLEAFx;
    else if ( pt_right[i].x < MINLEAFx )
        pt_right[i].x = MINLEAFx;
/*
    if ( pt_found[i*mleaf] && pt_found[(i*mleaf)+mleaf] ) {
        pt_left[i].x = ((maxl*leaf_area) + (minl*(100.-leaf_area)))/100.;
        pt_right[i].x = ((maxr*leaf_area) + (minr*(100.-leaf_area)))/100.;
    }
    else if ( pt_found[i*mleaf] && !pt_found[(i*mleaf)+mleaf] ) {
        pt_left[i].x = minl;
        pt_right[i].x = minr;
    }
    else if ( !pt_found[i*mleaf] && pt_found[(i*mleaf)+mleaf] ) {
        pt_left[i].x = minl;
        pt_right[i].x = minr;
    }
*/
} return (1);

ERROR_RETURN:
fputs ("Error: MLCleaves\n", stderr);
return (-1);

}

/* ======================= include files ======================= */

/* ======================= function name ======================= */
```

```
double MLCmin (pt_points, pt_found, num_pt)

/* ========================== comments ========================== */
/*
Finds minimum point of intersection of leaves and contour points
 */
/* ========================== declarations ========================== */
/*
type       parameter    i/o     description
---------  -----------  ------  ---------------------------------------*/
point      *pt_points;  /* i    array of intersection points         */
int        *pt_found;   /* i    whether point valid                  */
int        num_pt;      /* i    number of points to check            */

/* ============================ log ============================ */
/*
return status description
----------- -----------------------------------------------------------
 1          Success
-1          Failure date       comments
--------   -----------------------------------------------------------
07/17/92   Creation - Jeremy Wong
 */
/* ============================================================== */

{
int i, j;
double min;

j = 0;
while ( !pt_found[j] && (j <= num_pt) ) {
   j++;
} if ( j <= num_pt ) {
   min = pt_points[j].x;
   for ( i = j; i <= num_pt; i++ ) {
      if ( (pt_found[i]) && (min > pt_points[i].x) )
         min = pt_points[i].x;
   }
}
else
   min = 0.;

return min;

ERROR_RETURN:
fputs ("Error: MLCmin\n", stderr);
return (-1);

}

/* ========================== include files ========================== */

/* ========================== function name ========================== */ double MLCmax (pt_points, pt_found, num_pt)
```

```
/* ========================= comments ========================= */
/*
Finds maximum point of intersection of leaves and contour points
*/
/* ========================= declarations ========================= */
/*
type       parameter      i/o      description
--------   ------------   ------   ------------------------------------*/
point      *pt_points;    /* i     array of intersection points        */
int        *pt_found;     /* i     whether point valid                 */
int        num_pt;        /* i     number of points to check           */

/* ========================= log ========================= */
/*
return status description
---------------  ------------------------------------------------------
 1               Success
-1               Failure date      comments
--------  ------------------------------------------------------------
07/17/92  Creation - Jeremy Wong
*/
/* ================================================================== */

{ int i, j;
double max;

j = 0;
while ( !pt_found[j] && (j <= num_pt) ) {
   j++;
} if ( j <= num_pt ) {
   max = pt_points[j].x;
   for ( i = j; i <= num_pt; i++ ) {
      if ( (pt_found[i]) && (max < pt_points[i].x) )
         max = pt_points[i].x;
   }
}
else
   max = 0.;

return max;

ERROR_RETURN:
fputs ("Error: MLCmax\n", stderr);
return (-1);

} mlcout.c
/* ========================= include files ========================= */ include <stdio.h>
include "mlc.h"
```

```
/* ===================== function name ===================== */
int MLCout (filename, ngantry, beam, gantry, pt_left, pt_right,
            rotation, shift_x, shift_y, field, lname, fname, pid)
/* ========================= comments ====================== */
/*
Writes leaf coordinates to output file
*/
/* ======================== declarations =================== */
/*
type        parameter    i/o      description
---------   -----------  ------   -----------------------------------*/
char        *filename;   /* i     filename                           */
int         ngantry;     /* i     number of gantry to output         */
int         beam;        /* i     beam to output                     */
int         *gantry;     /* i     gantry angles                      */
point pt_left[][NLEAF-1]; /*i     coordinates of left leaves         */
point pt_right[][NLEAF-1];/*i     coordinates of right leaves        */
int         *rotation;   /* i     rotation angle of contour          */
double      shift_x;     /* i     x shift of contour                 */
double      shift_y;     /* i     y shift of contour                 */
char field[][FIELDNAME];/*i       field names to output              */
char        *lname;      /* i     last name                          */
char        *fname;      /* i     first name                         */
char        *pid;        /* i     pid                                */
                                                                    /*
/* =========================== log ========================= */
/*
return status description
--------------- ------------------------------------------------------
1              Success
-1             Failure date      comments
--------  ------------------------------------------------------------
07/17/92  Creation - Jeremy Wong
 */
/* ========================================================= */

{

FILE *fp = NULL, *fopen();
char tname[128];
int i, j;
double f;

/*
   open output file
*/

SYSbufinit (tname, 0, sizeof (tname));
strcat (tname, filename);
strcat (tname, ".tmp");
fp = fopen (tname, "w");
if ( fp == NULL ) goto ERROR_RETURN;

/*
   write to file
*/
```

```c
    fprintf (fp,"File Rev = C\r\n");
    fprintf (fp,"Last Name = %s\r\n", lname);
    fprintf (fp,"First Name = %s\r\n", fname);
    fprintf (fp,"Patient ID = %s\r\n", pid);
    fprintf (fp,"Number of Fields = 1\r\n");
    /*fprintf (fp,"Number of Fields = %d\r\n", ngantry);*/ i = beam;
    /*for ( i = 0; i < ngantry; i++ ) {*/
        fprintf (fp,"\r\n");
        fprintf (fp,"Field = 1\r\n");
        /*fprintf (fp,"Field = %d\r\n", i+1);*/
        fprintf (fp,"Treatment Count = 1\r\n");
        fprintf (fp,"Operator = Tech\r\n");
        fprintf (fp,"Collimator = %d\r\n", mlc_int_ext_rot (rotation[i]));
        fprintf (fp,"Gantry = %d\r\n", gantry[i]);
/*

*/ for ( j = 0; j < (NLEAF-1); j++ ) {
        /*if ( pt_left[i][j].x < 0. )
            f = -1. * pt_left[i][j].x;
        else if ( pt_left[i][j].x > 0. )
            f = -1. * pt_left[i][j].x;
        else
            f = pt_left[i][j].x;*/ if ( pt_left[i][j].x <= 0.)
            f = pt_left[i][j].x * LSLEAF;
        else if ( pt_left[i][j].x > 0.)
            f = pt_left[i][j].x * CSLEAF;

fprintf (fp, "Leaf %2dA =    %6.3f\r\n", j+1, f);
    } for ( j = 0; j < (NLEAF-1); j++ ) {
        /*if ( pt_right[i][j].x < 0. )
            f = pt_right[i][j].x;
        else if ( pt_right[i][j].x > 0. )
            f = pt_right[i][j].x;
        else
            f = pt_right[i][j].x;*/ if ( pt_right[i][j].x >= 0.)
            f = pt_right[i][j].x * RSLEAF;
        else if ( pt_right[i][j].x < 0.)
            f = pt_right[i][j].x * CSLEAF;

fprintf (fp, "Leaf %2dB =    %6.3f\r\n", j+1, f);
    } fprintf (fp,"Note = 0\r\n");
    fprintf (fp,"Shape = 0\r\n");
    fprintf (fp,"Magnification = 0\r\n");
/*}*/

/*
```

```
   close output file
*/ fclose (fp);

return (1);

ERROR_RETURN:
fputs ("Error: MLCout\n", stderr);
return (-1);

} mlcoutlf.c
/* ==================== include files ==================== */ include <stdio.h>
include "mlc.h"

/* ==================== function name ==================== */ int MLCoutleaf (filename, ngantry, leaf_area, average, lname, fname,
                pid)

/* ==================== comments ==================== */
/*
Writes leaf insertions to output file
 */
/* ==================== declarations ==================== */
/*
type      parameter    i/o      description
--------  ------------ -------- ----------------------------------------*/
char      *filename;   /* i     filename                               */
int       ngantry;     /* i     number of gantry to output              */
int       *leaf_area;  /* i     leaf areas                             */
int       *average;    /* i     leaf averages                          */
char      *lname;      /* i     last name                              */
char      *fname;      /* i     first name                             */
char      *pid;        /* i     pid                                    */

/* ==================== log ==================== */
/*
return status description
--------------- -----------------------------------------------------
1          Success
-1         Failure date      comments
--------  -----------------------------------------------------------
07/17/92  Creation - Jeremy Wong
 */
/* ============================================================== */

{

FILE *fp = NULL, *fopen();
int i;
char ffname[128];

/*
```

```
   open MLC leaf area file
*/

SYSbufinit (ffname, 0, sizeof (ffname));
strcat (ffname, filename);
strcat (ffname, ".lfa");
fp = fopen (ffname, "w");
if ( fp == NULL ) goto ERROR_RETURN;

/*
   write to MLC leaf area file
*/ fprintf (fp, "File Rev = C\r\n");
fprintf (fp, "Last Name = %s\r\n", lname);
fprintf (fp, "First Name = %s\r\n", fname);
fprintf (fp, "Patient ID = %s\r\n", pid);
fprintf (fp, "Number of Fields = %d\r\n", ngantry);
fprintf (fp, "\r\n");

for ( i = 0; i < ngantry; i++ ) {
   fprintf (fp, "Leaf Insertion (%%) = %3d,   ", leaf_area[i]);
   fprintf (fp, "Leaf Average = %d\r\n", average[i]);
}

/*
   close MLC leaf area file
*/ fclose (fp);

return (1);

ERROR_RETURN:
fputs ("Error: MLCoutleaf\n", stderr);
return (-1);

} mlcoutpt.c
/* ========================= include files ========================= */ include <stdio.h>
include "mlc.h"

/* ========================= function name ========================= */ int MLCoutput (filename, ngantry, gantry, pt_left, pt_right, rotation,
               shift_x, shift_y, field, lname, fname, pid)

/* ========================= comments ========================= */
/*
Writes leaf coordinates to output file
*/
/* ========================= declarations ========================= */
/*
type       parameter     i/o      description
---------  ------------  -------  ----------------------------------------*/
char       *filename;    /* i     filename                                */
int        ngantry;      /* i     number of gantry to output              */
```

```
int       *gantry;              /* i    gantry angles                      */
point pt_left[][NLEAF-1];       /*i     coordinates of left leaves         */
point pt_right[][NLEAF-1];      /*i     coordinates of right leaves        */
int       *rotation;            /* i    rotation angle of contour          */
double    shift_x;              /* i    x shift of contour                 */
double    shift_y;              /* i    y shift of contour                 */
char      field[][FIELDNAME];   /*i     field names to output              */
char      *lname;               /* i    last name                          */
char      *fname;               /* i    first name                         */
char      *pid;                 /* i    pid                                */

/* =============================== log =============================== */
/*
return status   description
-------------   -----------
 1              Success
-1              Failure date        comments
--------    --------
07/17/92    Creation - Jeremy Wong
 */
/* ================================================================== */

{

FILE *fp = NULL, *fopen();
int i, j;
double f;

/*
   open output file
*/ fp = fopen (filename, "w");
if ( fp == NULL ) goto ERROR_RETURN;

/*
   write to file
*/ fprintf (fp,"File Rev = C\r\n");
fprintf (fp,"Last Name = %s\r\n", lname);
fprintf (fp,"First Name = %s\r\n", fname);
fprintf (fp,"Patient ID = %s\r\n", pid);
fprintf (fp,"Number of Fields = %d\r\n", ngantry);

for ( i = 0; i < ngantry; i++ ) {
   fprintf (fp,"\r\n");
   fprintf (fp,"Field = %d\r\n", i+1);
   fprintf (fp,"Treatment Count = 1\r\n");
   fprintf (fp,"Operator = Tech\r\n");
   fprintf (fp,"Collimator = %d\r\n", mlc_int_ext_rot (rotation[i]));
   fprintf (fp,"Gantry = %d\r\n", gantry[i]);

/*

*/ for ( j = 0; j < (NLEAF-1); j++ ) {
```

```c
        /*if ( pt_left[i][j].x < 0. )
            f = -1. * pt_left[i][j].x;
        else if ( pt_left[i][j].x > 0. )
            f = -1. * pt_left[i][j].x;
        else
            f = pt_left[i][j].x;*/ if ( pt_left[i][j].x <= 0.)
            f = pt_left[i][j].x * LSLEAF;
        else if ( pt_left[i][j].x > 0.)
            f = pt_left[i][j].x * CSLEAF;

fprintf (fp, "Leaf %2dA =   %6.3f\r\n", j+1, f);
    } for ( j = 0; j < (NLEAF-1); j++ ) {
        /*if ( pt_right[i][j].x < 0. )
            f = pt_right[i][j].x;
        else if ( pt_right[i][j].x > 0. )
            f = pt_right[i][j].x;
        else
            f = pt_right[i][j].x;*/ if ( pt_right[i][j].x >= 0.)
            f = pt_right[i][j].x * RSLEAF;
        else if ( pt_right[i][j].x < 0.)
            f = pt_right[i][j].x * CSLEAF;

fprintf (fp, "Leaf %2dB =   %6.3f\r\n", j+1, f);
    } fprintf (fp,"Note = 0\r\n");
    fprintf (fp,"Shape = 0\r\n");
    fprintf (fp,"Magnification = 0\r\n");
}
/*
   close output file
*/ fclose (fp);

return (1);

ERROR_RETURN:
fputs ("Error: MLCoutput\n", stderr);
return (-1);

}

MMLC CONTROL PROGRAM
misc.c
/* ======================= include files ======================= */ include "mlcv.h"
include <stdio.h>
```

```
/* ======================== function name ======================== */ int SYSbufinit (buf, offset, size)

/* ========================== comments ========================== */
/*
Initializes a buffer.
 */
/* ========================= declarations ========================= */
/*
type      parameter     i/o      description
--------  -----------   -----    ------------------------------------*/
char      *buf;         /* i/o   buffer                              */
int       offset;       /* i     offset in bytes to start of buffer  */
int       size;         /* i     number of bytes to initialize       */

/* ============================= log ============================= */
/*
return status description
---------------  ------------------------------------------------
 1        Success
-1        Failure date      comments
--------  ------------------------------------------------
04/30/92  Creation - Jeremy Wong
 */
/* ============================================================== */

{ int i, j;

if ( buf == NULL ) goto ERROR_RETURN;

for ( i = offset, j = 0; j < size; i++, j++ ) buf[i] = 0;

return (1);

ERROR_RETURN:
fputs ("Error: SYSbufinit\n", stderr);
return (-1);

} mlcv.c
/* ======================= include files ======================= */ include "mlcv.h"

/* ======================= function name ======================= */ void main (argc, argv)

/* ======================== comments ======================== */
/*
MLC program
 */
/* ======================== declarations ======================== */
/*
```

```
type        parameter   i/o     description
--------    ----------  -----   -----------------------------------------*/
int         argc;       /* i    argument count                           */
char        **argv;     /* i    program arguments                        */

/* ============================== log ================================== */
/*
return status  description
-------------  -----------
 1             Success
-1             Failure date       comments
--------   --------
08/10/93   Creation - Jeremy Wong
 */
/* ===================================================================== */

{ int status, i;
char str[128];
mlc_vobjects *vobjects = NULL;

/*
   initialize mlc parameters
*/ status = MLCVinit (&vobjects);
if ( status != 1 ) goto ERROR_EXIT;

status = MLCVapos (vobjects->hndle,
                   vobjects->node_left, vobjects->node_right,
                   vobjects->old_left, vobjects->old_right);
if ( status != 1 ) goto ERROR_EXIT;

/*
   read input file of leaf positions
*/

SYSbufinit (vobjects->leaf_file, 0, sizeof (vobjects->leaf_file));
strcpy (vobjects->leaf_file, argv[1]);
status = MLCVinpt (vobjects->leaf_file, &vobjects->ngantry,
                   vobjects->leaf_left, vobjects->leaf_right);
if ( status != 1 ) goto ERROR_EXIT;

/*
   mlc loop
*/ for ( i = 0; i < vobjects->ngantry; i++ ) {
   status = MLCVleaf (vobjects->hndle,
                      vobjects->node_left, vobjects->node_right,
                      vobjects->leaf_left[i], vobjects->leaf_right[i],
                      vobjects->pos_left, vobjects->pos_right,
                      vobjects->old_left, vobjects->old_right,
                      vobjects->zero_left, vobjects->zero_right,
                      vobjects->oldc_left, vobjects->oldc_right,
                      vobjects->count_left, vobjects->count_right,
                      vobjects->spkt, 1);
```

```
    if ( status != 1 ) goto ERROR_EXIT;
    printf ("Next> ");
    scanf ("%s", str);
} status = MLCVopen (vobjects->hndle,
                   vobjects->node_left, vobjects->node_right,
                   vobjects->leaf_left[0], vobjects->leaf_right[0],
                   vobjects->pos_left, vobjects->pos_right,
                   vobjects->old_left, vobjects->old_right,
                   vobjects->zero_left, vobjects->zero_right,
                   vobjects->oldc_left, vobjects->oldc_right,
                   vobjects->count_left, vobjects->count_right,
                   vobjects->spkt);
if ( status != 1 ) goto ERROR_EXIT;

free (vobjects);
exit (1);

ERROR_EXIT:
fputs ("Error: MLCV\n", stderr);
exit (-1);

} mlcv.h
/* ======================= include files ======================= */

/* ======================= include name ======================= */ include <stdio.h>
include "port.h"
#include "api_c.h"

/* ======================= comments ======================= */
/*
mlcv
 */
/* ======================= log ======================= */
/*
date       comments
--------   -----------------------------------------------------
08/10/93   Creation - Jeremy Wong
 */
/* ============================================================= */ ifndef MLCV
define MLCV define NGANTRY        50     /* maximum number of gantry angles */
define NVANE          15     /* number of vanes for each side */
#define TOL            50     /* counts of deadband tolerance */
#define COUNT_PER_MM   608    /* counts per mm. */
#define COUNT_PER_SEC  250    /* counts per sec. */
define CLOSELEAF      1.e-6  /* error correction */ typedef struct {

HANDLE hndle;                            /* parvus port handle */
```

```
int node_left[NVANE], node_right[NVANE];    /* parvus node numbers */
int ngantry;                                /* number of gantry angles */
double leaf_left[NGANTRY][NVANE];           /* left leaf positions */
double leaf_right[NGANTRY][NVANE];          /* right leaf positions */
long pos_left[NVANE], pos_right[NVANE];     /* current vane positions */
long old_left[NVANE], old_right[NVANE];     /* previous vane positions */
long zero_left[NVANE], zero_right[NVANE];   /* counts to (0,0) */
long oldc_left[NVANE], oldc_right[NVANE];   /* previous poten. counts */
long open_left[NVANE], open_right[NVANE];   /* potentiometer counts */
long close_left[NVANE], close_right[NVANE];/* at open/close positions */
double count_left[NVANE], count_right[NVANE];/* potent. counts per cm.*/
UINT8 spkt[20];                             /* sample packet */
char leaf_file[128];                        /* input filename */

} mlc_vobjects;

endif /* MLCV */ mlcvapos.c
/* ========================= include files ========================= */ include "mlcv.h"
include <time.h>

/* ========================= function name ========================= */ int MLCVapos (hndle, node_left, node_right, old_left, old_right)

/* ========================= comments ========================= */
/*
Sends packets to get actual leaf positions
*/
/* ========================= declarations ========================= */
/*
type       parameter      i/o      description
---------  -------------  -------  ----------------------------------*/
HANDLE     hndle;         /* i     handle                            */
int        node_left[];   /* i     vane node numbers                 */
int        node_right[];  /* i     for left and right leaves         */
long       old_left[];    /* i     old vane movement positions       */
long       old_right[];   /* i     for left and right leaf positions */

/* ============================= log ============================= */
/*
return status description
--------------- ---------------------------------------------------
 1              Success
-1              Failure date      comments
--------  ---------------------------------------------------------
08/10/93  Creation - Jeremy Wong
*/
/* ================================================================ */

{ int status, i, start, end;
```

```c
clock_t timer, interval;

/*
   send packets to get actual leaf positions
*/ start = 0;
end = NVANE;
/*
status = MLCVmap (hndle, node_left, node_right, start, end);
if ( status != 1 ) goto ERROR_RETURN;
MLCVwait (1.);
*/
status = MLCVreq (hndle, 30, node_left, node_right, start, end);
if ( status != 1 ) goto ERROR_RETURN;
MLCVwait (1.);

timer = clock ();
interval = 1;
for ( i = 0; i < NVANE; i++ ) {
   status = MLCVstat (hndle, 0, 30, i+1, node_left[i], timer, interval);
   if ( status != 1 ) goto ERROR_RETURN;
   status = MLCVget (hndle, i+1, node_left[i], &old_left[i]);
   if ( status != 1 ) goto ERROR_RETURN;

status = MLCVstat (hndle, 0, 30, i+17, node_right[i], timer,
                     interval);
   if ( status != 1 ) goto ERROR_RETURN;
   status = MLCVget (hndle, i+17, node_right[i], &old_right[i]);
   if ( status != 1 ) goto ERROR_RETURN;
} return (1);

ERROR_RETURN:
fputs ("Error: MLCVapos\n", stderr);
return (-1);

} mlcvc.c
/* ======================= include files ======================= */ include "mlcv.h"

/* ======================= function name ======================= */ void main (argc, argv)

/* ======================= comments ======================= */
/*
MLC program (for calibration)
 */
/* ======================= declarations ======================= */
/*
type       parameter    i/o      description
---------  ------------ -------  ----------------------------------*/
int        argc;        /* i     argument count                    */
char       **argv;      /* i     program arguments                 */
```

```
/* ========================== log ========================== */
/*
return status description
-------------- ----------------------------------------------
 1          Success
-1          Failure date       comments
--------   ----------------------------------------------
08/10/93   Creation - Jeremy Wong
 */
/* ========================================================= */

{ int status;
mlc_vobjects *vobjects = NULL;

/*
   initialize mlc parameters
*/ status = MLCVinit (&vobjects);
if ( status != 1 ) goto ERROR_EXIT;

status = MLCVapos (vobjects->hndle,
                   vobjects->node_left, vobjects->node_right,
                   vobjects->old_left, vobjects->old_right);
if ( status != 1 ) goto ERROR_EXIT;

/*
   calibrate mlc
*/ status = MLCVcalb (vobjects);
if ( status != 1 ) goto ERROR_EXIT;

free (vobjects);
exit (1);

ERROR_EXIT:
fputs ("Error: MLCVC\n", stderr);
exit (-1);

} mlcvcalb.c
/* ======================== include files ======================== */ include "mlcv.h"
include <time.h>

/* ======================== function name ======================== */ int MLCVcalb (vobjects)

/* ======================== comments ======================== */
/*
Calibrates vanes if necessary
 */
```

```
/* ======================= declarations ======================= */
/*
type       parameter      i/o    description
---------  -------------  ------  -----------------------------------
mlc_vobjects *vobjects;/* i    mlcv parameters                      */

/* ============================= log ========================== */
/*
return status description
-------------- -------------------------------------------------
   1           Success
  -1           Failure date       comments
--------   -----------------------------------------------------
08/10/93   Creation - Jeremy Wong
*/
/* ============================================================ */

{ int status, i, j, *m, n, start, end, map, node;
INT16 ret16;
UINT8 src[17];
clock_t timer, interval;

/*
   send packets to request calibration flag
*/ start = 0;
end = NVANE;
/*
status = MLCVmap (vobjects->hndle, vobjects->node_left,
                  vobjects->node_right, start, end);
if ( status != 1 ) goto ERROR_RETURN;
MLCVwait (1.);
*/
status = MLCVreq (vobjects->hndle, 60, vobjects->node_left,
                  vobjects->node_right, start, end);
if ( status != 1 ) goto ERROR_RETURN;
MLCVwait (1.);

timer = clock ();
interval = 1;
for ( i = 0; i < NVANE; i++ ) {
   for ( j = 0; j < 2; j++ ) {
      if ( j == 0 ) {
         map = i + 1;
         node = vobjects->node_left[i];
      }
      else {
         map = i + 17;
         node = vobjects->node_right[i];
      } status = MLCVstat (vobjects->hndle, 0, 60, map, node, timer,
                         interval);
      if ( status != 1 ) goto ERROR_RETURN;
```

```
        SYSbufinit (src, 0, sizeof (src));
        if ( pGETREG (vobjects->hndle, (UINT8) 0x60, (UINT16) map,
                    (UINT16) 1, (pUINT8) &src[0], &ret16) ) {
            fputs ("Error: MLCVcalb - pGETREG\n", stdout);
            goto ERROR_RETURN;
        } if ( ret16 != 0 ) {
            fputs("Error: MLCVcalb - pGETREG: returned value\n",stdout);
            goto ERROR_RETURN;
        } src[1] = 0;
        printf ("%02X\n", src[0]);
        m = (int *) &src[0];
        n = *m;

if ( n & 16 ) { /* reset leaves to initial position? */
            if ( j == 0 )
                vobjects->pos_left[i] = 0;
            else
                vobjects->pos_right[i] = 0;
        }
        else {
            if ( j == 0 )
                vobjects->pos_left[i] = -32000;
            else
                vobjects->pos_right[i] = -32000;
        }
      }
    }

/*
    reset leaves to initial position/calibrate leaves
*/ status = MLCVleaf (vobjects->hndle,
                   vobjects->node_left, vobjects->node_right,
                   vobjects->leaf_left[0], vobjects->leaf_right[0],
                   vobjects->pos_left, vobjects->pos_right,
                   vobjects->old_left, vobjects->old_right,
                   vobjects->zero_left, vobjects->zero_right,
                   vobjects->oldc_left, vobjects->oldc_right,
                   vobjects->count_left, vobjects->count_right,
                   vobjects->spkt, 0);
if ( status != 1 ) goto ERROR_RETURN;

return (1);

ERROR_RETURN:
fputs ("Error: MLCVcalb\n", stderr);
return (-1);

} mlcvconv.c
/* ====================== include files ====================== */ include "mlcv.h"
```

```
/* ===================== function name ===================== */ int MLCVconv (leaf_left, leaf_right, pos_left, pos_right, zero_left,
              zero_right)

/* ======================= comments ======================= */
/*
Converts leaf positions to actual vane movement positions
*/
/* ====================== declarations ====================== */
/*
type        parameter      i/o     description
--------    -------------  -----   -----------------------------------------*/
double      leaf_left[];   /* i    left leaf positions                      */
double      leaf_right[];  /* i    right leaf positions                     */
long        pos_left[];    /* o    actual vane movement positions           */
long        pos_right[];   /* o    for left and right leaf positions        */
long        zero_left[];   /* i    counts to (0,0)                          */
long        zero_right[];  /* i    for left and right leaf positions        */

/* ========================= log ========================= */
/*
return status  description
-------------  -----------------------------------------------------------
 1             Success
-1             Failure date       comments
--------   -----------------------------------------------------------------
08/10/93   Creation - Jeremy Wong
*/
/* ================================================================== */

{ int i;
long count, max;
double ratio;
double fabs();

/*
   convert leaf positions to actual vane movement positions
*/ ratio = (double) COUNT_PER_MM / (double) 352;

for ( i = 0; i < NVANE; i++ ) {
   if ( i != 14 )
      max = zero_left[i] + zero_right[i];
   else if ( i == 14 )
      max = zero_left[i] + (zero_right[i] * ratio);

count = (long) ((fabs (leaf_left[i]) * (COUNT_PER_MM * 10)) + 0.5);
   if ( leaf_left[i] < 0. )
      pos_left[i] = zero_left[i] - count;
   else if ( leaf_left[i] > 0. )
      pos_left[i] = zero_left[i] + count;
   else
      pos_left[i] = zero_left[i];
   printf ("%d\n", pos_left[i]);
```

```
    if ( pos_left[i] < 0 )
       pos_left[i] = 0;
    else if ( pos_left[i] > max )
       pos_left[i] = max;

if ( i != 14 )
     count = (long) ((fabs (leaf_right[i]) * (COUNT_PER_MM * 10)) + 0.5);
    else if ( i == 14 ) {
       count = (long) ((fabs (leaf_right[i]) * (352 * 10)) + 0.5);
       max = (zero_left[i] / ratio) + zero_right[i];
    }
    if ( leaf_right[i] < 0. )
       pos_right[i] = zero_right[i] + count;
    else if ( leaf_right[i] > 0. )
       pos_right[i] = zero_right[i] - count;
    else
       pos_right[i] = zero_right[i];
    printf ("%d\n", pos_right[i]);
    if ( pos_right[i] < 0 )
       pos_right[i] = 0;
    else if ( pos_right[i] > max )
       pos_right[i] = max;

if ( fabs (leaf_left[i] - leaf_right[i]) < CLOSELEAF ) {
       pos_left[i] += 150;
       if ( i != 14 )
          pos_right[i] += 150;
       else if ( i == 14 )
          pos_right[i] += 0;
    }
 } return (1);

ERROR_RETURN:
 fputs ("Error: MLCVconv\n", stderr);
 return (-1);

} mlcvget.c
/* ======================= include files ======================= */ include "mlcv.h"

/* ======================= function name ======================= */ int MLCVget (hndle, map, node, old)

/* ======================= comments ======================= */
/*
Send packet to request leaf position
 */
/* ======================= declarations ======================= */
/*
type        parameter     i/o      description
---------   -----------   -----    ----------------------------------*/
HANDLE      hndle;        /* i     handle                            */
int         map;          /* i     map number                        */
int         node;         /* i     vane node number                  */
```

```
long      *old;       /* o     old vane movement position          */

/* =========================== log =========================== */
/*
return status  description
--------------  -----------
  1             Success
 -1             Failure date        comments
--------    --------
08/10/93    Creation - Jeremy Wong
*/
/* ========================================================== */

{ int j, *k;
INT16 ret16;
UINT8 src[17];

/*
    send packet to request leaf position
*/

SYSbufinit (src, 0, sizeof (src));
if ( pGETREG (hndle, (UINT8) 0x30, (UINT16) map, (UINT16) 2,
      (pUINT8) &src[0], &ret16) ) {
   fputs ("Error: MLCVget - pGETREG\n", stdout);
   goto ERROR_RETURN;
} if ( ret16 != 0 ) {
   fputs ("Error: MLCVget - pGETREG: returned value\n", stdout);
   goto ERROR_RETURN;
} for ( j = 0; j < 2; j++ )
   printf ("%02X", src[j]);
printf ("\n");

src[2] = src[0];
src[0] = src[1];
src[1] = src[2];
k = (int *) &src[0];
j = *k;
if ( j < 0 )  /* what if position is -ve? */
   j = 0;

*old = j;
printf ("%d\n", j);

return (1);

ERROR_RETURN:
fputs ("Error: MLCVget\n", stderr);
return (-1);

}
```

```
mlcvinit.c
/* ======================= include files ======================= */ include "mlcv.h"

/* ======================= function name ======================= */ int MLCVinit (vobjects)

/* ========================== comments ========================= */
/*
Initialize mlcv parameters
 */
/* ========================= declarations ====================== */
/*
type        parameter      i/o      description
---------   -------------  -------  ---------------------------------------*/
mlc_vobjects **vobjects;/*  o      mlcv parameters                         */

/* =========================== log ============================= */
/*
return status description
--------------- --------------------------------------------------------
 1          Success
-1          Failure date     comments
-------- --------------------------------------------------------
08/10/93 Creation - Jeremy Wong
 */
/* ============================================================= */

{ int status, i, j, max, num, start, end;
long i1, i2;
INT16 ret16;
UINT8 map, port_intr;
mlc_vobjects *vobj = NULL;
char filename[180], str[180];
FILE *fp = NULL, *fopen();

vobj = (mlc_vobjects *) malloc (sizeof (mlc_vobjects));

/*
   initialize mlc parameters
*/ vobj->ngantry = 0;
for ( i = 0; i < NVANE; i++ ) {
   vobj->node_left[i] = 0;
   vobj->pos_left[i] = 0;
   vobj->old_left[i] = 0;
   vobj->zero_left[i] = 0;
   vobj->oldc_left[i] = 0;
   vobj->open_left[i] = 0;
   vobj->close_left[i] = 0;
   vobj->count_left[i] = 0.;

vobj->node_right[i] = 0;
```

```
      vobj->pos_right[i] = 0;
      vobj->old_right[i] = 0;
      vobj->zero_right[i] = 0;
      vobj->oldc_right[i] = 0;
      vobj->open_right[i] = 0;
      vobj->close_right[i] = 0;
      vobj->count_right[i] = 0.;
   } for ( i = 0; i < NGANTRY; i++ ) {
      for ( j = 0; j < NVANE; j++ ) {
         vobj->leaf_left[i][j] = 0.;
         vobj->leaf_right[i][j] = 0.;
      }
   }

SYSbufinit (vobj->spkt, 0, sizeof (vobj->spkt));
   strcpy (vobj->spkt, ":02dd5A160000dddd00");

SYSbufinit (vobj->leaf_file, 0, sizeof (vobj->leaf_file));

/*
      assign vane node numbers
   */

MLCVnode (vobj->node_left, vobj->node_right);

/*
      open port
   */ map = 0;
   port_intr = 0X66;
   if ( pOPEN (port_intr, &vobj->hndle) ) {
      fputs ("Error: MLCVinit - pOPEN\n", stderr);
      goto ERROR_RETURN;
   }

/*
      set scale x/8 and checksum
   */ if ( pSENDPKT(vobj->hndle, (pUINT8) ":01005A6200000300", &ret16) ) {
      fputs ("Error: MLCVinit - pSENDPKT\n", stderr);
      goto ERROR_RETURN;
   } if ( ret16 != 0 ) {
      fputs ("Error: MLCVinit - pSENDPKT: returned value\n", stderr);
      goto ERROR_RETURN;
   }
   MLCVwait (1.);
   /*
   if ( pSENDPKT(vobj->hndle, (pUINT8) ":01005AF600000400", &ret16) ) {
      fputs ("Error: MLCVinit - pSENDPKT\n", stderr);
      goto ERROR_RETURN;
   } if ( ret16 != 0 ) {
      fputs ("Error: MLCVinit - pSENDPKT: returned value\n", stderr);
```

```c
        goto ERROR_RETURN;
    }
    MLCVwait (1.);
*/
/* x/4 and Rotate CCW for 74 */
    if ( pSENDPKT(vobj->hndle, (pUINT8) ":014A5A6200000000200", &ret16) ) {
        fputs ("Error: MLCVinit - pSENDPKT\n", stderr);
        goto ERROR_RETURN;
    } if ( ret16 != 0 ) {
        fputs ("Error: MLCVinit - pSENDPKT: returned value\n", stderr);
        goto ERROR_RETURN;
    }
    MLCVwait (1.);

if ( pSENDPKT(vobj->hndle, (pUINT8) ":014A5A6200900800", &ret16) ) {
        fputs ("Error: MLCVinit - pSENDPKT\n", stderr);
        goto ERROR_RETURN;
    } if ( ret16 != 0 ) {
        fputs ("Error: MLCVinit - pSENDPKT: returned value\n", stderr);
        goto ERROR_RETURN;
    }
    MLCVwait (1.);

/*
    open data file with counts to (0,0) for left and right leaf positions
*/

SYSbufinit (filename, 0, sizeof (filename));
    strcat (filename, "mlc.dat");
    fp = fopen (filename, "r");
    if ( fp == NULL ) goto ERROR_RETURN;

/*
    read data file
*/ max = 160;
    fgets (str, max, fp); /* comments */
    fgets (str, max, fp); /* comments */ for ( i = 0; i < NVANE; i++ ) {
        SYSbufinit (str, 0, sizeof (str));
        fgets (str, max, fp);
        sscanf (str, "%d %ld %ld", &num, &i1, &i2);
        vobj->zero_left[i] = i1;
        vobj->zero_right[i] = i2;
    }

/*
    close data file
*/ fclose (fp);

/*
    open data file with potentiometer counts for left and right leaf
```

```
      positions
*/

SYSbufinit (filename, 0, sizeof (filename));
strcat (filename, "mlcpoten.dat");
fp = fopen (filename, "r");
if ( fp == NULL ) goto ERROR_RETURN;

/*
   read data file
*/ max = 160;
fgets (str, max, fp); /* comments */
fgets (str, max, fp); /* comments */ for ( i = 0; i < NVANE; i++ ) {
   SYSbufinit (str, 0, sizeof (str));
   fgets (str, max, fp);
   sscanf (str, "%d %ld %ld", &num, &i1, &i2);
   vobj->open_left[i] = i1;
   vobj->close_left[i] = i2;
   vobj->count_left[i] = (double) ((vobj->close_left[i] -
                                    vobj->open_left[i]) + 1) /
                        (double) 4.6;
   vobj->oldc_left[i] = vobj->open_left[i];
} for ( i = 0; i < NVANE; i++ ) {
   SYSbufinit (str, 0, sizeof (str));
   fgets (str, max, fp);
   sscanf (str, "%d %ld %ld", &num, &i1, &i2);
   vobj->open_right[i] = i1;
   vobj->close_right[i] = i2;
   vobj->count_right[i] = (double) ((vobj->close_right[i] -
                                     vobj->open_right[i]) + 1) /
                        (double) 4.6;
   vobj->oldc_right[i] = vobj->open_right[i];
}

/*
   close data file
*/ fclose (fp);

/*
   monitor maps of nodes
*/ start = 0;
end = NVANE;
status = MLCVmap (vobj->hndle, vobj->node_left, vobj->node_right, start,
                  end);
if ( status != 1 ) goto ERROR_RETURN;
MLCVwait (1.);

*vobjects = vobj;
return (1);
```

```
ERROR_RETURN:
fputs ("Error: MLCVinit\n", stderr);
return (-1);

} mlcvinpt.c
/* ======================= include files ======================= */ include "mlcv.h"

/* ======================= function name ======================= */ int MLCVinpt (filename, ngantry, leaf_left, leaf_right)

/* ======================= comments ======================= */
/*
Reads input file of leaf positions
 */
/* ======================= declarations ======================= */
/*
type       parameter   i/o      description
---------  ----------  -------  -----------------------------------------*/
char       *filename;  /* i     filename                                 */
int        *ngantry;   /* o     number of gantry angles read             */
double leaf_left[][NVANE]; /*o   left leaf positions                     */
double leaf_right[][NVANE];/*o   right leaf positions                    */

/* ======================= log ======================= */
/*
return status description
-------------- -------------
 1             Success
-1             Failure date       comments
---------  -------------
08/10/93   Creation - Jeremy Wong
 */
/* ============================================================ */

{

FILE *fp = NULL, *fopen();
int i, j, max, num;
double f;
char str[180];

/*
   open input file
*/ fp = fopen (filename, "r");
if ( fp == NULL ) goto ERROR_RETURN;
/*
   read file
*/ max = 160;
```

```
fgets (str, max, fp); /* File Rev */
fgets (str, max, fp); /* Last Name */
fgets (str, max, fp); /* First Name */
fgets (str, max, fp); /* Patient ID */

SYSbufinit (str, 0, sizeof (str));
fgets (str, max, fp); /* Number of Fields */
sscanf (str, "Number of Fields = %d", &num);
*ngantry = num;

for ( i = 0; i < *ngantry; i++ ) {
    fgets (str, max, fp); /*   */
    fgets (str, max, fp); /* Field */
    fgets (str, max, fp); /* Treatment Count */
    fgets (str, max, fp); /* Operator */
    fgets (str, max, fp); /* Collimator */
    fgets (str, max, fp); /* Gantry */ for ( j = 0; j < NVANE; j++ ) {
        SYSbufinit (str, 0, sizeof (str));
        fgets (str, max, fp);
        sscanf (str, "Leaf %dA = %lf", &num, &f);
        leaf_left[i][j] = f;
    } for ( j = 0; j < NVANE; j++ ) {
        SYSbufinit (str, 0, sizeof (str));
        fgets (str, max, fp);
        sscanf (str, "Leaf %dB = %lf", &num, &f);
        leaf_right[i][j] = f;
    }
    fgets (str, max, fp); /* Note */
    fgets (str, max, fp); /* Shape */
    fgets (str, max, fp); /* Magnification */
}

/*
   close input file
*/ fclose (fp);

/*
  check leaf positions
*/ for ( i = 0; i < *ngantry; i++ ) {
    for ( j = 0; j < NVANE; j++ ) {
        if ( leaf_left[i][j] > leaf_right[i][j] ) {
            fputs ("Error: MLCVinpt - input data error\n", stderr);
            goto ERROR_RETURN;
        }
    }
} return (1);

ERROR_RETURN:
fputs ("Error: MLCVinpt\n", stderr);
return (-1);
```

}
mlcvintl.c
/* ========================= include files ========================= */ include "mlcv.h"
include <time.h>

/* ========================= function name ========================= */ clock_t MLCVintl (new_pos, old_pos)

/* ========================= comments ========================= */
/*
Calculates interval of time to wait for specified amount vane movement
 */
/* ========================= declarations ========================= */
/*
type      parameter      i/o      description
---------  -------------  -------  ----------------------------------------*/
long      new_pos;       /* i      new vane movement position              */
long      old_pos;       /* i      old vane movement position              */

/* ========================= log ========================= */
/*
return status description
--------------  ------------------------------------------------------
 intl           interval of time to wait date      comments
--------  ------------------------------------------------------
02/23/95  Creation - Jeremy Wong
 */
/* ========================================================== */

{ long count;
clock_t intl;
double ceil();

count = (long) abs (new_pos - old_pos);

if ( count <= 1000 ) {
    intl = 5;
}
else if ( count > 1000 ) {
    intl = (clock_t) ceil ((double) count / (double) COUNT_PER_SEC);
} if ( new_pos < 0 )
    intl = 30;
if ( intl > 30 ) {
    intl = 30;
} return intl;

ERROR_RETURN:

```
        fputs ("Error: MLCVintl\n", stderr);
        return 30;

} mlcvleaf.c
/* ======================= include files ======================= */ include "mlcv.h"
include <time.h>

/* ======================= function name ======================= */ int MLCVleaf (hndle, node_left, node_right, leaf_left, leaf_right,
              pos_left, pos_right, old_left, old_right, zero_left,
              zero_right, oldc_left, oldc_right, count_left,
              count_right, spkt, code)

/* =========================== comments =========================== */
/*
Sends packets to move leaves
 */
/* ========================= declarations ========================= */
/*
type      parameter       i/o     description
--------- --------------- ------- ------------------------------------*/
HANDLE    hndle;          /* i    handle                              */
int       node_left[];    /* i    vane node numbers                   */
int       node_right[];   /* i    for left and right leaves           */
double    leaf_left[];    /* i    leaf positions for                  */
double    leaf_right[];   /* i    left and right leaves               */
long      pos_left[];     /* i    new vane movement positions         */
long      pos_right[];    /* i    for left and right leaf positions   */
long      old_left[];     /* i    old vane movement positions         */
long      old_right[];    /* i    for left and right leaf positions   */
long      zero_left[];    /* i    counts to (0,0)                     */
long      zero_right[];   /* i    for left and right leaf positions   */
long      oldc_left[];    /* i    previous potentiometer counts       */
long      oldc_right[];   /* i    for left and right leaf positions   */
double    count_left[];   /* i    potentiometer counts                */
double    count_right[];  /*i     for left and right leaf positions   */
UINT8     *spkt;          /* i    sample packet                       */
int       code;           /* i    0: move leaves to leaf positions    */
                          /* i    1: move leaves to vane positions    */

/* ============================ log ============================ */
/*
return status description
-------------- -----------------------------------------------------
 1             Success
-1             Failure date      comments
--------  -----------------------------------------------------
08/10/93  Creation - Jeremy Wong
 */
/* ============================================================== */

{
```

```
int status, i, j, start, end, flag[30];
long pos;
INT16 ret16;
clock_t timer, interval, MLCVintl();
double ceil();

/*
   send packets to move leaves
*/ if ( code == 1 ) {
   status = MLCVconv (leaf_left, leaf_right, pos_left, pos_right,
                      zero_left, zero_right);
   if ( status != 1 ) goto ERROR_RETURN;
} start = 0;
end = NVANE;
/*
status = MLCVmap (hndle, node_left, node_right, start, end);
if ( status != 1 ) goto ERROR_RETURN;
MLCVwait (1.);
*/
for ( j = 0; j < 2; j++ ) {
   if ( pSENDPKT(hndle, (pUINT8) ":01005AF000000000", &ret16) ) {
      fputs ("ERROR: MLCVleaf - pSENDPKT\n", stderr);
      goto ERROR_RETURN;
   } if ( ret16 != 0 ) {
      fputs ("ERROR: MLCVleaf - pSENDPKT\n", stderr);
      goto ERROR_RETURN;
   }
   /*MLCVwait (1.);*/ status = MLCVmove (hndle, node_left, node_right, pos_left, pos_right,
                      old_left, old_right, zero_left, zero_right, spkt,
                      start, end, flag, j);
   if ( status != 1 ) goto ERROR_RETURN;
   /*MLCVwait (1.);*/
   if ( pSENDPKT(hndle, (pUINT8) ":01005AF000000300", &ret16) ) {
      fputs ("ERROR: MLCVleaf - pSENDPKT\n", stderr);
      goto ERROR_RETURN;
   } if ( ret16 != 0 ) {
      fputs ("ERROR: MLCVleaf - pSENDPKT\n", stderr);
      goto ERROR_RETURN;
   }
   /*MLCVwait (1.);*/
   printf ("LEAF: %d\n", j);

timer = clock ();
   for ( i = 0; i < NVANE; i++ ) {
      if ( flag[i] ) {
         interval = (clock_t) MLCVintl (pos_left[i], old_left[i]);
         status = MLCVstat (hndle, 1, 60, i+1, node_left[i], timer,
                            interval);

status = MLCVget (hndle, i+1, node_left[i], &old_left[i]);
```

```
            if ( status != 1 ) goto ERROR_RETURN;

pos = pos_left[i];
         if ( pos < 0 )
            pos = 0;
         if ( abs (pos - old_left[i]) > TOL ) {
            status = MLCVrsnd (hndle, i+1, node_left[i], pos_left[i],
                              &old_left[i], &oldc_left[i],
                              count_left[i], spkt);
            if ( status != 1 ) {
               fputs ("Error: MLCVleaf - wrong position\n", stdout);
               goto ERROR_RETURN;
            }
         }
         else {
            status = MLCVpotn (hndle, i+1, node_left[i], old_left[i],
                              &oldc_left[i], count_left[i]);
            if ( status != 1 ) {
               fputs ("Error: MLCVleaf - wrong position\n", stdout);
               goto ERROR_RETURN;
            }
         }
      } if ( flag[i+15] ) {
         interval = (clock_t) MLCVintl (pos_right[i], old_right[i]);
         status = MLCVstat (hndle, 1, 60, i+17, node_right[i], timer,
                           interval);

status = MLCVget (hndle, i+17, node_right[i], &old_right[i]);
         if ( status != 1 ) goto ERROR_RETURN;

pos = pos_right[i];
         if ( pos < 0 )
            pos = 0;
         if ( abs (pos - old_right[i]) > TOL ) {
            status = MLCVrsnd (hndle, i+17, node_right[i], pos_right[i],
                              &old_right[i], &oldc_right[i],
                              count_right[i], spkt);
            if ( status != 1 ) {
               fputs ("Error: MLCVleaf - wrong position\n", stdout);
               goto ERROR_RETURN;
            }
         }
         else {
            status = MLCVpotn (hndle, i+17, node_right[i], old_right[i],
                              &oldc_right[i], count_right[i]);
            if ( status != 1 ) {
               fputs ("Error: MLCVleaf - wrong position\n", stdout);
               goto ERROR_RETURN;
            }
         }
      }
   }
} return (1);

ERROR_RETURN:
fputs ("Error: MLCVleaf\n", stderr);
```

```
return (-1);
} mlcvmap.c
/* ======================= include files ======================= */ include "mlcv.h"

/* ======================= function name ======================= */ int MLCVmap (hndle, node_left, node_right, start, end)

/* ======================= comments ======================= */
/*
Monitors maps of specified vane nodes
*/
/* ======================= declarations ======================= */
/*
type      parameter    i/o     description
--------- ------------ ------- ------------------------------------*/
HANDLE    hndle;       /* i    handle                              */
int       node_left[]; /* i    vane node numbers                   */
int       node_right[];/* i    for left and right leaves           */
int       start;       /* i    starting node number to request     */
int       end;         /* i    ending node number to request       */

/* ============================ log ============================ */
/*
return status description
------------- ------------------------------------------------------
 1            Success
-1            Failure date       comments
--------   ------------------------------------------------------
08/10/93   Creation - Jeremy Wong
*/
/* ============================================================ */

{ int i, j, map, map1, map2;
INT16 ret16;
UINT8 node;
UINT8 src[17];

/*
   monitor maps of specified of vane nodes
*/ map1 = 0;
map2 = 0;
for ( i = start; i < end; i++ ) {
   for ( j = 0; j < 2; j++ ) {
      if ( j == 0 ) {
         node = (UINT8) node_left[i];
         map1++;
         map = map1;
      }
```

```
        else {
            node = (UINT8) node_right[i];
            map2++;
            map = map2;
        } if ( j == 0 ) {
            if ( pPUTREG (hndle, (UINT8) 0xC0+map-1, (UINT16) 0, (UINT16)1,
                        (pUINT8) &node, &ret16) ) {
                fputs ("Error: MLCVmap - pPUTREG\n", stdout);
                goto ERROR_RETURN;
            }
        }
        else {
            if ( pPUTREG (hndle, (UINT8) 0xD0+map-1, (UINT16) 0, (UINT16)1,
                        (pUINT8) &node, &ret16) ) {
                fputs ("Error: MLCVmap - pPUTREG\n", stdout);
                goto ERROR_RETURN;
            }
        } if ( ret16 != 0 ) {
            fputs ("Error: MLCVmap - pPUTREG: returned value\n", stdout);
            goto ERROR_RETURN;
        }
    }
}

/*
    reset register change flags of maps
*/ map1 = 0;
map2 = 16;
for ( i = start; i < end; i++ ) {
    for ( j = 0; j < 2; j++ ) {
        if ( j == 0 ) {
            map1++;
            map = map1;
        }
        else {
            map2++;
            map = map2;
        } if ( pREGSTAT (hndle, (UINT16) map, &ret16) ) {
            fputs ("Error: MLCVmap - pREGSTAT\n", stdout);
            goto ERROR_RETURN;
        }
    }
} if ( pGETREG (hndle, (UINT8) 0xC0, (UINT16) 0, (UINT16) 16,
            (pUINT8) &src[0], &ret16) )
    fputs ("Error: MLCVmap - pGETREG\n", stdout);

if ( ret16 != 0 )
    fputs ("Error: MLCVmap - pGETREG: returned value\n", stdout);

for ( i = 0; i < 16; i++ )
```

```
   printf ("%02X", src[i]);
printf ("\n");

if ( pGETREG (hndle, (UINT8) 0xD0, (UINT16) 0, (UINT16) 16,
          (pUINT8) &src[0], &ret16) )
   fputs ("Error: MLCVmap - pGETREG\n", stdout);

if ( ret16 != 0 )
   fputs ("Error: MLCVmap - pGETREG: returned value\n", stdout);

for ( i = 0; i < 16; i++ )
   printf ("%02X", src[i]);
printf ("\n");

return (1);

ERROR_RETURN:
fputs ("Error: MLCVmap\n", stderr);
return (-1);

} mlcvmove.c
/* ========================= include files ========================= */ include "mlcv.h"

/* ========================= function name ========================= */ int MLCVmove (hndle, node_left, node_right, pos_left, pos_right,
          old_left, old_right, zero_left, zero_right,
          spkt, start, end, flag, code)

/* ========================= comments ========================= */
/*
Sends packets to move leaves
*/
/* ========================= declarations ========================= */
/*
type      parameter      i/o      description
---------  -------------  -------  ----------------------------------*/
HANDLE    hndle;         /* i      handle                            */
int       node_left[];   /* i      vane node numbers                 */
int       node_right[];  /* i      for left and right leaves         */
long      pos_left[];    /* i      new vane movement positions       */
long      pos_right[];   /* i      for left and right leaf positions */
long      old_left[];    /* i      old vane movement positions       */
long      old_right[];   /* i      for left and right leaf positions */
long      zero_left[];   /* i      counts to (0,0)                   */
long      zero_right[];  /* i      for left and right leaf positions */
UINT8     *spkt;         /* i      sample packet                     */
int       start;         /* i      starting node number to move      */
int       end;           /* i      ending node number to move        */
int       *flag;         /* i      whether leaf finished moving      */
int       code;          /* i      0: move opposing leaves           */
                         /* i      1: move rest of leaves            */

/* ========================= log ========================= */
/*
return status description
```

```
              -------------------------------------------------
1             Success
-1            Failure date      comments
--------  -------------------------------------------------
08/10/93  Creation - Jeremy Wong
*/
/* ============================================================ */

{ int status, i;
long max_l, max_r;
double ratio;

/*
    send packets to move leaves
*/ ratio = (double) COUNT_PER_MM / (double) 352;

for ( i = 0; i < 30; i++ )
   flag[i] = 0;

for ( i = start; i < end; i++ ) {
   if ( i != 14 ) {
      max_l = (zero_left[i] + zero_right[i]) - old_right[i];
      max_r = (zero_left[i] + zero_right[i]) - old_left[i];
   }
   else if ( i == 14 ) {
      max_l = (zero_left[i] + (zero_right[i] * ratio)) -
              (old_right[i] * ratio);
      max_r = ((zero_left[i] / ratio) + zero_right[i]) -
              (old_left[i] / ratio);
   } if ( code == 0 ) {
      if ( pos_left[i] > max_l ) {
         if ( pos_right[i] != old_right[i] ) {
            if ( abs (pos_right[i] - old_right[i]) > TOL ) {
               status = MLCVsend (hndle, node_right[i], pos_right[i],
                                  spkt);
               if ( status != 1 ) goto ERROR_RETURN;
               flag[i+15] = 1;
            }
         }
      }
      else if ( pos_right[i] > max_r ) {
         if ( pos_left[i] != old_left[i] ) {
            if ( abs (pos_left[i] - old_left[i]) > TOL ) {
               status = MLCVsend (hndle, node_left[i], pos_left[i],
                                  spkt);
               if ( status != 1 ) goto ERROR_RETURN;
               flag[i] = 1;
            }
         }
      }
   }
   else if ( code == 1 ) {
```

```
        if ( pos_left[i] != old_left[i] ) {
            if ( abs (pos_left[i] - old_left[i]) > TOL ) {
                status = MLCVsend (hndle, node_left[i], pos_left[i], spkt);
                if ( status != 1 ) goto ERROR_RETURN;
                flag[i] = 1;
            }
        } if ( pos_right[i] != old_right[i] ) {
            if ( abs (pos_right[i] - old_right[i]) > TOL ) {
                status = MLCVsend (hndle, node_right[i], pos_right[i],spkt);
                if ( status != 1 ) goto ERROR_RETURN;
                flag[i+15] = 1;
            }
        }
      }
   }
} return (1);

ERROR_RETURN:
fputs ("Error: MLCVmove\n", stderr);
return (-1);

} mlcvnode.c
/* ======================= include files ======================= */ include "mlcv.h"

/* ======================= function name ======================= */ int MLCVnode (node_left, node_right)

/* ======================= comments ======================= */
/*
Assigns vane node numbers
 */
/* ======================= declarations ======================= */
/*
type       parameter    i/o      description
---------  ------------ -------- ------------------------------------------
int        node_left[]; /* o     vane node numbers                         */
int        node_right[];/* o     for left and right leaves                 */

/* ======================= log ======================= */
/*
return status description
--------------- ----------------------------------------------------------
 1              Success
-1              Failure date       comments
--------   ----------------------------------------------------------------
08/10/93   Creation - Jeremy Wong
 */
/* ================================================================ */

{
```

```
   int i, left, right;

/*
      assign vane node numbers
   */ left = 30;
   for ( i = 0; i < NVANE; i++ ) {
      node_left[i] = left;
      left++;
   } right = 60;
   for ( i = 0; i < NVANE; i++ ) {
      node_right[i] = right;
      right++;
   } return (1);

ERROR_RETURN:
fputs ("Error: MLCVnode\n", stderr);
return (-1);

} mlcvopen.c
/* ======================= include files ======================= */ include "mlcv.h"

/* ======================= function name ======================= */ int MLCVopen (hndle, node_left, node_right, leaf_left, leaf_right,
              pos_left, pos_right, old_left, old_right, zero_left,
              zero_right, oldc_left, oldc_right, count_left,
              count_right, spkt)

/* ======================= comments ======================= */
/*
Sends packets to move leaves to open position
*/
/* ======================= declarations ======================= */
/*
type       parameter       i/o      description
---------  -------------   -------  -------------------------------------*/
HANDLE     hndle;          /* i     handle                               */
int        node_left[];    /* i     vane node numbers                    */
int        node_right[];   /* i     for left and right leaves            */
double     leaf_left[];    /* i     leaf positions for                   */
double     leaf_right[];   /* i     left and right leaves                */
long       pos_left[];     /* i     new vane movement positions          */
long       pos_right[];    /* i     for left and right leaf positions    */
long       old_left[];     /* i     old vane movement positions          */
long       old_right[];    /* i     for left and right leaf positions    */
long       zero_left[];    /* i     counts to (0,0)                      */
long       zero_right[];   /* i     for left and right leaf positions    */
long       oldc_left[];    /* i     previous potentiometer counts        */
```

```
long      oldc_right[];/* i   for left and right leaf positions   */
double    count_left[];/* i   potentiometer counts                */
double    count_right[];/*i   for left and right leaf positions   */
UINT8     *spkt;       /* i   sample packet                       */

/* ============================== log ============================ */
/*
return status description
--------------- -------------------------------------------------
  1           Success
 -1           Failure date        comments
--------    -------------------------------------------------
08/10/93    Creation - Jeremy Wong
 */
/* =============================================================== */

{ int status, i;

/*
   send packets to move leaves to open position
*/ for ( i = 0; i < NVANE; i++ ) {
   pos_left[i] = 0;
   pos_right[i] = 0;
} status = MLCVleaf (hndle, node_left, node_right, leaf_left, leaf_right,
                   pos_left, pos_right, old_left, old_right, zero_left,
                   zero_right, oldc_left, oldc_right, count_left,
                   count_right, spkt, 0);
if ( status != 1 ) goto ERROR_RETURN;

return (1);

ERROR_RETURN:
fputs ("Error: MLCVopen\n", stderr);
return (-1);

} mlcvpkt.c
/* ========================= include files ======================== */ include "mlcv.h"

/* ========================= function name ======================== */ int MLCVpkt (node, pos, spkt, pkt)

/* ========================== comments ============================ */
/*
Creates packet to send
 */
/* ========================= declarations ========================= */
/*
```

```
type        parameter    i/o     description
---------   ------------ ------- ----------------------------------------*/
int         node;        /* i    destination node of package            */
long        pos;         /* i    vane movement position                 */
UINT8       *spkt;       /* i    sample packet                          */
UINT8       *pkt;        /* o    packet                                 */

/* =========================== log =========================== */
/*
return status description
-------------- --------------------------------------------------------
   1           Success
  -1           Failure date       comments
--------   --------------------------------------------------------
08/10/93   Creation - Jeremy Wong
 */
/* ================================================================ */

{ char str[8];

/*
    create packet to send
*/

SYSbufinit (pkt, 0, sizeof (pkt));
strcpy (pkt, spkt);

SYSbufinit (str, 0, sizeof (str));
sprintf (str, "%02X", node);
pkt[3] = str[0];
pkt[4] = str[1];

SYSbufinit (str, 0, sizeof (str));
sprintf (str, "%04X", pos);
pkt[13] = str[0];
pkt[14] = str[1];
pkt[15] = str[2];
pkt[16] = str[3];

return (1);

ERROR_RETURN:
fputs ("Error: MLCVpkt\n", stderr);
return (-1);

} mlcvpotn.c
/* ======================= include files ======================= */ include "mlcv.h"

/* ======================= function name ======================= */ int MLCVpotn (hndle, map, node, old, oldc, count)
```

```
/* ========================= comments ========================= */
/*
Reads potentiometer counts, and check for tolerance between encoder
and potentiometer
 */
/* ========================= declarations ========================= */
/*
type      parameter    i/o      description
--------- ------------ -------- ----------------------------------------*/
HANDLE    hndle;       /* i     handle                                 */
int       map;         /* i     map number                             */
int       node;        /* i     vane node number                       */
long      old;         /* i     old vane movement position             */
long      *oldc;       /* i     old potentiometer count                */
double    count;       /* i     potentiometer count                    */

/* ========================= log ========================= */
/*
return status description
-------------- -----------------------------------------------------------
 1             Success
-1             Failure date      comments
--------  -----------------------------------------------------------
02/09/95  Creation - Jeremy Wong
 */
/* ================================================================= */

{ int status, *i, pos;
double dist, dist1;
char str[8];
INT16 ret16;
UINT8 src[17], pkt[20];
double fabs();
clock_t timer, interval;

/*
   get amount of absolute leaf movement from encoder
*/ dist = (double) old / (double) (COUNT_PER_MM * 10);

/*
   send packet to request potentiometer count
*/

SYSbufinit (pkt, 0, sizeof (pkt));
strcpy (pkt, ":00dd5A50008000");
SYSbufinit (str, 0, sizeof (str));
sprintf (str, "%02X", node);
pkt[3] = str[0];
pkt[4] = str[1];
if ( pSENDPKT (hndle, (pUINT8) pkt, &ret16) ) {
   fputs ("Error: MLCVpotn - pSENDPKT\n", stdout);
   goto ERROR_RETURN;
}
```

```
if ( ret16 != 0 ) {
    fputs ("Error: MLCVpotn - pSENDPKT: returned value\n", stdout);
    goto ERROR_RETURN;
} timer = clock ();
interval = 1;
status = MLCVstat (hndle, 0, 50, map, node, timer, interval);
if ( status != 1 ) goto ERROR_RETURN;

SYSbufinit (src, 0, sizeof (src));
if ( pGETREG (hndle, (UINT8) 0x51, (UINT16) map, (UINT16) 1,
      (pUINT8) &src[0], &ret16) ) {
    fputs ("Error: MLCVpotn - pGETREG\n", stdout);
    goto ERROR_RETURN;
} if ( ret16 != 0 ) {
    fputs ("Error: MLCVpotn - pGETREG: returned value\n", stdout);
    goto ERROR_RETURN;
} src[1] = 0;
i = (int *) &src[0];
pos = *i;

/*
   get amount of absolute leaf movement from potentiometer
*/ dist1 = (double) pos / (double) count;
*oldc = pos;

/*
   check encoder and potentiometer distances within 0.5 mm tolerance
*/ printf ("%d %lf %lf\n", pos, dist1, dist);
if ( fabs (dist - dist1) > 0.005 ) {
    fputs ("ERROR: MLCVpotn - wrong position\n", stderr);
    goto ERROR_RETURN;
} return (1);

ERROR_RETURN:
fputs ("Error: MLCVpotn\n", stderr);
return (-1);

} mlcvreq.c
/* ======================= include files ======================= */ include "mlcv.h"

/* ======================= function name ======================= */ int MLCVreq (hndle, reg, node_left, node_right, start, end)
```

```
/* ======================== comments ======================== */
/*
Sends packets to request registers of vane nodes
*/
/* ======================== declarations ==================== */
/*
type       parameter     i/o      description
---------- ------------  -------- ---------------------------------------*/
HANDLE     hndle;        /* i     handle                                 */
int        reg;          /* i     register requested                     */
int        node_left[];  /* i     vane node numbers                      */
int        node_right[]; /* i     for left and right leaves              */
int        start;        /* i     starting node number to request        */
int        end;          /* i     ending node number to request          */

/* =========================== log ========================== */
/*
return status description
--------------- -----------------------------------------------------
 1              Success
-1              Failure date      comments
--------  -----------------------------------------------------------
08/10/93  Creation - Jeremy Wong
*/
/* ========================================================== */

{ int i, j, node;
INT16 ret16;
UINT8 pkt[20];
char str[8];

/*
   send packets to request registers of vane nodes
*/

SYSbufinit (pkt, 0, sizeof (pkt));
if ( reg == 30 )
   strcpy (pkt, ":00dd5A30008000");
else if ( reg == 60 )
   strcpy (pkt, ":00dd5A60008000");

for ( i = start; i < end; i++ ) {
   for ( j = 0; j < 2; j++ ) {
      if ( j == 0 )
         node = node_left[i];
      else
         node = node_right[i];

SYSbufinit (str, 0, sizeof (str));
      sprintf (str, "%02X", node);
      pkt[3] = str[0];
      pkt[4] = str[1];
      printf ("%s\n", pkt);
      if ( pSENDPKT (hndle, (pUINT8) pkt, &ret16) ) {
         fputs ("Error: MLCVreq - pSENDPKT\n", stdout);
         goto ERROR_RETURN;
```

```
        } if ( ret16 != 0 ) {
            fputs ("Error: MLCVreq - pSENDPKT: returned value\n", stdout);
            goto ERROR_RETURN;
        }
        MLCVwait (1.);
    }
} return (1);

ERROR_RETURN:
fputs ("Error: MLCVreq\n", stderr);
return (-1);

} mlcvrsnd.c
/* ======================= include files ======================= */ include "mlcv.h"
include <time.h>

/* ======================= function name ======================= */ int MLCVrsnd (hndle, map, node, pos, old, oldc, count, spkt)

/* ======================= comments ======================= */
/*
Resends packet to move leaf
 */
/* ======================= declarations ======================= */
/*
type       parameter    i/o     description
---------  -----------  ------  ------------------------------------------*/
HANDLE     hndle;       /* i    handle                                  */
int        map;         /* i    map number                              */
int        node;        /* i    vane node number                        */
long       pos;         /* i    new vane movement position              */
long       *old;        /* i    old vane movement position              */
long       *oldc;       /* i    previous potentiometer count            */
double     count;       /* i    potentiometer count                     */
UINT8      *spkt;       /* i    sample packet                           */

/* ======================= log ======================= */
/*
return status description
------------- -----------------------------------------------------------
 1            Success
-1            Failure date       comments
--------   -----------------------------------------------------------
08/10/93   Creation - Jeremy Wong
 */
/* ============================================================= */

{
```

```
    int status;
    INT16 ret16;
    clock_t timer, interval, MLCVintl();
    double ceil();

/*
        resend packet to move leaf
    */
    /*
    if ( pSENDPKT(hndle, (pUINT8) ":01005AF000000000", &ret16) ) {
        fputs ("ERROR: MLCVrsnd - pSENDPKT\n", stderr);
        goto ERROR_RETURN;
    } if ( ret16 != 0 ) {
        fputs ("ERROR: MLCVrsnd - pSENDPKT\n", stderr);
        goto ERROR_RETURN;
    }
    */
    status = MLCVsend (hndle, node, pos, spkt);
    if ( status != 1 ) goto ERROR_RETURN;
    /*
    if ( pSENDPKT(hndle, (pUINT8) ":01005AF000000300", &ret16) ) {
        fputs ("ERROR: MLCVrsnd - pSENDPKT\n", stderr);
        goto ERROR_RETURN;
    } if ( ret16 != 0 ) {
        fputs ("ERROR: MLCVrsnd - pSENDPKT\n", stderr);
        goto ERROR_RETURN;
    }
    */
    timer = clock ();
    interval = (clock_t) MLCVintl (pos, *old);
    status = MLCVstat (hndle, 1, 60, map, node, timer, interval);

status = MLCVget (hndle, map, node, old);
    if ( status != 1 ) goto ERROR_RETURN;

if ( pos < 0 )
        pos = 0;
    if ( abs (pos - *old) > TOL ) {
        fputs ("Error: MLCVrsnd - wrong position\n", stdout);
        goto ERROR_RETURN;
    }
    else {
        status = MLCVpotn (hndle, map, node, *old, oldc, count);
        if ( status != 1 ) {
            fputs ("Error: MLCVrsnd - wrong position\n", stdout);
            goto ERROR_RETURN;
        }
    } return (1);

ERROR_RETURN:
    fputs ("Error: MLCVrsnd\n", stderr);
    return (-1);

}
```

```
mlcvsend.c
/* ======================= include files ======================= */ include "mlcv.h"

/* ======================= function name ======================= */ int MLCVsend (hndle, node, pos, spkt)

/* ======================= comments ======================= */
/*
Sends packet to move leaf
 */
/* ======================= declarations ======================= */
/*
type       parameter    i/o      description
---------  -----------  ------   -------------------------------------*/
HANDLE     hndle;       /* i     handle                               */
int        node;        /* i     vane node number                     */
long       pos;         /* i     new vane movement position           */
UINT8      *spkt;       /* i     sample packet                        */

/* ======================= log ======================= */
/*
return status description
-----------  -----------------------------------------------------------
 1           Success
-1           Failure date       comments
--------   -----------------------------------------------------------
08/10/93   Creation - Jeremy Wong
 */
/* ================================================================ */

{

INT16 ret16;
UINT8 pkt[20];

/*
   send packet to move leaf
*/

MLCVpkt (node, pos, spkt, pkt);
printf ("%s\n", pkt);

if ( pSENDPKT (hndle, (pUINT8) pkt, &ret16) ) {
   fputs ("Error: MLCVsend - pSENDPKT\n", stdout);
   goto ERROR_RETURN;
} if ( ret16 != 0 ) {
   fputs ("Error: MLCVsend - pSENDPKT: returned value\n", stdout);
   goto ERROR_RETURN;
} return (1);
```

```
ERROR_RETURN:
fputs ("Error: MLCVsend\n", stderr);
return (-1);

} mlcvstat.c
/* ========================= include files ========================= */ include "mlcv.h"
include <time.h>

/* ========================= function name ========================= */ int MLCVstat (hndle, flag, reg, map, node, start, interval)

/* ========================= comments ========================= */
/*
Send packet to check status of vane
 */
/* ========================= declarations ========================= */
/*
type      parameter    i/o      description
--------  -----------  -------  ----------------------------------------*/
HANDLE    hndle;       /* i     handle                                  */
int       flag;        /* i     information to check                    */
int       reg;         /* i     register to check                       */
int       map;         /* i     map number                              */
int       node;        /* i     vane node number                        */
clock_t   start;       /* i     start of timer                          */
clock_t   interval;    /* i     interval of timer                       */

/* ========================= log ========================= */
/*
return status description
---------------  --------------------------------------------------------
 1               Success
-1               Failure date      comments
--------  --------------------------------------------------------
08/10/93  Creation - Jeremy Wong
 */
/* ================================================================= */

{ int j, *k, m, r, stat;
INT16 ret16;
UINT16 uret16;
UINT8 src[17];
long i;
clock_t timeout;

/*
   send packet to check status of vane
*/ stat = 0;
/*start = clock ();*/
```

```
while ( !stat ) {
   if ( pREGSTAT (hndle, (UINT16) map, &uret16) ) {
      fputs ("Error: MLCVstat - pREGSTAT\n", stdout);
      goto ERROR_RETURN;
   }
   /*printf ("%d\n", uret16);*/
   if ( reg == 30 ) {
      m = 8;
      r = 0x30;
   }
   else if ( reg == 50 ) {
      m = 32;
      r = 0x50;
   }
   else if ( reg == 60 ) {
      m = 64;
      r = 0x60;
   } if ( (uret16 != 0) && (uret16 & m) ) {
      SYSbufinit (src, 0, sizeof (src));
      if ( pGETREG (hndle, (UINT8) r, (UINT16) map, (UINT16) 1,
            (pUINT8) &src[0], &ret16) ) {
         fputs ("Error: MLCVstat - pGETREG\n", stdout);
         goto ERROR_RETURN;
      } if ( ret16 != 0 ) {
         fputs ("Error: MLCVstat - pGETREG: returned value\n", stdout);
         goto ERROR_RETURN;
      } if ( reg == 30 ) {
         stat = 1;
         printf ("node %d\n", node);
      }
      else if ( reg == 50 ) {
         stat = 1;
         printf ("node %d\n", node);
      }
      else if ( reg == 60 ) {
         if ( flag == 0 ) {
            stat = 1;
            printf ("node %d\n", node);
         }
         else if ( flag == 1 ) {
            src[1] = 0;
            printf ("%02X\n", src[0]);
            k = (int *) &src[0];
            j = *k;
            if ( (j & 32) && !(j & 128) )
               stat = 1;
            printf ("node %d %d %d\n", node, j, stat);
         }
      }
   } if ( !stat ) {
      timeout = clock ();
      if ( ((float) (timeout - start) / (float) CLOCKS_PER_SEC) >
```

```
            (float) interval ) {
         stat = 1;
         goto ERROR_RETURN;
      }
   }
} return (1);

ERROR_RETURN:
fputs ("Error: MLCVstat\n", stderr);
return (-1);

} mlcvt.c
/* ======================= include files ======================= */ include "mlcv.h"

/* ======================= function name ======================= */ void main (argc, argv)

/* ======================= comments ======================= */
/*
MLC program (for testing)
 */
/* ======================= declarations ======================= */
/*
type       parameter      i/o     description
---------  -------------  ------  ---------------------------------*/
int        argc;          /* i    argument count                  */
char       **argv;         /* i    program arguments               */

/* ======================= log ======================= */
/*
return status description
----------  ----------------------------------------------------
 1          Success
-1          Failure date      comments
--------  ----------------------------------------------------
08/10/93  Creation - Jeremy Wong
 */
/* ================================================================ */

{ int status, found;
char filename[128];
mlc_vobjects *vobjects = NULL;

/*
   initialize mlc parameters
*/ status = MLCVinit (&vobjects);
if ( status != 1 ) goto ERROR_EXIT;
```

```
status = MLCVapos (vobjects->hndle,
                   vobjects->node_left, vobjects->node_right,
                   vobjects->old_left, vobjects->old_right);
if ( status != 1 ) goto ERROR_EXIT;

/*
   read input file of leaf positions
*/ found = 0;
while ( !found ) {
   printf ("Enter Filename (or quit to exit)> ");
   SYSbufinit (filename, 0, sizeof (filename));
   scanf ("%s", filename);
   if ( (strcmp (filename, "QUIT") == 0) ||
        (strcmp (filename, "quit") == 0) ) {
      found = 1;
   }
   else if ( strcmp (filename, "open.dat") == 0 ) {
      status = MLCVopen (vobjects->hndle,
                         vobjects->node_left, vobjects->node_right,
                         vobjects->leaf_left[0],vobjects->leaf_right[0],
                         vobjects->pos_left, vobjects->pos_right,
                         vobjects->old_left, vobjects->old_right,
                         vobjects->zero_left, vobjects->zero_right,
                         vobjects->oldc_left, vobjects->oldc_right,
                         vobjects->count_left, vobjects->count_right,
                         vobjects->spkt);
      /*if ( status != 1 ) goto ERROR_EXIT;*/
   }
   else if ( strcmp (filename, "") != 0 ) {
      SYSbufinit (vobjects->leaf_file, 0, sizeof (vobjects->leaf_file));
      strcpy (vobjects->leaf_file, filename);
      status = MLCVinpt (vobjects->leaf_file, &vobjects->ngantry,
                         vobjects->leaf_left, vobjects->leaf_right);
      /*if ( status != 1 ) goto ERROR_EXIT;*/ if ( status == 1 ) {
         status = MLCVleaf (vobjects->hndle,
                            vobjects->node_left, vobjects->node_right,
                            vobjects->leaf_left[0],vobjects->leaf_right[0],
                            vobjects->pos_left, vobjects->pos_right,
                            vobjects->old_left, vobjects->old_right,
                            vobjects->zero_left, vobjects->zero_right,
                            vobjects->oldc_left, vobjects->oldc_right,
                            vobjects->count_left, vobjects->count_right,
                            vobjects->spkt, 1);
         /*if ( status != 1 ) goto ERROR_EXIT;*/
      }
   }
} free (vobjects);
exit (1);

ERROR_EXIT:
fputs ("Error: MLCVT\n", stderr);
exit (-1);
```

} mlcvwait.c
/* ========================= include files ========================= */ include "mlcv.h"
include <time.h>

/* ========================= function name ========================= */ int MLCVwait (interval)

/* ========================= comments ========================= */
/*
Waits for an interval of time
*/
/* ========================= declarations ========================= */
/*
type      parameter    i/o      description
---------  -------------  -------  ------------------------------------------*/
float     interval;     /* i     interval to wait for                       */

/* ========================= log ========================= */
/*
return status description
--------------  ------------------------------------------------------------
 1              Success
-1              Failure date      comments
--------  ------------------------------------------------------------
08/10/93  Creation - Jeremy Wong
*/
/* ================================================================= */

{ int found;
clock_t start, timeout;

found = 0;
start = clock ();
while ( !found ) {
   timeout = clock ();
   if ( ((float) (timeout - start) / (float) CLOCKS_PER_SEC) >
        (float) interval )
      found = 1;
} return (1);

ERROR_RETURN:
fputs ("Error: MLCVwait\n", stderr);
return (-1);

}

What is claimed is:

1. A computer-controlled miniature multileaf collimator for use in small radiation field treatments and capable of dynamically shaping a radiation beam projected at isocenter, from a radiation source, comprising:
   a. a first bank of tapered leaves arranged in a substantially stacked configuration, each leaf having a proximal edge nearest to a radiation source, a distal edge furthest from a radiation source, and a leading edge perpendicular to said proximal edge, each of said leaves being sufficiently thin such that when the distal edge of each leaf is spaced approximately 75 centimeters from a radiation source projected at isocenter, the projected width of each leaf at isocenter is less than 5 millimeters;
   b. a second bank of tapered leaves arranged in a substantially stacked configuration and said second bank containing at least as many leaves as said first bank, each leaf having a proximal edge nearest to a radiation source, a distal edge furthest from a radiation source, and a leading edge perpendicular to said proximal edge and facing the leading edge of a leaf in said first bank, each of said leaves being sufficiently thin such that when the distal edge of each leaf is spaced approximately 75 centimeters from a radiation source projected at isocenter, the projected width of each leaf at isocenter is less than 5 millimeters;
   c. a drive shaft attached to each leaf such that axial movement of the drive shaft results in movement of a leaf in one of said banks toward or away from a leaf in the other of said banks;
   d. a reversible motor coupled to each drive shaft and capable of axially displacing each drive shaft, resulting in displacement of each leaf along an axis parallel to the proximal edge of the leaf;
   e. a first position-indicating device coupled to each motor and capable of detecting the position of each leaf and transmitting a first signal indicative of each leaf's position, said device further capable of detecting axial movement of each leaf of less than 0.1 millimeters;
   f. a motor controller electrically coupled to each motor, said controller comprising a memory capable of receiving, storing, and transmitting a signal indicative of the position of the leaf coupled to the drive shaft that is coupled to the motor to which the controller is coupled, and said controller further capable of receiving a signal from said position indicating device and transmitting a signal to the motor to change the position of the drive shaft a predetermined distance; and
   g. a programmable computer comprising a memory capable of storing desired position data for each leaf for a multiplicity of predetermined radiation beam shapes, and a display screen capable of indicating the position of each leaf, said computer further comprising a comparator electrically coupled to receive signals from said first position-indicating device, to compare said signals to desired position data stored in memory for each leaf, and to transmit a message to the display screen if the difference between the position indicated by the position-indicating signal and the desired position for any leaf is not within a predetermined tolerance.

2. The apparatus of claim 1, wherein the proximal edges of the leaves in each bank are arranged along an arc defined by the arc length of a circle whose radius equals the distance from a leaf in the center of one of said banks to a radiation source whose beam the collimator is intended to shape.

3. The apparatus of claim 1, wherein the number of leaves in each bank is sufficiently large such that the distance from the first leaf to the last leaf in each bank is at least 45 centimeters.

4. The apparatus of claim 1, wherein each leaf is comprised of tungsten by over 90% on a weight basis.

5. The apparatus of claim 1, wherein the leading edges of the leaves in one of said banks are stepped up and the leading edges of the leaves in the other of said banks are stepped down, such that when the leaves in each bank are moved toward each other as far as they can go, the stepped up portion of each leading edge overhangs the stepped down portion of a corresponding leading edge.

6. The apparatus of claim 1, wherein each leaf contains a front face comprising a horizontal ridge extending substantially across the front face, and a rear face comprising a horizontal channel extending substantially across the rear face and mounted at substantially the same height as said channel, such that each ridge protrudes into the channel of an adjacent leaf.

7. The apparatus of claim 1, wherein said drive shaft is a rotatable drive screw.

8. The apparatus of claim 1, wherein said first position-indicating device comprises a magnetic encoder coupled to said motor to send out a pulse signal at a set rate and at a predetermined phase angle when said motor is operating, said encoder changing the phase angle of its signal when the motor reverses direction.

9. The apparatus of claim 1, further comprising a second position-indicating device attached to each drive shaft and coupled to send a position-indicating signal to said computer, said second position-indicating device comprising:
   a. a wiper blade having a first end attached to said drive shaft such that when the drive shaft moves, the wiper blade moves, and a second end; and
   b. a potentiometer comprising a variable resistor coupled to the second end of said wiper blade such that movement of the wiper blade resulting from movement of the drive shaft results in a change in the resistance of said resistor.

10. The apparatus of claim 9, wherein the first and second leaf banks, motors, drive shafts, motor controllers, and first and second position-indicating devices are mounted in a housing.

11. A computer-controlled miniature multileaf collimator for use in small radiation field treatments and capable of dynamically shaping a radiation beam projected at isocenter from a radiation source, comprising:
   a. a first bank of tapered leaves arranged in a substantially stacked configuration, each leaf having a proximal edge nearest to a radiation source, a distal edge furthest from a radiation source, and a leading edge perpendicular to said proximal edge, each of said leaves being sufficiently thin such that when the distal edge of each leaf is spaced approximately 75 centimeters from a radiation source projected at isocenter, the projected width of each leaf at isocenter is less than 5 millimeters;
   b. a second bank of tapered leaves arranged in a substantially stacked configuration and said second bank containing at least as many leaves as said first bank, each leaf having a proximal edge nearest to a radiation source, a distal edge furthest from a radiation source, and a leading edge perpendicular to said proximal edge and facing the leading edge of a leaf in said first bank, each of said leaves being sufficiently thin such that when the distal edge of each leaf is spaced approximately 75 centimeters from a radiation source projected at isocenter, the projected width of each leaf at isocenter is less than 5 millimeters;

c. a drive shaft attached to each leaf such that axial movement of the drive shaft results in movement of the leading edge of the leaf in one of said banks toward or away from a leaf in the other of said banks;

d. a reversible motor coupled to each drive shaft and capable of axially displacing each drive shaft, resulting in axial displacement of each leaf;

e. a first position-indicating device coupled to each motor and capable of detecting the position of the leaf attached to the drive shaft that is coupled to the motor and further capable of transmitting a first signal indicative of the leaf's position, said device further capable of detecting axial movement of each leaf of less than 0.1 millimeters;

f. a motor controller electrically coupled to each motor, said controller comprising a memory capable of receiving, storing, and transmitting a signal indicative of the position of the leaf coupled to the drive shaft that is coupled to the motor to which the controller is coupled, and said controller further capable of receiving a signal from said position indicating device and transmitting a signal to the motor to change the position of the drive shaft a predetermined distance;

g. a second position-indicating device attached to each drive shaft coupled to send a position-indicating signal indicative of the position of the leaf attached to the drive shaft; and h. a programmable computer comprising a memory capable of storing desired position data for each leaf for a multiplicity of predetermined radiation beam shapes, and a display screen capable of indicating the position of each leaf, said computer further comprising a comparator electrically coupled to receive signals from said first position-indicating device and from said second positioning indicating device, to compare said signals to desired position data stored in memory for each leaf, and to transmit a message to the display screen if the difference between the position indicated by the position-indicating signal and the desired position for any leaf is not within a predetermined tolerance.

12. The apparatus of claim 11, wherein said second position-indicating means comprises:

a. a wiper blade having a first end attached to said drive shaft such that when the drive shaft moves, the wiper blade moves, and a second end; and b. a potentiometer comprising a variable resistor coupled to the second end of said wiper blade such that movement of the wider blade resulting from movement of the drive shaft results in a change in the resistance of said resistor.

13. The apparatus of claim 11, wherein each of said reversible motors comprises:

a. a rotatable motor shaft;

b. a first drive Gear attached to said rotatable motor shaft; and c. a second drive gear attached to said drive shaft and rotatably coupled to said first drive gear.

14. A computer-controlled miniature multileaf collimator for use in small radiation field treatments and capable of dynamically shaping a radiation beam projected at isocenter from a radiation source, comprising:

a. a first bank of tapered leaves arranged in a substantially stacked configuration, each leaf having a proximal edge nearest to a radiation source, a distal edge furthest from a radiation source, and a leading edge perpendicular to said proximal edge, each of said leaves being sufficiently thin such that when the distal edge of each leaf is spaced approximately 75 centimeters from a radiation source projected at isocenter, the projected width of each leaf at isocenter is less than 5 millimeters;

b. a second bank of tapered leaves arranged in a substantially stacked configuration and said second bank containing at least as many leaves as said first bank, each leaf having a proximal edge nearest to a radiation source, a distal edge furthest from a radiation source, and a leading edge perpendicular to said proximal edge and facing the leading edge of a leaf in said first bank, each of said leaves being sufficiently thin such that when the distal edge of each leaf is spaced approximately 75 centimeters from a radiation source projected at isocenter, the projected width of each leaf at isocenter is less than 5 millimeters;

c. a drive shaft attached to each leaf such that axial movement of the drive shaft results in movement of the leading edge of the leaf in one of said banks toward or away from a leaf in the other of said banks;

d. a reversible motor coupled to each drive shaft and capable of axially displacing each drive shaft, resulting in axial displacement of each leaf;

e. a first position-indicating device comprising a magnetic encoder coupled to said motor to send out a pulse signal at a set rate and at a predetermined phase angle when said motor is operating, said encoder changing the phase angle of its signal when the motor reverses direction, said position-indicating device further comprising a counter capable of counting the pulses at each phase angle generated by the encoder and the calculator capable of correlating pulses to axial drive shaft displacement, said position-indicating devices coupled to each motor and capable of detecting the position of the leaf attached to the drive shaft that is coupled to the motor and further capable of transmitting a first signal indicative of the leaf's position;

f. a motor controller electrically coupled to each motor, said controller comprising a memory capable of receiving, storing, and transmitting a signal indicative of the position of the leaf coupled to the drive shaft that is coupled to the motor to which the controller is coupled, and said controller further capable of receiving a signal from said position indicating device and transmitting a signal to the motor to change the position of the drive shaft a predetermined distance;

g. a second position indicating device attached to each drive shaft coupled to send a position-indicating signal indicative of the position of the leaf attached to the drive shaft; and h. a programmable computer comprising a memory capable of storing desired position data for each leaf for a multiplicity of predetermined radiation beam shapes, and a display a display screen capable of indicating the position of each leaf, said computer further comprising a comparator electrically coupled to receive signals from said first position-indicating device and from said second positioning indicating device, to compare said signals to desired position data stored in memory for each leaf, and to transmit a message to the display screen if the difference between the position indicated by the position-indicating signal and the desired position for any leaf is not within a predetermined tolerance.

15. The apparatus of claim 14, further comprising a radiation source capable of projecting a radiation beam at isocenter, said source mounted above the intersection of said first and second leaf banks such that the proximal edges of said leaves are nearest to said radiation source.

16. The apparatus of claim 15, wherein said radiation source is spaced approximately 75 centimeters from the distal edges of said leaves.

17. The apparatus of claim 5, wherein the leaves in each bank are arranged along an arc defined by the arc length of a circle whose radius is the distance from a leaf in the center of one of said banks to said radiation source.

18. The apparatus of claim 14, wherein said first and second banks of leaves, drive shafts, motors, motor controllers, and position-indicating devices are contained in a portable collimator housing.

19. The apparatus of claim 18, further comprising a radiation source housing containing said radiation source.

20. The apparatus of claim 4, wherein said magnetic encoder is capable of detecting each full rotation of said drive shaft.

* * * * *